United States Patent [19]

Chum et al.

[11] Patent Number: 5,223,601
[45] Date of Patent: Jun. 29, 1993

[54] PHENOLIC COMPOUNDS CONTAINING/NEUTRAL FRACTIONS EXTRACT AND PRODUCTS DERIVED THEREFROM FROM FRACTIONATED FAST-PYROLYSIS OILS

[75] Inventors: Helena L. Chum, Arvada; Stuart K. Black, Denver; James P. Diebold, Lakewood, all of Colo.; Roland E. Kreibich, Auburn, Wash.

[73] Assignee: Midwest Research Institute Ventures, Inc., Kansas City, Mo.

[21] Appl. No.: 647,020

[22] Filed: Jan. 29, 1991

Related U.S. Application Data

[63] Continuation-in-part of Ser. No. 456,654, Dec. 29, 1988, abandoned.

[51] Int. Cl.$^5$ ............... C07C 37/20; C08G 14/02
[52] U.S. Cl. .................... 528/129; 428/514; 428/529; 528/1; 568/762; 585/240
[58] Field of Search ............ 528/1, 129; 568/762; 428/514, 529; 585/240

[56] References Cited

U.S. PATENT DOCUMENTS

| | | | |
|---|---|---|---|
| 3,293,200 | 12/1966 | MacGregor | 428/529 |
| 4,233,465 | 11/1980 | Gallivan | 568/727 |
| 4,508,886 | 4/1985 | Russel et al. | 528/1 |
| 4,942,269 | 7/1990 | Chum | 585/240 |

Primary Examiner—III Kight
Assistant Examiner—Shelley A. Wright
Attorney, Agent, or Firm—Antonelli, Terry, Stout & Kraus

[57] ABSTRACT

A process for preparing phenol-formaldehyde novolak resins and molding compositions in which portions of the phenol normally contained in said resins are replaced by a phenol/neutral fractions extract obtained from fractionating fast-pyrolysis oils. The fractionation consists of a neutralization stage which can be carried out with aqueous solutions of bases or appropriate bases in the dry state, followed by solvent extraction with an organic solvent having at least a moderate solubility parameter and good hydrogen bonding capacity.

Phenolic compounds-containing/neutral fractions extracts obtained by fractionating fast-pyrolysis oils from a lignocellulosic material, is such that the oil is initially in the pH range of 2-4, being neutralized with an aqueous bicarbonate base, and extracted into a solvent having a solubility parameter of approximately 8.4-9.11 [cal/cm$^3$]$^{\frac{1}{2}}$ with polar components in the 1.8-3.0 range and hydrogen bonding components in the 2-4.8 range and the recovery of the product extract from the solvent with no further purification being needed for use in adhesives and molding compounds.

The product extract is characterized as being a mixture of very different compounds having a wide variety of chemical functionalities, including phenolic, carbonyl, aldehyde, methoxyl, vinyl and hydroxyl. The use of the product extract on phenol-formaldehyde thermosetting resins is shown to have advantages over the conventional phenol-formaldehyde resins.

116 Claims, 10 Drawing Sheets

CHANGE IN VISCOSITY OF PN AT 45 °C WITH INCREASING SEVERITY OF STORAGE

SEVERITY OF STORAGE EFFECT ON WEIGHT AVERAGE MWt. AND POLYDISPERSITY

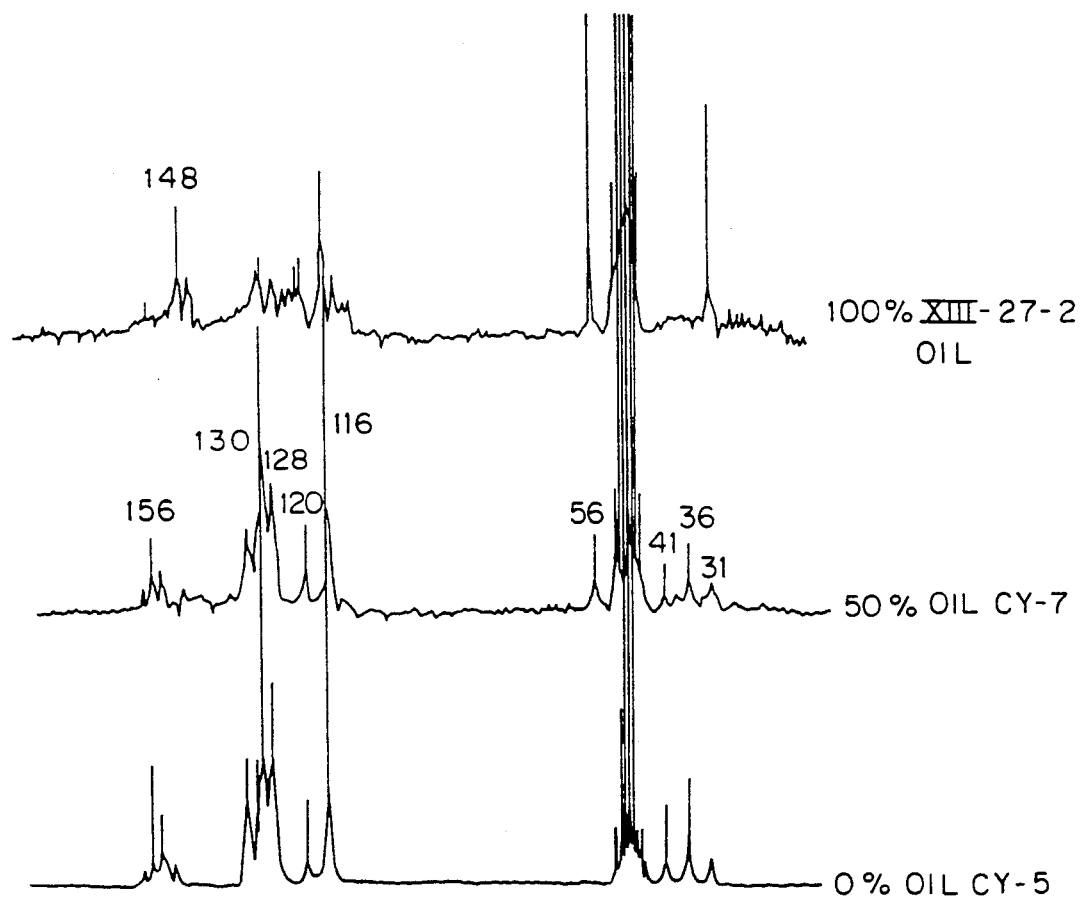

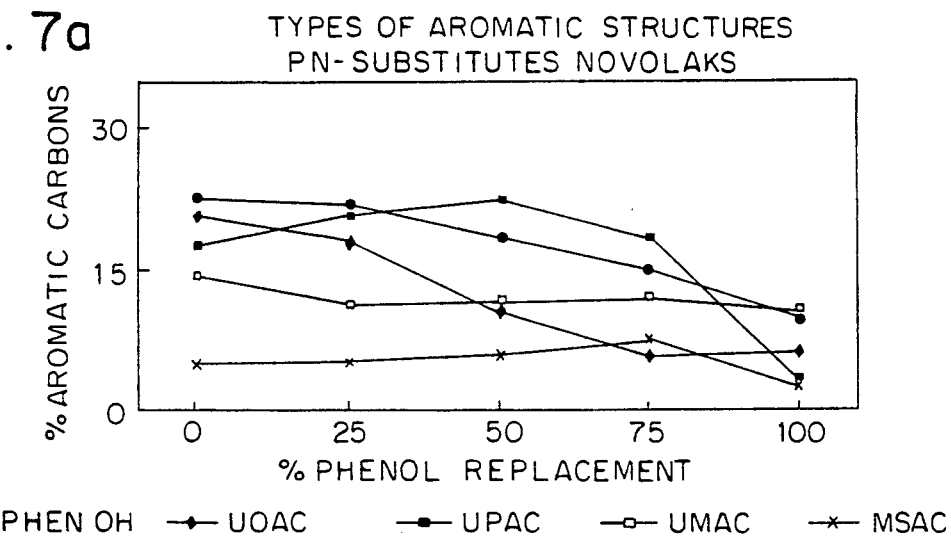
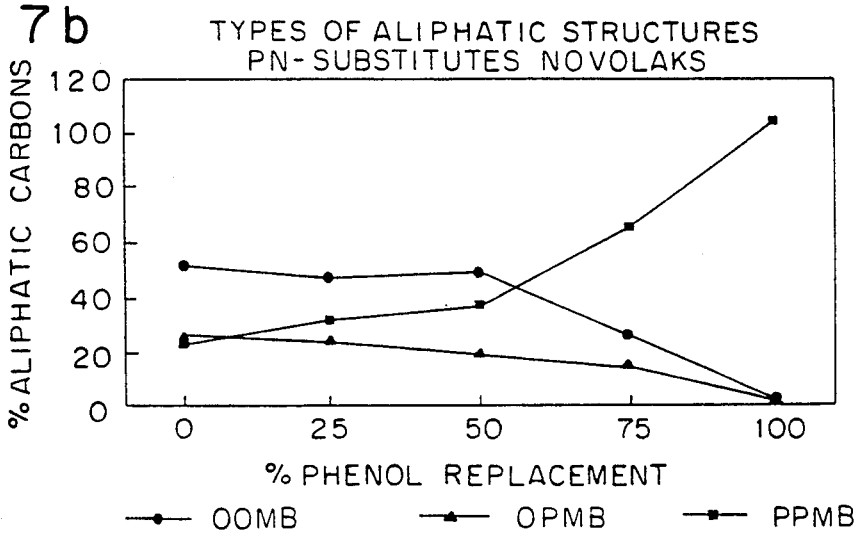
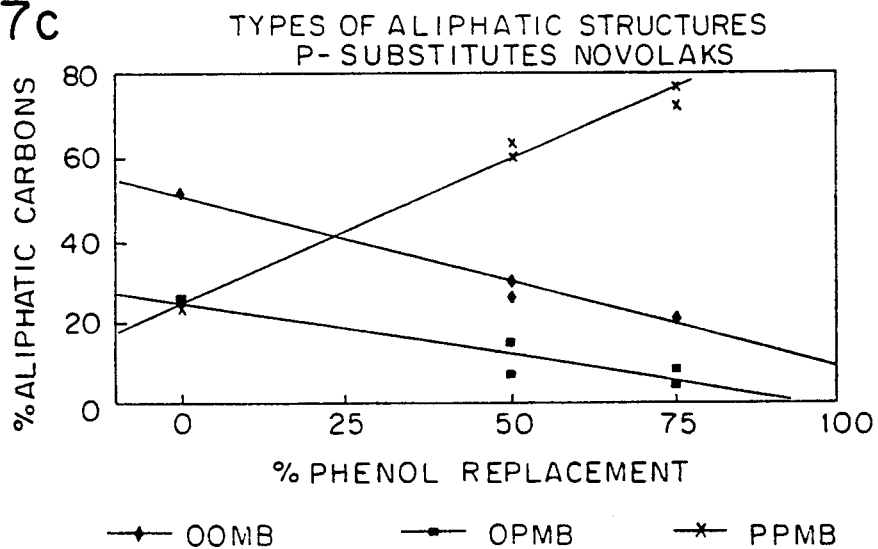

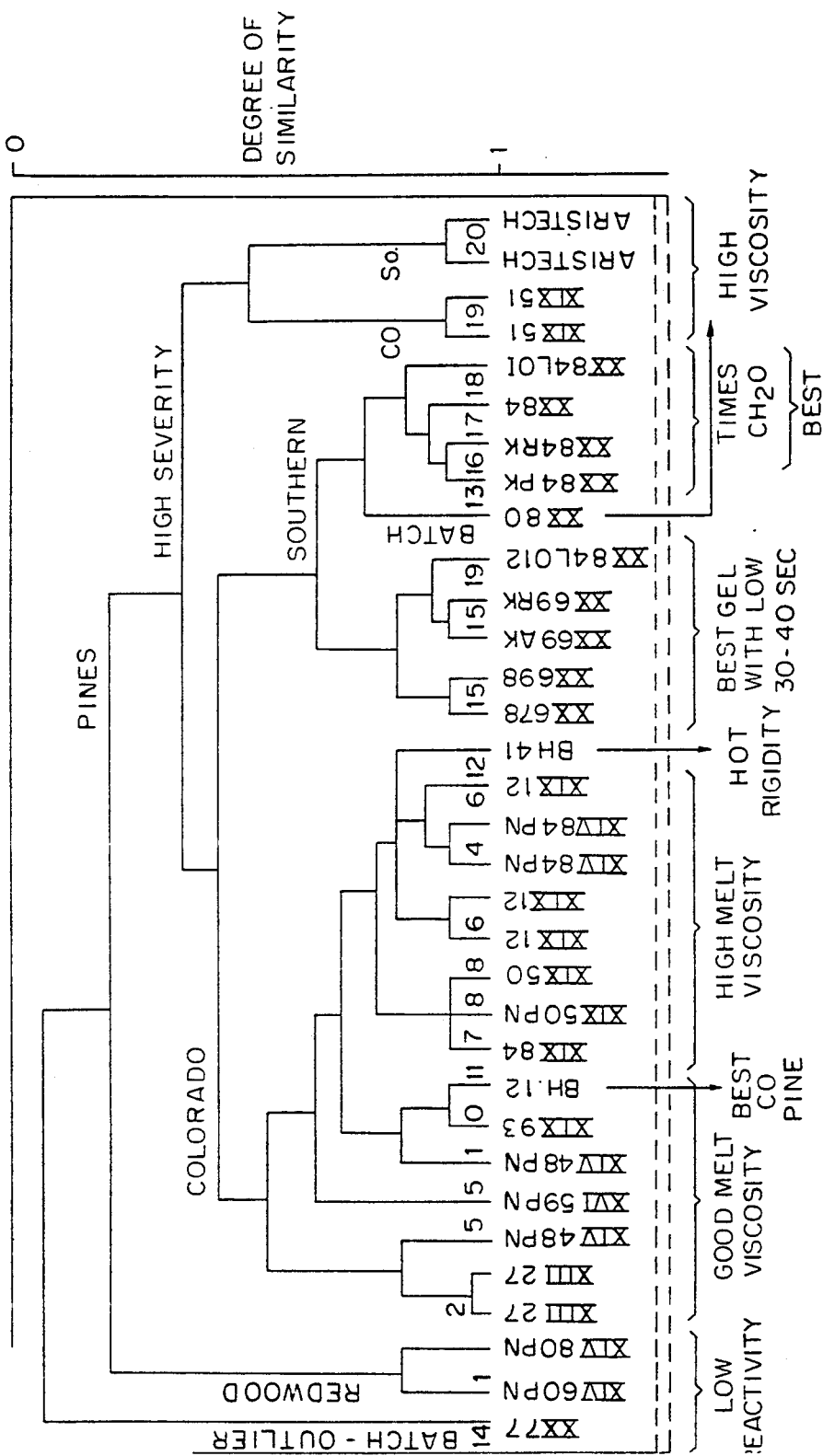

PHENOLIC COMPOUNDS CONTAINING/NEUTRAL FRACTIONS EXTRACT AND PRODUCTS DERIVED THEREFROM FROM FRACTIONATED FAST-PYROLYSIS OILS

CONTRACTUAL ORIGIN OF THE INVENTION

The United States Government has rights in this invention under Contract No. DE-AC02-83H10093 between the United States Department of Energy and the Solar Energy Research Institute, a Division of the Midwest Research Institute.

BACKGROUND OF THE INVENTION

1. Field of the Invention

The present application is a continuation-in-part of application of U.S. application Ser. No. 07/456,654 filed Dec. 29, 1989, now abandoned, and the present application incorporates Ser. No. 07/456,654 by reference in its entirety.

The invention relates generally to phenolic compounds containing/neutral fractions extract obtained from the treatment of "Fast-Pyrolysis Oils". Specifically, the present invention relates to phenolic compounds-containing/neutral fractions extract obtained by a process of fractionating fast pyrolysis oils from biomass materials, comprising admixing said oils with an organic solvent having a solubility parameter of about 8.4–9.1 $[cal/cm^3]^{\frac{1}{2}}$, polar components in the 1.8–3.0 range, and hydrogen bonding components in the 2–4.8 range; separating the organic solvent soluble fractions containing the phenolic compounds/neutral fractions from the mixture and admixing it with water to extract water-soluble materials therefrom; separating the organic solvent soluble fractions from the water fractions and admixing said solvent fractions with an aqueous alkali metal bicarbonate solution to extract strong organic acids and highly polar compounds from the solvent fractions; and separating the residual organic solvent soluble fraction and removing the organic solvent therefrom to produce phenolic compounds/neutral fractions extract. Alternatively, prior to admixing the organic solvent with the pyrolysis oil, water can be added or be present in the oils by virtue of the use of steam as carrier gas in the pyrolysis. Neutralization can be done at this point with solid alkali metal bicarbonate or carbonate or an alkaline earth bicarbonate or carbonate. Then extraction of said neutralized pyrolysis oil-/aqueous layer with the organic solvent removes the phenolic compounds/neutral fractions, which can be isolated by removing the organic solvent.

2. Description of the Prior Art

Adhesive resins are utilized in a wide variety of applications including the bonding of wood layers to manufacture plywood (resoles), the formation of molded pieces and articles (novolaks), and the like. There are certain disadvantages, however, to existing techniques for the manufacture of phenolic resins. Phenol has been traditionally derived from petroleum based products. Because the production of petroleum-based phenol is very expensive, there have been efforts in recent years to at least partially substitute the phenol in such resins with inexpensive phenols derived from wood-based products or extracts. More specifically, phenols derived from bark, wood chips and the like have been looked at as potential substitutes for petroleum based phenol in such resins.

The pyrolysis of biomass, and in particular lignocellulosic materials, is known to produce a complex mixture of phenolic compounds which are derived primarily from the lignin fraction of the biomass. In nature, lignin acts as an adhesive to bind the cellulose fibers together. Therefore, lignin and lignin-derived materials from wood seem like a natural starting point for the development of biomass-based adhesive resins. Sources for such phenolic materials include black liquor from kraft pulping and other pulping processes, where the lignin is present in a stream which is commonly burned to recover process heat and chemicals. Unfortunately, these lignins are generally not very reactive after recovery for a variety of reasons, such as high molecular weight, chemical modification during recovery due to condensation reactions and the like, in addition to the lack of reproducibility of proprieties. Various types of pyrolysis processes have also been utilized, frequently yielding disappointing results. Fast-pyrolysis, however, has proven to be an exception to this.

Fast-pyrolysis of biomass features the depolymerization of cellulosic, lignin, and hemicellulosic polymers, which produces an oil having a relatively low molecular weight and which has considerable chemical activity under proper conditions. Crude pyrolysis oil apparently undergoes a limited amount of repolymerization upon physical condensation. However, the thermal stability of fast-pyrolysis oils at room temperature is qualitatively quite good implying a good shelf life for the oils, although at 100° C. the crude oils solidify overnight. Solidified pyrolysis oils are characterized by their low strength and brittleness. The potential of pyrolysis products for use in adhesive resins is not a new concept, as indicated above, but the efficient and cost-effective reduction of this to practice has been an elusive goal for many years.

The general approach of producing phenols from biomass has previously been to purify the phenolic fractions present in the pyrolysis oils by the use of solvents to partition the constituents by difference in solubility and reactivity. Different variations of solvents, reagents, and sequence of extractions have been developed in the past, and this has resulted in different partitioning coefficients for a couple of hundred of chemical compounds known to be in pyrolysis oils, and therefore produced extracts having differing relative compositions. Another significant difference between various research efforts pertaining to this area in the past has been the type of pyrolysis process used to produce the oils used as feed in the extraction process. These include updraft gasification, entrained fast-pyrolysis, and fluidized bed fast-pyrolysis, all at atmospheric pressures, as well as slow, high pressure liquefaction processes. In addition, both hardwoods and softwoods have been used as feedstock in the past for the oil forming processes. These differences in extraction and pyrolysis processes, coupled with the differences in feedstock, yield different materials as products for replacement of phenol in phenolic resin application. Thus, as indicated below, the usefulness of a particular extract as an adhesive component is quite different, one from the other.

U.S. Pat. Nos. 4,209,647 and 4,223,465 disclose methods for recovering phenolic fractions from oil obtained by pyrolysis of lignocellulosic materials and the subsequent use of that fraction in the making of phenol-formaldehyde resins. However, these processes use pyrolysis oils which are usually formed at ill-defined temperatures and which have undergone phase separation cracking and some condensation, and suffer from very low yields.

A number of other patents including U.S. Pat. Nos. 2,172,415, 2,203,217, 3,069,354, 3,309,356 and 4,508,886 as well as Japanese Patent No. 38-16895 all disclose a variety of processes for recovering phenolic fractions from oils derived from biomass materials and oil resources. These processes vary in the particular procedures and techniques utilized to ultimately separate the phenolic fractions as well as the procedures utilized to derive the oil from the biomass or other feed material. However, they all have a common thread linking them in that the ultimate end product is a phenolic fraction, which is desired to be as pure as possible. This phenolic fraction is then utilized to produce phenol-formaldehyde resins. These phenolic substitutes usually were slower in reactivity with formaldehyde than phenol derived from petroleum-base products. The complex procedures disclosed in these references to produce relatively pure phenolic fractions are not particularly economical. Thus, there is still a need for a process designed to produce pyrolysis oils from lignocellulosic materials and then extract a phenolic composition from such oils which is capable of functioning as efficiently as petroleum-based phenols in the formation of phenol-formaldehyde resins and which is less expensive to produce.

SUMMARY OF THE INVENTION

Accordingly, it is one object of the present invention to provide phenolic compounds-containing/neutral fractions extract obtained from fast-pyrolysis oils.

It is another object of the present invention to provide phenolic compounds-containing/neutral fractions extract obtained from a process of fractionating fast-pyrolysis oils derived from biomass materials.

Another object of the present invention is to provide phenolic compounds-containing/neutral fractions extract, wherein the neutral fractions have molecular weights of from 100–800.

The foregoing and other objects in accordance with the present invention, as embodied and broadly described herein, is accomplished by: admixing said oils with an organic solvent having a solubility parameter of approximately 8.4–9.1 $[cal/cm^3]^{\frac{1}{2}}$ polar components in the 1.8–3.0 range and hydrogen bonding components in the 2–4.8 range; separating the organic solvent-soluble fraction containing the phenolic compounds/neutral fractions from said mixture and admixing it with water to extract water-soluble materials therefrom; separating the organic solvent-soluble fraction from said water fraction and admixing said solvent fraction with an aqueous alkali metal bicarbonate solution to extract strong organic acids and highly polar compounds from said solvent fractions; and separating the residual organic solvent soluble fraction and removing the organic solvent therefrom to produce said phenolic compounds/neutral fractions extract.

The objects in accordance with the present invention, as embodied and broadly described herein, can further be accomplished by: admixing said oils which contains organic and aqueous condensates with basic materials in a relatively dry, solid state and selected from the group consisting of sodium hydroxide, sodium bicarbonate, sodium carbonate, sodium sesquicarbonate, potassium hydroxide, potassium bicarbonate, potassium carbonate, ammonium hydroxide, ammonium bicarbonate, ammonium carbonate, lithium hydroxide, lithium bicarbonate, lithium carbonate, calcium hydroxide, calcium carbonate, magnesium hydroxide, magnesium carbonate, hydrates thereof, or mixtures thereof, and chosen to be able to neutralize acidic components of the condensates and to render such acidic components and other polar compounds less soluble in the organic phase; admixing said neutralized condensates with an organic solvent having at least a moderate solubility parameter and good hydrogen bonding capability, said organic solvent has a solubility parameter of approximately 8.4 to 9.1 $(cal/cm^3)^{\frac{1}{2}}$ with polar components in the 1.9–3.0 range and hydrogen bonding components in the 2–4.5 range, utilizing said solvent to extract phenolic-containing and neutral fractions from the organic aqueous phases into the solvent phase; separating the organic solvent-soluble fraction having the phenolic-containing and neutral fractions from the aqueous fraction; and removing the organic solvent therefrom to produce said phenolic-containing and neutrals compositions in a form substantially free from said solvent.

BRIEF DESCRIPTION OF THE DRAWINGS

The accompanying drawings which are incorporated in and form a part of the specification illustrate preferred embodiments of the present invention, and together with the description, serve to explain the principles of the invention.

FIG. 6 illustrates the carbon-13 NMR of the phenolic resins compared to the spectrum of the neat P/N product No. 2, and a novolak containing 50% of that P/N product, using a 90 MHz Jeolco instrument. Numbers indicated are the chemical shifts in parts per million.

FIG. 7a illustrates the relative changes of specific types of carbons (see text) as a function of the replacement of phenol with the P/N products in the aromatic region (110–160 ppm). FIG. 7b illustrates similar changes for the aliphatic region (30–40 ppm) for P/N product #2 from Colorado pines, whereas FIG. 7c illustrates the same region for Douglas fir bark phenolics (Example III).

FIG. 8 illustrates the groups of P/N products that are similar to each other based on their spectral properties as illustrated in FIG. 3. The diagram is called a dendrogram; identical samples have an ordinate value of one.

DETAILED DESCRIPTION OF THE PREFERRED EMBODIMENTS

Figure 1:
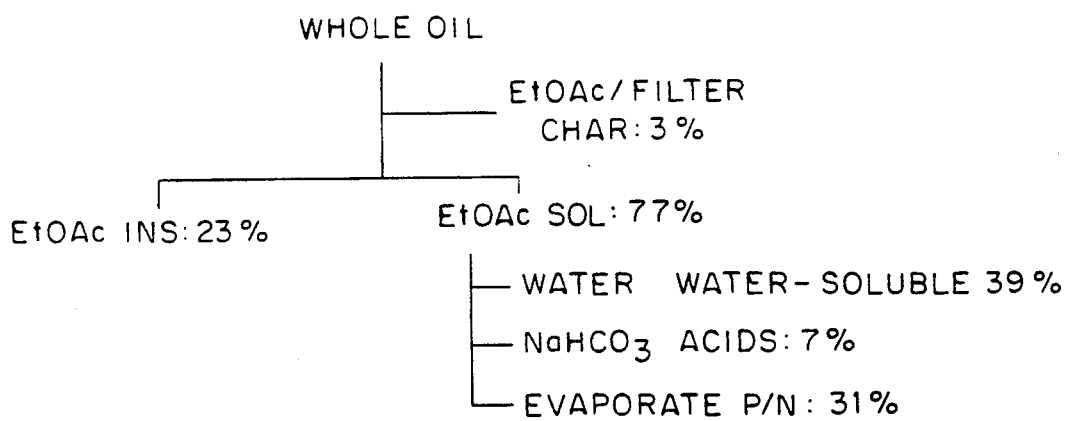
FIG. 1 is a flow diagram illustrating the process of the present invention.

Part A: The Process and P/N Products

During the course of studying the problem of producing inexpensive but effective phenolic compositions from biomass, it was discovered that certain polar organic solvents having at least a moderate solubility parameter, a moderate degree of polarity, and good hydrogen bonding capabilities were capable of extracting both phenolic and neutral fractions from fast-pyrolysis oils. Moreover, it was discovered that this extraction technique was equally effective for fast pyrolysis oils of differing starting materials. Thus, it was discovered that the present invention may be utilized with pyrolysis oils derived from pine sawdust, bark, grasses, and softwoods as well as certain hardwoods with very little differences in the final results. Apparently, the fast-pyrolysis process preserves the delicate products in monomeric and oligomeric states. A key factor in the process of the present invention is that the oils derived from the lignocellulosic materials must be obtained utilizing a fast-pyrolysis process. Fast-pyrolysis is generally known in the art, and such a technique has been specifically disclosed in an article entitled, "Production of Primary Pyrolysis Oils in a Vortex Reaction", American Chemical Society Division of Fuel Chemistry Preprints, Vol. 32, No. 2, pp. 21-28 (1987). Thus, details of such fast pyrolysis techniques need not be specifically repeated and disclosed herein, and the contents of this Article are therefore specifically incorporated herein by reference. Oils from other fast-pyrolysis concepts are also good feedstocks. Such concepts are referenced in "Fast-Pyrolysis of Pretreated Wood and Cellulose", Ibidem, pp. 29-35 (1987), and "Preliminary Data for Scale up of a Biomass Vacuum Pyrolysis Reactor", Ibidem, pp. 12-20 (1987); "The Role of Temperature in the Fast-Pyrolysis of Cellulose and Wood", Industrial Engineering Chemistry Research, Vol. 27, pp. 8-15 (1988), and "Oil From Biomass by Entrained Flow Pyrolysis", Biotechnology and Bioengineering Symposium, No. 14, pp. 15-20 (1984).

In one concept, the biomass solids in such fast-pyrolysis of biomass solids entrain the feedstock particulates tangentially at high velocities into a vortex reactor tube which has an internal surface design that guides the centrifuged solids into a tight helical pathway on the rector wall. This results in a very high heat transfer to the wood or other feedstock particles which allows mild cleavage of the polymeric components of the feedstock. Consequently, high yields of pyrolysis oils from dry wood (greater than 55%) and/or bark are generally obtained. If the feedstock is not fully pyrolyzed, the solids enter a recycle loop located at the end of the vortex reactor. After attrition to a powder, char particles elute with the vapor stream and are isolated in a char cyclone. Alternative methods to produce primary pyrolysis oils thought to be similar to fast-pyrolysis include fast-pyrolysis in fluidized beds, in entrained flow reactors, and vacuum pyrolysis.

Utilizing the process of the present invention, the pyrolysis oils are fractionated in a unique way, which produces a combined phenolics and neutral fraction of high phenolic hydroxyl and aldehyde content. In general, a polar organic solvent is added to the oils to separate the phenolic and neutral fractions from said oils. The organic solvent-soluble fraction is then admixed with water to extract water-soluble materials, and then further washed with an aqueous alkali metal bicarbonate solution to extract strong organic acids and highly polar compounds. The residual organic solvent-soluble fraction containing the phenol and neutral fractions is then isolated, and the organic solvent is removed, preferably by evaporation, to produce a phenol-containing composition having the phenolic compounds-containing/neutral fractions (to be named P/N product) of the original raw oils. The yield of the P/N product from the extract is about 30% of the fast-pyrolysis oil derived from sawdust and about 50% of the oil derived from bark.

In the prior art of phenol-producing processes, the processes ended only after the phenolic-containing compositions were generally reduced to purified phenolics only, with the neutral fractions being removed. By neutral fractions, it is meant those compounds which are not solubilized by a strong base such as sodium hydroxide, and have molecular weights of approximately 100-800 determined by high performance size exclusion chromatography with polystyrene standards. Such neutral fractions include carbonyl compounds, furfural type compounds and the like. It was apparently previously believed that such neutral fractions must also be extracted in order to provide a phenol composition which may be utilized as a substitute for petroleum-based phenols in the production of phenol-formaldehyde adhesive resins. It has been discovered, however, that by utilizing the process of the present invention, the resultant composition containing phenolic compounds-containing/neutral fractions function just as well as and in some aspects better than relatively pure phenol composition in the production of phenol-formaldehyde resins because, since the compositions have aldehyde groups, much less formaldehyde is needed to make these formulations. Reduced formaldehyde levels lead to minimization of potential environmental problems. In addition, the economics are such that it is substantially less expensive to manufacture the P/N. Moreover, by utilizing the entire fraction which includes phenolic compounds-containing/neutral fractions as feedstocks for resins, we discovered that this prevented the pyrolysis-derived reactive phenolics from undergoing air oxidation under alkaline conditions, which prevails when one isolates and purifies the phenolics fraction alone. This latter air oxidation which can be a problem, is a condition that prevails in many prior art techniques and is accomplished by extractions with aqueous sodium hydroxide solutions, and is accompanied by the formation of insoluble tars and reduced yields of phenolics.

Investigations of the fractionation scheme of the present invention, as generally described above utilizing pine fast-pyrolysis oils were carried out employing a number of different solvents to determine the preferred and optimum solvents and the requirements thereof. In general, the whole oil was first dissolved in the organic solvent preferably in an oil:solvent ratio of 0.5:1 to 1:3 by weight. The oil was initially filtered to separate char which is carried over from the pyrolysis reactor operations. Upon standing, the solvent/oil mixture then separates into two phases, the solvent-soluble phase and the solvent-insoluble phase.

One requirement for the organic solvent is that the solvent and water exhibit low mutual solubility. Preferably, acceptable solvents include those with solubilities that are not more than about 10 grams of solvent in 100 grams of water and about 8 grams of water in 100 grams of solvent, in terms of mutual solubility. Thus, this solvent requirement eliminates all low molecular-weight alcohols (methanol, ethanol, propanol) that are infinitely soluble in water, methlethylketone, the carboxylic acids (formic, acetic and propionic) which are infinitely soluble in water, and methyl formate. The classes of solvents that would be acceptable only from a pure mutual solubility point of view include hydrocarbons (aliphatic, aromatic), higher alcohols (greater than 6 carbon atoms), higher ketones (greater than 5 carbon atoms), esters (greater than 2 carbon atoms), ethers, polychlorinated hydrocarbons, and higher nitriles (greater than 4 carbon atoms).

Another requirement for the organic solvent which further limits potential candidates is that the solvent has a low boiling point or a low boiling point azeotrope. The preferred boiling point is around 100° C. or less, to avoid thermal degration of the P/N product. Yet another requirement for the organic solvent is that the solvent have some degree of polarity, preferably high polarity, as well as high hydrogen bonding capability in addition to a moderate-to-good solubility parameter. The solubility parameter is defined as a measure of all the intermolecular forces present in the solvent. The overall solubility parameter is composed of components due to dispersive forces, polar forces (caused by a high dipole moment in the molecule), and hydrogen bonding capability. Solubility parameters, measured in $[cal/cm^3]^{\frac{1}{2}}$, range from 5–7 for hydrocarbons and nonpolar solvents, to 14.5 for methanol and 23.4 for water-highly polar substances. Thus, low boiling point ethers alone, such as diethyl ether, are excluded from being preferred solvents since they have a very low solubility parameter (7.4) and very low polar components (1.4). Hydrocarbons are also excluded as preferred solvents because of their very low polar components and overall low solubility parameters.

It has been found that the preferred group of solvents for use in the present invention include acetate and propionate esters, methyl alkyl ketones and ethyl alkyl ketones. More specific preferred organic solvents are listed below in Table I, the most preferred being ethyl acetate due to its availability, relatively low solubility in water, and high oil solubility. The most preferred range for solubility parameters includes 8.4–9.1 with polar components in the 1.8–3.0 range and hydrogen bonding components in the 2–4.5 range. Additional acceptable solvents are the isomers of those listed in Table I. Mixtures of esters are also acceptable, as are mixtures of the higher ketones. Ternary solvent systems also are possible, primarily mixtures of esters and high molecular weight ethers such as diisopropylether to reduce the boiling point. However, the most preferred solvents for use with the present invention are ethyl acetate, as indicated above, as well as butyl acetate and methylisobutylketone.

TABLE I

| Property | Acetate Esters | | | Methyl Ketones | | | Ethyl Ketone |
| --- | --- | --- | --- | --- | --- | --- | --- |
| | Ethyl | Propyl | Butyl | i-Butyl | i-Amyl | i-Propyl | Ethyl |
| Mol. wt | 88.1 | 102.1 | 116.2 | 100.2 | 114.2 | 86.14 | 86.14 |
| Boiling Point, °C. (at 70 mmHg) | 77.1 | 101.5 | 126.1 | 116.5 | 144 | 92 | 102.0 |
| Density, 20° C. | 0.90 | 0.89 | 0.88 | 0.80 | 0.88 | 0.81 | 0.81 |
| Heat Vaporization, | | | | | | | |
| kcal/mole (20° C.) | 8.4 | 9.3 | 10.4 | 10.00 | | | |
| kcal/mole (b.p.) | 7.71 | 8.20 | 8.58 | 8.50 | | 7.73 | 8.06 |
| Solubility, wt % in water | 8.08 | 2.3 | 0.43 | 1.7 | −0 | −2 | 2.4 |
| Water in Azeotrope | 2.94 | 3.9 | 1.86 | 1.9 | −0 | −2 | 2.6 |
| Wter wt % | 9.47 | 14 | 28.7 | 24.3 | 44.0 | | 24 |
| ′ boiling point, °C. | 70.38 | 82.2 | 90.2 | 87.9 | 94.7 | | 82.9 |
| Dielectric Constant | 6.02 | 6.00 | 5.01 | 13.11 | | | 17.0 |
| Solubility param. | | | | | | | |
| Total | 9.1 | 8.4 | 8.46 | 8.57 | 8.55 | 8.5 | 8.8 |
| Dispesive comp. | 7.44 | 6.6 | 7.67 | 7.49 | 7.80 | | −7.8 |
| Polar comp. | 2.6 | 2.0 | 1.8 | 3.0 | 2.8 | | −3.4 |
| H-Bonding comp. | 4.5 | 4.8 | 3.1 | 2.0 | 2.0 | | 2.0 |

As indicated above, the preferred solvent is ethyl acetate, and the process of the present invention will hereinafter be described in terms of utilizing ethyl acetate as the solvent. However, it should be understood that any of the identified solvents may be utilized in the following described process. As previously indicated, the fast pyrolysis oil/water solution is at a pH of 2–4 prior to dissolving the same in the ethyl acetate and filtering. Upon standing, the ethyl acetate/pyrolysis oils mixture separates into two phases. Chemical spectroscopic analysis revealed that the ethyl acetate-insoluble fraction contains carbohydrate and carbohydrate-derived products. The ethyl acetate-soluble fraction, containing the phenolic compounds-containing/neutral fractions, is then separated and washed with water to remove the remaining water soluble carbohydrate and carbohydrate-derived materials, preferably in a 1:6 to 1:1, water:oil weight ratio. The ethyl acetate-soluble fraction is then further extracted with an aqueous metal bicarbonate solution, preferably an aqueous sodium bicarbonate solution, at 5% by weight. The pH of the bicarbonate extraction solution is preferably maintained at approximately 8-9.5, and a 6:1 to 0.5:1 bicarbonate solution:oil weight ratio is preferably utilized. The aqueous bicarbonate layer extracts the strong organic acids and highly polar compounds, and the remaining ethyl acetate-soluble layer contains the phenolic compounds-containing/neutral fractions. This ethyl acetate-soluble layer is then separated, and the ethyl acetate solvent is evaporated using any known evaporation technique, including vacuum evaporation techniques. The dried phenolic compounds-containing/neutral fractions typically contains 0.5-1% of water with traces of ethyl acetate. Table II illustrates typical yields for various pine sawdust fast-pyrolysis oils and fractions of oils obtained during different test runs as well as for Douglas fir bark fast-pyrolysis oils.

TABLE II

Yields for Various Pyrolysis Oils

| Pyrolysis Oil | Wt % Yields of Pyrolysis Oils Based on Dry, Char-Free Oil | | | | |
|---|---|---|---|---|---|
| | EtOAc Insol | Water Sol. | Organic Acids | Phenolics/Neut. | |
| Pine sawdust | 42.8 | 24.7 | 5.7 | 21.3$^a$ | |
| Pine sawdust | 28.2 | 39$^c$ | 6.1 | 26.7$^b$ | |
| Combined pine oil$^d$ | 22.8 | 28.9 | 6.7 | 25 | |
| Pine sawdust | 41$^e$ | 27.2 | 6.3 | 26 | |
| Douglas fir bark | 0 | 12.1 | 15 | | |
| | | | | Phenolics | Neutrals |
| | | | Solids: 2.9 | 47.8 | 15.6 |
| Douglas fir bark | 0 | ND* | 19 | | |
| | | | | Phenolics | Neutrals |
| | | | Solids: 4.8 | 50.8 | 17 |

$^a$Phenolics: 16.5; Neutrals: 6.0
$^b$Phenolics: 16.5; Neutrals: 9.5
$^c$Water solubles by differences
$^d$From two condensers
$^e$EtOAc insolubles by difference
*Not Determined As indicated in Table II, the aqueous alkali metal bicarbonate solution utilized to extract strong organic acids and highly polar compounds further purifies the P/N product. While any suitable alkali metal bicarbonate solution may be utilized, the preferred solution is selected from sodium bicarbonate, potassium bicarbonate, lithium bicarbonate and ammonium bicarbonate, with sodium bicarbonate being the most preferred and most optimal solution. From the aqueous bicarbonate solution, it is possible to isolate a fraction rich in organic acids as a by-product. In this instance, the aqueous layer can be neutralized, for example with 50% by weight of phosphoric acid (although other acids can be used) saturated with sodium chloride, and extracted with ethyl acetate. It is possible to then evaporate the solvents and isolate the remaining fractions as well.

The P/N can be further fractionated into isolated phenolics and neutrals if desired. This can be accomplished by utilizing a 5% by weight solution of sodium hydroxide in a volume ratio of 5:1 of solution:extract. The aqueous layer is then acidified to a pH of about 2 utilizing a 50% solution of phosphoric acid (although other acids can be used.) It is then saturated with sodium chloride and extracted with ethyl acetate. Evaporation of the solvent leads to the isolation of the phenolics fraction; evaporation of the initial ethyl acetate solution freed from phenolics leads to the neutrals fraction. It should be noted, however, that the present invention does not require this separation of the phenolics from the neutral fractions, and it is in fact this aspect of the present invention which makes the present process so economic. In the past, as previously indicated, the phenolics have always been the desired end-product, and sodium hydroxide has typically been utilized in such process treatment. This is unnecessary with the process of the present invention, for it has been discovered that the combined phenolic compounds-containing/neutral fractions is sufficiently reactive to function by itself in the formation of adhesive resins.

The process of the present invention can be operated in both batch mode as well as in a continuous mode. In the batch mode embodiment, the whole oils are extracted with ethyl acetate and then washed with water. Following the water wash, the composition is then washed with the aqueous sodium bicarbonate to eliminate the acidic components, which come from pyrolysis of the carbohydrate fraction and would be deleterious to the resins. In a continuous operation, the pyrolysis oil is preferably extracted simultaneously with water and ethyl acetate, and then the ethyl acetate's soluble fraction is extracted countercurrently with the aqueous bicarbonate solution. The whole ethyl acetate fraction, which includes both phenolic and neutrals compounds, is then utilized as a feedstock for resins after solvent evaporation.

In the above discussion, the neutralization was performed on the ethyl-acetate-soluble fraction of the pyrolysis oils after they had been washed with water to remove the water-soluble fraction. This was expected to minimize the amount of sodium bicarbonate needed to neutralize the ethyl acetate soluble fraction, since the water-soluble organic acids would have been previously removed. However, in actual practice, a considerable excess of sodium bicarbonate solution over that required for neutralization was generally used. In addition, the low solubility of sodium bicarbonate in water required the addition of a large amount of water to the overall process. Since the neutralization of the strong organic acids with sodium bicarbonate evolves a considerable amount of carbon dioxide gas, unacceptably large amounts of ethyl acetate solvent were projected to be lost from the organic phase into the escaping carbon dioxide, unless refrigeration were to be added to the process to condense and recover the solvent.

In a commercial pyrolysis operation, steam or a noncondensible gas can be used as the gas to entrain or carry the biomass feed into the pyrolysis reactor. If steam is used as the carrier gas, the recovery of the volatile fractions of the pyrolysis vapors is enhanced because the carrier gas condenses to concentrate the remaining volatiles. When the steam condenses with the pyrolysis products, the water needed for the extraction is already present. Thus, the addition of more water with the sodium bicarbonate solution adds an unnecessary amount of water to the process. It will be shown that pyrolysis products from a variety of lignocellulosic species can be pyrolyzed in the presence of steam as well as in the presence of nitrogen as carrier gases, to produce a similar extracted product of good quality. It also follows that other noncondensible gases, such as pyrolysis gases, which contain some pyrolysis steam derived from the lignocellulosic materials, is a very suitable carrier gas for the fast pyrolysis.

The fast pyrolysis of lignocellulosic materials may be accomplished in a number of ways, which will be apparent to those skilled in the art. The examples of the invention employ a vortex reactor. However, other fast pyrolysis reactors such as, but not limited to, fluidized beds (principally, but not limited to, shallow bed) reactors, entrained flow reactors, and vacuum pyrolyzers, may be used, and these are described in the references above.

For example, it is shown that the neutralization of the whole oil prior to the extraction step is feasible. It is particularly advantageous for the ethyl acetate not to be present before the neutralization, since it avoids the loss of ethyl acetate solvent in the evolved carbon dioxide. However, in those cases where some ethyl acetate is needed to mobilize the organic fraction, minimizing the percentage of ethyl acetate present also minimizes the losses of ethyl acetate. Through the use of dry sodium bicarbonate rather than a 5% aqueous solution, the amount of sodium bicarbonate for neutralizing and the amount of water used for extraction can be decoupled to be two independent variables, which can then be separately optimized. In actual practice, this allows for a large reduction in the amount of water added to the process, which in turn reduces the amount of organically contaminated waste water for disposal in an environmentally acceptable way. Thus, the use of dry sodium bicarbonate has certain advantages over the use of a 5% aqueous solution of the same.

In an integrated, commercial application, the aqueous phase containing the neutralized organic acids and other water soluble organics, may be incinerated in a furnace. This would both dispose of the contaminated water, as well as recover the sodium bicarbonate. However, from such a furnace, it is well known that the sodium salt recovered is soda ash (sodium carbonate) rather than sodium bicarbonate. An additional process step is required to convert the recovered sodium carbonate to sodium bicarbonate, i.e. carbon dioxide gas is bubbled through an aqueous solution of sodium carbonate. This additional step is expensive as evidenced by the fact that the commercial value of sodium bicarbonate is about three times that of sodium carbonate. This bicarbonate process requires the addition of a large amount of water to form the aqueous solution, due to the relatively small solubility of sodium bicarbonate in water. As discussed above, this additional water is detrimental to the operability of the process. In addition to being cheaper, only half as much sodium carbonate is required to neutralize a given amount of acidic material compared to sodium bicarbonate on a molar basis (0.63 times less on a weight basis). Coupled with the lower cost per pound of sodium carbonate, this lowers the cost of the raw materials by a factor of 5 to neutralize with sodium carbonate rather than sodium bicarbonate.

Therefore, it would be advantageous to be able to use the cheaper sodium carbonate to neutralize the pyrolysis condensates. However, the pH of aqueous sodium carbonate is much higher at 11.6, as compared to that of sodium bicarbonate at only 8.4. It would be expected by those skilled in the art, that some of the phenolic constituents of the pyrolysis condensates would react with the sodium carbonate to form sodium phenolates, which are water soluble and therefore would not be as well extracted into the ethyl acetate solvent phase. In addition, base-catalyzed condensation reactions, that are not advantageous, could take place at a higher pH, thus altering the proportion of low and high-molecular weight phenolic products in the material.

However, it has been found that by slowly adding dry, basic sodium carbonate to the acidic pyrolysis condensates until only a pH of about 7 is reached, the phenolic constituents are still primarily extracted into the organic solvent phase, rather than forming the water-soluble phenolates. This unexpected observation allows the use of the more basic sodium carbonate, or other basic materials that may be advantageous to replace the sodium bicarbonate in the neutralization process, which result in a significant cost savings or other advantages.

EXAMPLE I 1.0 kg of fast-pyrolysis oil derived from pine sawdust was dissolved into 1 kg of ethyl acetate. After filtration of the solution, this solution is then separated into two easily identified and separated phases. The ethyl acetate-soluble phase was then isolated, and 0.8 kg of water was added to this phase. The resulting water-soluble fraction was isolated and saved for further processing. 2 kg of 5% sodium bicarbonate solution was then added to the ethyl acetate-soluble fraction, and the aqueous phase therefrom was saved for further processing. This aqueous phase contained the acids fraction. The resulting washed ethyl acetate-soluble solution, containing the P/N product was then solvent evaporated to remove the ethyl acetate solvent. The yield of P/N product was 31% by weight based on the amount of dry oil.

The remaining ethyl acetate-insoluble fraction was solvent evaporated and yielded 23 weight percent of the starting dry oil. The aqueous wash yield after solvent evaporation was 39 weight percent of the oil. The aqueous bicarbonate solution was neutralized with a 50% phosphoric acid solution, and after saturation with sodium chloride, the organic phase was extracted into ethyl acetate. After solvent evaporation, the acids fraction yield was approximately 7 weight percent. FIG. 1 illustrates this mass balance of the various fractions resulting from this Example I utilizing the process of the invention.

EXAMPLE II 9.5 kg of fast-pyrolysis oils derived from pine sawdust were dissolved into 10 kg of ethyl acetate. After filtration, this solution settled into two easily identified and separated phases. 1.8 kg of water was then added to the ethyl acetate soluble phase, and this solution was then separated into two easily identified and separated phases. The resulting water soluble fraction was saved for further processing, and the other ethyl acetate-soluble fraction was then admixed with 8.9 kg of a 5% sodium bicarbonate solution. The aqueous phase of this solution was then separated and saved for further processing, which was the acids-soluble fraction. The resulting washed ethyl acetate-soluble solution, containing the P/N product, was separated, and the solvent was then evaporated. The yield of the P/N product was 30% by weight based on dry oil.

Using a procedure similar to that described above in Example I, the mass balance of the fractionation was determined as follows: the ethyl acetate insoluble fraction comprises 21 weight percent, the water-soluble fraction comprises 31 weight percent, and the organic acids comprise 7.2 weight percent.

EXAMPLE III

The fractionation of Douglas fir bark pyrolysis products which are solids at room temperature, was similar to that described for pine. 4.6 kg of Douglas fir bark fast-pyrolysis product were dissolved into 9.8 kg of ethyl acetate solution. No ethyl acetate insoluble fraction was observed. The whole solution was then extracted with 12 kg of a 5 weight percent aqueous sodium bicarbonate solution. The ethyl acetate-soluble solution contained 68 weight percent of the bark product as phenolics and neutrals. The P/N was then separated by extraction with 11 kg of a 5 weight percent aqueous solution of sodium hydroxide. From the ethyl acetate solution, 17 weight percent percent of neutrals were obtained. The alkaline aqueous solution, containing the phenolics, was acidified with 50% phosphoric acid, although other acids could have been used. This solution was then saturated with sodium chloride and extracted with ethyl acetate to yield 50.8 weight percent for the phenolics fraction upon solvent evaporation. In the extraction with aqueous bicarbonate solution, a precipitate was formed (5 weight percent) along with the soluble acids fraction of 19 weight percent. The data for the fractionated materials are provided in Table II above.

EXAMPLE IV

Fast-pyrolysis oil derived from pine sawdust was also fractionated on a continuous basis. This continuous process utilized, but is not limited to, a 6-stage system of mixing and settling tanks. The oil, ethyl acetate, and water were mixed and allowed to settle with the organic phase being sent on to multi-stage extraction with 5 weight percent aqueous sodium bicarbonate solution with each extraction stage having a separate settling tank. The bicarbonate extraction was run countercurrent to the flow of the organic phase. The aqueous fractions, that is the combined ethyl acetate insoluble and water-soluble fractions, the aqueous bicarbonate solution, and the organic phase were all collected and processed as described above. Conditions of the extraction included the following: oil flow, water flow, ethyl acetate flow, and aqueous bicarbonate flow rates were 10, 6, 34, and 35 ml/min, respectively. It should be noted, however, that the countercurrent continuous extraction process is not limited to these flow rates. The yield of the P/N product was about 20% based on the oil flow rate. A total of 20 kg of oil was fractionated in this way. Variations in flow rates and number of settling and mixing tanks, however, can yield different proportions of materials. Phase separation was readily accomplished within the settlers.

Analysis of the products from intermediate stages of extraction revealed that 1-3 stages of bicarbonate extraction may be used. Turning from the Examples given above, the fractionation scheme described above allowed the isolation of 21% to 31% of the starting pine oils P/N products, or overall yields of 12-21% based on starting dry wood. This fraction consisted of approximately 73% phenolics, extractable from sodium hydroxide solution from an ethyl acetate solution, and 27% neutrals. The total yield of P/N product is reproducible as shown by the runs in Table II above.

It will be shown in the Examples V-IX that pyrolysis products from a variety of lignocellulosic species can be pyrolyzed in the presence of steam as well as in the presence of nitrogen as carrier gases, to produce a similar extracted product of good quality. It also follows that other noncondensible gases, such as pyrolysis gases, which contain some pyrolysis steam derived from the lignocellulosic materials, is a suitable carrier gas for the fast pyrolysis.

The fast pyrolysis of lignocellulosic materials may be accomplished in a number of ways, which will be apparent to those skilled in the art. Examples I-XI employ a vortex reactor. Other fast pyrolysis reactors such as, but not limited to, fluidized beds (principally, but not limited to, shallow bed) reactors, entrained flow reactors, and vacuum pyrolyzers, are described in the references above.

In the following example, it is shown that the neutralization of the whole oil prior to the extraction step results in an equal or better product than those described in previous Examples I to IV. It is particularly advantageous for the ethyl acetate not to be present before the neutralization, since it avoids the loss of ethyl acetate solvent in the evolved carbon dioxide. However, in those cases where some ethyl acetate is needed to mobilize the organic fraction, minimizing the percentage of ethyl acetate present also minimizes the losses of ethyl acetate. Through the use of dry sodium bicarbonate rather than a 5% aqueous solution, the amount of sodium bicarbonate for neutralizing and the amount of water used for extraction can be decoupled to be two independent variables, which can then be separately optimized. In actual practice, this allows for a large reduction in the amount of water added to the process, which in turn reduces the amount of organically contaminated waste water for disposal in an environmentally acceptable way. Thus, the use of dry sodium bicarbonate has certain advantages over the use of a aqueous solution of the same.

EXAMPLE V

Using 24 kg of dry, Colorado pine sawdust as feed for the fast pyrolysis, a vortex reactor with steam as the carrier gas, at a steam-to-biomass ratio of 1.5, 60.2 kg of pyrolysis condensates (including water of pyrolysis and steam used before, during and after the run) were prepared, which had both an aqueous and an organic phase. The average measured temperature of the carrier steam was 700° C. at 98 psia, upstream of the supersonic nozzle in the ejector. The average measured temperatures of the vortex reactor wall were 610° C. in the first third, 608° C. in the middle third and 626° C. in the last third of the reactor. Immediately downstream of the vortex pyrolysis reactor was a char cyclone, followed by a long, heated transfer tube (the process stream had a gaseous residence time of about 0.4 seconds in this tube), a second char cyclone, and a first condenser. The average measured temperatures of the pyrolysis process stream at the entrance to the transfer line and at the six equally spaced locations down the transfer line were 493°, 544°, 526°, 502°, 489°, 496°, and 495° C.

To remove the residual organic phase from the condensate collection equipment, 1 kg of ethyl acetate was used (the weight of the wash ethyl acetate is included in the condensate weight). These condensates were similar to those used in Example IV, but also included the condensed carrier steam. The organic phase was relatively viscous and could coat the glass membrane of the pH electrodes, and thus cause erroneous pH measurements. The aqueous phase (56.2 kg) was decanted and slowly neutralized by the addition of 2.2 kg of dry, solid sodium bicarbonate until an indicated pH of 6.8 was reached. This avoided the fouling tendencies of the pH electrode by the organic phase during the addition of the sodium bicarbonate. The neutralized aqueous material was mixed overnight, at which time the measured pH had risen to 7.5 (due to the loss of dissolved carbon dioxide). The organic phase was dissolved in 5 kg of ethyl acetate to facilitate transfer from its container to the mixer. The organic solution was then mixed into the previously neutralized aqueous phase to result in a slightly lowered pH of 7.3, and rose to 7.4 after mixing overnight. Thus, the previously neutralized aqueous phase solution was used to neutralize the small amount of acidity present in the organic phase. This minimized the loss of ethyl acetate in the evolved carbon dioxide. No significant formation of an organic precipitate was reported during the neutralization and extraction sequence.

The extraction of the P/N could have been accomplished in any of a number of ways known to those skilled in the art, but in this case, the neutralized, two-phase suspension was then metered into a liquid extraction system having counter-current flow through three mixer-settlers in series. Each mixer had a volume of 250 ml and each settler had a volume of 3000 ml. The neutralized feed was fed at 50 ml per minute and the ethyl acetate solvent was fed at 35 ml per minute, although these rates are not meant to be limiting. The P/N materials were extracted into the organic phase with the use of 0.7 volume of ethyl acetate per volume of mixed-phase neutralized condensates. A total of 2.6 kg of ethyl acetate was used per kg of dry wood feed. The ethyl acetate was evaporated from the organic phase to result in about the same yield of P/N material as was obtained in Example IV, namely, 0.17 kg P/N per kg dry wood feed.

EXAMPLE VI

Sixty-nine kg of pyrolysis condensates (including water) were formed by the fast pyrolysis of 27 kg of dry Colorado pine sawdust in the vortex reactor using steam as the carrier gas at a steam-to-dry-sawdust ratio of 1.2 to 1.8 and at a sawdust feeding rate of 11 to 16 kg per hour. The steam was at 88 psia and 700° C. prior to expansion through the supersonic orifice of the ejector at the entrance of the vortex reactor. The walls of the vortex reactor were at a nominal 625° C. to result in an average pyrolysis stream exit temperature of 530° C. In the transfer line between the two char cyclones, the average measured gas temperature at the entrance and at six equally spaced locations were 498°, 520°, 527°, 500°, 490°, 463°, and 455° C., respectively. The gas phase residence time in the transfer line was about 0.4 seconds.

To aid in equipment cleanup 4 kg of ethyl acetate were added. An additional 9 kg of ethyl acetate was added to transfer the organic phase into the mixer for neutralization. For neutralization, 1.5 kg of dry sodium carbonate was added to the two-phase suspension to result in an initial pH of 6.8. After two days, the pH had dropped to 6.2 and an additional 0.1 kg of sodium carbonate was added to result in the final pH of 6.8. Care was taken during the neutralization to keep the pH electrode clean and the calibration was checked after each use. The amount of solid precipitate was 0.026 kg per kg of sawdust fed. Although any of several well known methods of extraction could have been utilized, this neutralized material was then extracted in the three-stage counter current extraction system described in Example V. The total weight of ethyl acetate used was 3.0 kg per kg of dry wood fed. The yield of P/N material was 21% by weight of the feed, higher than that obtained in Example V, but similar to yields obtained in batch mode operation.

EXAMPLE VII

Using 125 kg of Southern pine sawdust, 258 kg of pyrolysis condensates (including water) were produced using steam as the carrier gas at 1 to 1.1 kg steam per kg of dry sawdust in the vortex pyrolysis reactor. The feed rate was 18 to 20 kg dry feed per hour. The pyrolysis temperatures were as in the above examples, except that the average measured temperature of the pyrolysis stream at the exit of the vortex reactor was 500° C. (standard deviation of 11° C.) and in the transfer line, between the primary and secondary char cyclones, the average measured temperature at eight locations was 438° C. To more completely recover the condensed material from the equipment, 11.9 kg of ethyl acetate was used.

Two samples were made from the condensates produced. The first sample contained 87 kg of condensates. The aqueous phase was decanted and neutralized to a pH of 7.4 from an initial pH of 2.7 with 1.8 kg dry sodium carbonate. To the organic phase, 28.5 kg of ethyl acetate was added to make a very low viscosity solution. This solution was then added to the previously neutralized aqueous phase to make the two-phase suspension to feed to the continuous flow, countercurrent extraction system. After mixing the two phases together, a significant amount of solid precipitate formed, which was skimmed off from the top of the suspension. Although, the extraction could be carried out in any of several manners, in this case, the extraction system consisted of three mixer/settlers in series, with the mixers having a volume of 750 ml and the settlers having a volume of 3000 ml. The feed rates were 300 ml per minute for the neutralized feed and 210 ml per minute for the ethyl acetate, although one skilled in the art recognizes that one could vary these rates considerably and still obtain a usable product.

The second sample of 179 kg of pyrolysis condensates (including water) was mixed with 63 kg of ethyl acetate to keep the organic phase fluid and easily suspended in the mixer. This two-phase suspension was then neutralized from an initial pH of 2.9 to a final pH of 6.8 by the addition of 4.0 kg of sodium carbonate. At this time a solid precipitate floated to the top of the suspension, where it was skimmed off. The amount of precipitate recovered from the second sample of this example was judged to be proportionately similar to that observed in the first sample. Thus, demonstrating that the order of neutralization relative to the addition of ethyl acetate did not have a marked effect on the preparation of the condensates for extraction nor on the formation of the solid precipitate, which must be removed prior to extraction to avoid operational problems. The recovered precipitate was found to be about 6 wt % of the sawdust feed.

Although any number of different methods could have been used to contact the neutralized suspension in countercurrent flow with ethyl acetate solvent, a three-stage mixer/settler system was used having the same dimensions and nominal flow rates noted for the other sample described above in this example.

The organic phase was mixed with that from several other batches to result in an average yield of P/N product of 0.19 kg per kg of dry feed.

EXAMPLE VIII

Using steam as the carrier gas in the vortex pyrolysis reactor, 35 kg of dry Southern pine sawdust was pyrolyzed to produce 77 kg of condensates (including water). The carrier gas to sawdust weight ratio was 1.2 at a sawdust feeding rate of 16 kg per hour. The average steam temperature was 690° C. measured upstream of the ejector nozzle at 90 psia. The average temperatures measured in the vortex reactor wall were 570° C. in the first third, 600° C. in the middle third, and 630° C. in the last third. The measured average temperature of the pyrolysis process stream as it exited the vortex reactor was 495° C. with a standard deviation of 4° C. (for 128 measurements). The transfer line between the primary char cyclone and the secondary char cyclone was heated and the average measured temperatures of the pyrolysis stream were 505° C. (128 measurements at each of 6 axial locations with a standard deviation of 23° C.) with a calculated residence time of 0.4 seconds. However, since chemical kinetics are exponential with temperature, it is important to recognize that it is the instantaneous temperatures of the pyrolysis process stream, not the overall average temperature, that are important. The average temperatures at the exit of the vortex reactor, the transfer line entrance, and the six equally spaced locations of the transfer line itself were 500°, 485°, 525°, 530°, 515°, 505°, 490°, and 477° C. respectively.

A 49 kg sample of the mixed suspension of condensates was neutralized and extracted. To aid in the transfer of the thick organic phase and to lower the viscosity of the organic phase during neutralization, 16 kg of ethyl acetate was added to the two-phase suspension prior to neutralization. To neutralize the suspension to a pH of 6.9 from the initial pH of 2.7 required 1.1 kg of sodium carbonate. Only a very small amount of solid precipitate. namely, 0.0009 kg per kg sawdust, was observed after the neutralization (about 65 times less than for Example VII). Apparently the higher process temperatures during the residence time in the heated transfer line were sufficient to achieve a thermally induced change in material, which otherwise would have produced a solid material, which would have precipitated in the extraction step. This change presumably lowered the molecular weight or otherwise made that material, which would have precipitated, more soluble in the ethyl acetate/water solvent system.

Although any number of different methods could have been used to contact the neutralized suspension in countercurrent flow with ethyl acetate solvent, a three-stage mixer/settler system was used having the same dimensions and nominal flow rates noted for Example VII.

An average yield of 19% of the P/N product was obtained.

EXAMPLE IX

In all of the above examples, the sawdust feed had been completely dried at 105° C. and was fed to the vortex reactor while still at about this temperature. This resulted in an equilibrium moisture content in the feed of less than 1%. In a commercial process, it may not be feasible to achieve this low level of moisture, although it may be desirable to do so in order to minimize both the heat required for pyrolysis and the amount of waste water for disposal. To evaluate the effect of residual moisture in the feed, the moisture in the as-received sawdust was measured and then adjusted to result in 8% moisture in the feed. To avoid moisture losses prior to pyrolysis, the feed was not preheated, but rather fed at ambient temperature into the vortex reactor. The vortex reactor was operated as in the above examples, but with 39.5 kg of Southern pine sawdust fed at a lower rate of 12.9 kg per hour and a steam-to-biomass ratio of 1.7. The heated transfer line was maintained at a very uniform, measured temperature of 500° C. within 11° C.

Although any number of different methods could have been used to contact the neutralized suspension in countercurrent flow with ethyl acetate solvent, a three-stage mixer/settler system was used having the same dimensions and nominal flow rates noted for Example VII.

An average yield of 16% of the P/N product was obtained.

EXAMPLE X

Figure 2:
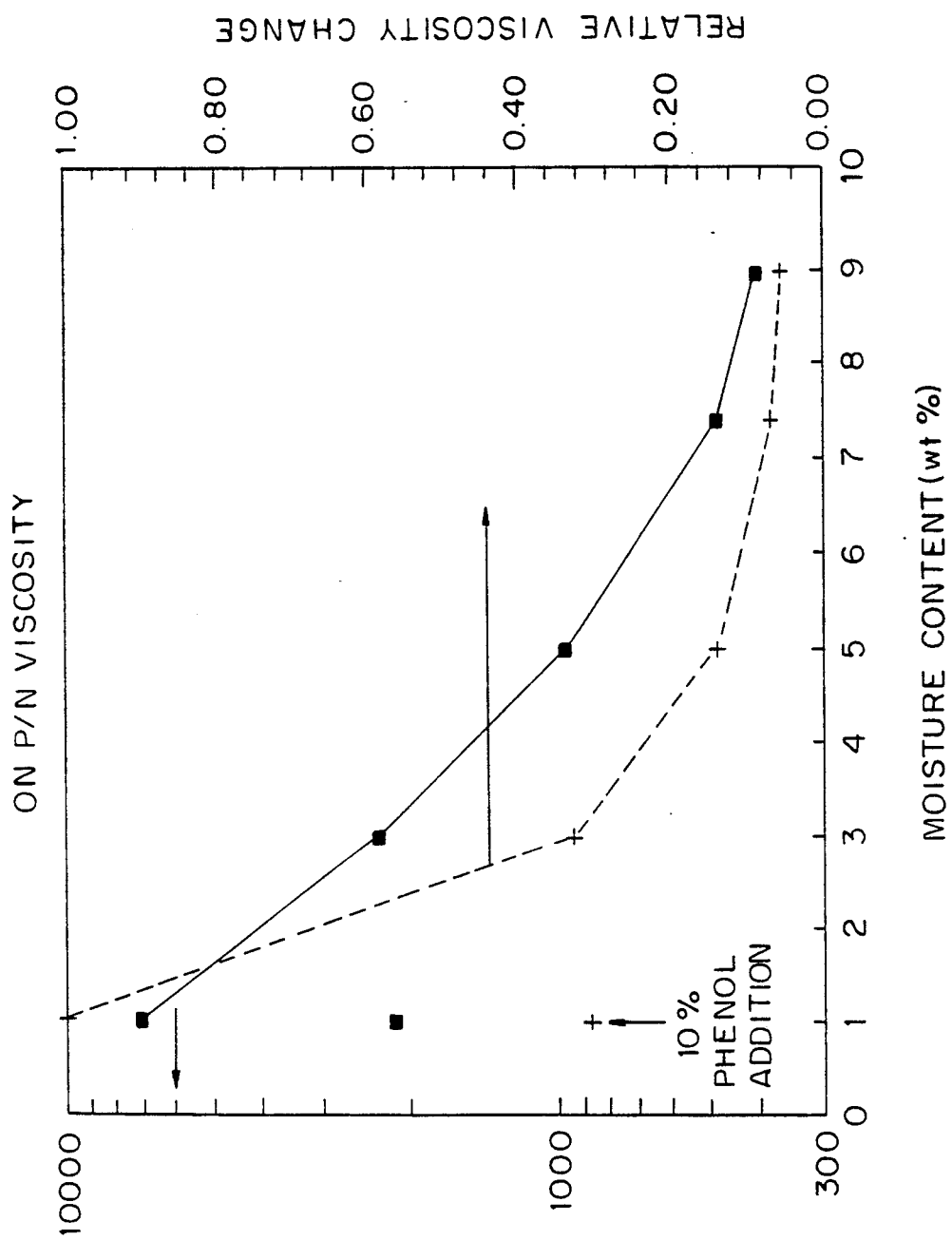
FIG. 2 illustrates the effect of addition of water to the viscosity of the phenolic compounds-containing/neutral fractions product, hereinafter to be called P/N product. Both absolute viscosity changes and relative ones are given. Also illustrated is the effect of the addition of another small molecule such as phenol, which also decreases the viscosity of the P/N product.

The economical recovery of the solvent used for the extraction is critical to the viability of the process. The recovery of the solvent from the P/N product may be accomplished by any number of processes, as long as the exposure to temperatures over 45° C. is kept to a minimum to minimize degradation of the delicate P/N product. In actual practice, we have found that the very short exposures to temperatures of 70° to 90° C. experienced in a falling film evaporator at ambient pressure have resulted in an acceptable product, when followed by a batch evaporation at 40° to 45° C. and about 70 mm Hg absolute pressure for several hours. This procedure results in a material having as low as 28% by weight ethyl acetate from the first stage of evaporation, and less than 5% residual solvent after the second stage. All of the water in the initial extract is azeotroped off by the end of the first evaporation step. It has been found to be helpful to add water between the two evaporation stages to effectively steam strip off the residual solvent as the azeotrope to result in a final solvent content of less than 1% in the P/N product. The presence of small amounts of water in the final product have a very large effect on the apparent viscosity, as shown in FIG. 2. This suggests that the commercial product could have as much as 5 to 10% water to keep the viscosity low for ease of handling. More water in the product is expected to be counterproductive, due to the cost of shipping the water in excess of that required to give a low viscosity. Since the evaporation of the ethyl acetate is endothermic, it will be advantageous to add the water in the last step as steam to directly heat the solvent laden P/N material to avoid the expense of a heat exchanger. The use of steam to directly strip the organic solvent from the P/N material replaces one solvent (water) for the other to keep the product free flowing at all times. Since the heat of condensation of steam is 4 to 5 times greater than the heat of vaporization of ethyl acetate, steam stripping the solvent from the product in the second stage of evaporation can result in the desired 5 to 10 weight, per cent water in the product, if the starting amount of ethyl acetate is about 20 to 50% in the P/N material, respectively.

The ethyl acetate, which is partially soluble in the aqueous phase of the extraction, represents a sizable potential loss in solvent, due to the relatively large amount of this phase. It has been found that the ethyl acetate can be very easily azeotroped from the aqueous phase by the direct contact with steam, although indirect heating was also effective to boil off the azeotrope from the aqueous phase. The azeotropic steam stripping left only about 0.25% ethyl acetate in the aqueous phase, when conducted with preheating of the aqueous stream and countercurrent flow of the stripping steam to the aqueous stream in a packed column.

Additional examples of preparation of the P/N product using Colorado pines, Southern pines, redwood, aspen, among other feedstocks are described. Selected examples of the preparation of the P/N products are given in Table III. The examples in this table include many variables as follows:

1) Specific pyrolysis run number; each individual pyrolysis experiment is described in more detail in Table IV;

2) Seven types of feedstock were utilized: redwood (P/N number 1), mixed Colorado pines (P/N products number 2-12), Southern pine from South Boston, Va. (P/N products 13-20, 23), Southern pine from Monticello, Ga. (P/N product 21), Southern pine from Russelville, S.C. (P/N product 22), aspen (P/N product 24), and Douglas fir bark (described in detail in Example III).

3) Neutralization mode, which consisted of aqueous sodium bicarbonate extraction or neutralization prior to ethyl acetate extraction with dry sodium bicarbonate or dry sodium carbonate;

4) Extraction type, which was either a batch, using separatory funnels, (P/N products No. 1, 2, 13, 14, and 24; the detailed preparation of these products follows that described in Examples I-II) or continuous extraction (P/N products No. 3-12, 15-23; the detailed preparation of these products follows that described in Examples IV-IX).

TABLE III

SUMMARY OF P/N PRODUCT PREPARATION AND CHARACTERIZATION FROM LIGNOCELLULOSIC FEEDSTOCKS SUBJECTED TO FAST PYROLYSIS AND SOLVENT FRACTIONATION

| P/N No. | Pyr. Run No. | Feedstock, Carrier gas | Neutr. Mode | Extn. Type | Solv. Evpn. | $H_2O$ % | EtAc % | phOH % | Phenol equiv % | Gel time sec | Comments on Resin Quality |
|---|---|---|---|---|---|---|---|---|---|---|---|
| 1 | 110 | Redwood, N2 | Aq. Bic | Batch | RV @ 45 C. | .3 | 3.8 | 7.2 | 39.6 | 285 | Low reactivity (cf. pine) |
| 2 | 82 | CO pine, N2 | Aq. Bic | Batch | RV @ 45 C. | 2 | 5 | 6.8 | 37.6 | 120 | Good melt viscosity |
| 3 | 101-2 | CO pine, N2 | Aq. Bic | C,FR1 | FF + RV @ 45 C. | .6 | 4 | 6.8 | 37.3 | 83 | Good melt viscosity |
| 4 | 108 | CO pine, steam | Dry Bic | C,FR1 | FF + RV @ 45 C. | 1 | 9 | 5.7 | 32.7 | 126 | Good melt viscosity |
| 5 | 109 | CO pine, steam | Dry Bic | C,FR1 | FF + RV @ 45 C. | 2 | 5 | 5.3 | 30.8 | 138.5 | High melt viscosity |
| 6 | 113-4 | CO pine, steam | Dry Bic | C,FR1 | FF + RV @ 45 C. | 1 | 5 | 6.7 | 36.9 | 98.5 | High melt visocisty |
| 7 | 116 | CO pine, steam | Dry Car | C,FR1 | FF + RV @ 45 C. | 5 | 1 | 6.7 | 37.3 | 132 | Soft/mush |
| 8 | 116 | CO pine, steam | Dry Car | C,FR1 | FF + RV 6% H2O | 5 | .3 | 6.1 | 34.1 | 128 | Good melt viscosity |
| 9 | 116 | CO pine, steam | Dry Car | C,FR1 | FF + RV @ 65 C. | 1.8 | 1.5 | 6.1 | 33.8 | 116 | High melt viscosity |
| 10 | 118-9 | CO pine, steam | Dry Car | C,FR1 | FF + RV @ 45 C. | 2 | 2 | 7.0 | 38.9 | 140 | Not very brittle |
| 11 | 118-9 | CO pine, steam | Dry Car | C,FR3 | FF + RV @ 45 C. | 1 | 3 | 7.1 | 40.8 | 95 | Best in brittleness |
| 12 | 118-9 | CO pine, steam | Dry Car | C,FR2 | FF + RV @ 45 C. | 1 | 1 | 7.0 | 38.9 | 128 | Hot rigidity |
| 13 | 121 | So. pine, steam | Dry Car | Batch | RV small | .9 | 5.5 | 5.9 | 32.7 | 500 | Very high viscosity |
| 14 | 127 | So. pine, steam | Dry Car | Batch | RV small | 2.2 | 3.6 | 5.8 | 32.6 | 180 | Small sample |
| 15 | 121-7 | So. pine, steam | Dry Car | C,FR6 | top RV/H2O @ 45 C. | 2.8 | 1.5 | 6.2 | 34.3 | 105 | Good flow/Less CH2O 32 sec gel time |
| 16 | 121-7 | So. pine, steam | Dry Car | C,FR6 | FF + RV/H2O @ 55 C. | 7.7 | 1.1 | 6.2 | 34.4 | 40 | Best gel times/ low yield with |
| 17 | 121-7 | So. pine, steam | Dry Car | C,FR6 | FF + RV/H2O @ 55 C. | 7.7 | 1.1 | 6.2 | 34.4 | 35 | current method. |
| 18 | 121-7 | So. pine, steam | Dry Car | C,FR6 | FF + RV/H2O @ 55 C. | 4.2 | 2 | 6.2 | 34.4 | 31.5 | Identical to master batch |
| 19 | 121-7 | So. pine, steam South Boston | Dry Car | C,FR6 | FF + RV/H2O @ 55 C. | 5.9 | 1.9 | 6.2 | 34.4 | 31.5 | Identical to master batch |
| 20 | 121-7 | So. pine, steam South Boston | Dry Car | C,FR6 | top FF + WE | .2 | .5 | 6.7 | 37.0 | 168 | Very high viscosity |
| 21 | 131 | So. pine, steam Monticello | Dry Car | C,FR6 | FF + RV/H2O @ 55 C. | 5.6 | 1.7 | 5.9 | 32.6 | 49 | Excellent flow Good hot rigidity |
| 22 | 132 | So. pine, steam Russelville | Dry Car | C,FR6 | FF + RV/H2O @ 55 C. | 3.3 | 0.3 | 5.9 | 32.6 | 53 | Extremely good flow Poor hot rigidity |
| 23 | 133 | So. pine, steam South Boston, wet | Dry Car | C,FR6 | FF + RV/H2O @ 55 C. | 4.9 | 2 | 5.9 | 32.6 | 30 | Good flow Good flow rigidity |
| 24 | 84 | Aspen, N2 | Aq. Bic | Batch | RV @ 45 C. | .9 | 7.5 | 7.5 | 41.9 | 80 | Good flow |

TABLE III-continued

SUMMARY OF P/N PRODUCT PREPARATION AND CHARACTERIZATION FROM LIGNOCELLULOSIC FEEDSTOCKS SUBJECTED TO FAST PYROLYSIS AND SOLVENT FRACTIONATION

| P/N No. | Pyr. Run No. | Feedstock, Carrier gas | Neutr. Mode | Extn. Type | Solv. Evpn. | $H_2O$ % | EtAc % | phOH % | Phenol equiv % | Gel time sec | Comments on Resin Quality |
|---|---|---|---|---|---|---|---|---|---|---|---|
| | | None | — | — | — | — | — | 18.1 | 100 | 90 | Excellent |

EXPLANATIONS

Detailed Method of Preparation of the P/N Product:
Numbers 1 and 24 are described in Example I; Number 2 is described in Example II; Number 3 is described in Example IV; Number 5 is described in Example V; Numbers 7-12 are described in Example VI; Numbers 14-22 are described in Example VII; Number 13 is described in Exmaple VIII; Number 23 is described in Example IX. All samples described are prepared in a manner described by one of these detailed Examples. Summary of conditions are given in the Table II, IV, and V.
Feed: CO pine is a mixture of Colorado Pines (mainly Ponderosa and Lodgepole); Locations for the Southern pines are indicated: South Boston, VA, Monticello, GA, or Russelville, SC. The main types of Southern pines include: lobiolly, longleaf, shortleaf, and a minor species is slash. Carrier Gas: Nitrogen or steam
Run No.: Pyrolysis Run Number.
Neutralization type: Type of base added — Aq. Bic = 5% aqueous $NaHCO_3$; Dry Bic = dry $NaHCO_3$; Dry Car = dry $Na_2CO_3$; base added to lower the pH to 6.4–7.8.
Extraction Type: Batch (small amounts, hand extractions in separatory funnels); C = semicontinuous; FR1 = base case flow rate — mixing time 3 min and 30 min settling time; FR2 = mixing time 1.5 min and 15 min settling time; FR3 = mixing time 1 min and 10 min settling time; FR6 = same times of FR3 but with double the vessel size for details see Table V.
Solvent Evaporation: RV = rotary evaporation; at 45° C. or at 55° C. as the bath temperature; FF = falling film evaporator; WE = Wiped film evaporator; this sample was removed from the topmost part of the container, and was not fully mixed as were the samples labeled Xx-84. Prior to Wiped film evaporation and after evaporation, the P/N sample was heated with a heat gun for 10–15 min at about 85° C. in order to reduce viscosity and increase flow rate to transfer to containers. Sample XX-69-PN was also prepared from the topmost sample from the drum container. Samples labeled Xx-84 were homogenized prior to rotary evaporation. Lot 1 and Lot 2 refer to two of many lots that were used to make the master lot; samples from these lots were identical within the experimental error to those of the fully homogenized batch.
Water and Ethyl Acetate (EtAc) determinations by Gas Chromatography. Phenolic hydroxyl contents determined by conductimetric titration.
Phenol equivalence: phenolic OH %*(94/17)*100.
Gel time measurements on formulations that contained the following:
20–25 g oil; 18.8 g phenol (88%); 0.5 g HCl; 11.8 g of 37% Formaldehyde; anhydrous $Na_2CO_3$ 1 g; and 15 g of water. 1.25 part of resin were formulated with 0.2 parts of hexamethylenetetramine, and 0.2 parts of lime. Gel time given is the 150° C. stroke cure in seconds. Samples Xx-84 have less formaldehyde in their formulation than the other samples. These numbers are only for comparative purposes since this test is done on very small samples. The test is indicative of relative changes of the properties of the P/N products as the pyrolysis/fractionation/solvent evaporation procedure evolved.

TABLE IV

PYROLYSIS CONDITIONS

| P/N # | Run # | Recycle Loop Temp.* °C. | Reactor Exit Temp.* °C. | Reactor Pressure (in $H_2O$) | Avg. Vapor Cracker Temp.* °C. | Vapor Cracker Res. Time** seconds | Steam to Biomass Ratio | Feed Rate (kg/h) | Product Distribution Wt. % Char | % of Feed Gas | Oil |
|---|---|---|---|---|---|---|---|---|---|---|---|
| 1 | 110/$N_2$ | 351 | 463 | 40 | 407 | 0.60 | 1.74 | 14.4 | 24.2 | 10.3 | 65.5 |
| 2 | 82 | 376 | 476 | 46 | 382 | 0.71 | 1.38 | 13.0 | 16.0 | 9.7 | 74.3 |
| 3 | 101/$N_2$ | 370 | 491 | 55 | 350 | 1.01 | 2.05 | 10.0 | 16.6 | 10.7 | 72.7 |
| 3 | 102/$N_2$ | 434 | 504 | 63 | 397 | 0.84 | 2.32 | 10.0 | 17.4 | 12.2 | 70.4 |
| 4 | 108 | 447 | 496 | 61 | 451 | 0.52 | 1.28 | 17.0 | 14.0 | 10.2 | 75.8 |
| 5 | 109 | 450 | 496 | 63 | 491 | 0.40 | 1.68 | 13.0 | 9.9 | 11.8 | 78.3 |
| 6 | 113 | 463 | 527 | 63 | 443 | 0.58 | 1.84 | 11.0 | 10.0 | 16.8 | 73.2 |
| 6 | 114 | 442 | 518 | 67 | 455 | 0.57 | 1.59 | 12.7 | 10.3 | 10.2 | 79.5 |
| 7-9 | 116 | 430 | 530 | 62 | 493 | 0.43 | 1.11 | 17.5 | 12.0 | 12.0 | 76.0 |
| 10-12 | 118 | 388 | 470 | 63 | 482 | 0.43 | 1.18 | 17.0 | 15.9 | 8.9 | 75.2 |
| 10-12 | 119 | 345 | 470 | 57 | 505 | 0.42 | 1.22 | 16.6 | 15.1 | 9.8 | 75.1 |
| 15-20 (13) | 121 | 377 | 495 | 62 | 503 | 0.42 | 1.23 | 16.4 | 14.6 | 11.5 | 73.9 |
| 15-20 (14) | 127 | 386 | 498 | 74 | 413 | 0.48 | 1.25 | 20.0 | 13.5 | 14.1 | 72.4 |
| 15-20 | 122 | 368 | 510 | 70 | 438 | 0.57 | 1.25 | 16.0 | 13.1 | 13.6 | 73.3 |
| 15-20 | 123 | 358 | 491 | 67 | 428 | 0.58 | 1.20 | 16.7 | 14.2 | 10.4 | 75.4 |
| 15-20 | 124 | 363 | 484 | 65 | 442 | 0.55 | 0.83 | 24.0 | 14.9 | 9.0 | 76.1 |
| 15-20 | 125 | 363 | 489 | 64 | 440 | 0.55 | 0.88 | 22.6 | 15.1 | 11.3 | 73.6 |
| 15-20 | 126 | 385 | 500 | 71 | 415 | 0.45 | 1.53 | 17.6 | 13.4 | 14.2 | 72.4 |
| 21 | 131 | 410 | 520 | 55 | 497 | 0.49 | 1.09 | 19.7 | 13.7 | 12.6 | 73.8 |
| 22 | 132 | 409 | 490 | 80 | 492 | 0.49 | 1.11 | 19.2 | 14.6 | 18.2 | 67.2 |
| 23 | 133 | 415 | 500 | 75 | 500 | 0.50 | 1.66 | 12.9 | 15.1 | 17.1 | 67.8 |
| 24 | 84/$N_2$ | 390 | 508 | 53 | 397 | 0.82 | 1.83 | 12.3 | 12.0 | 16.0 | 72.0 |
| — | 130 | 420 | 530 | 89 | 506 | 0.41 | 0.97 | 20.2 | 15.7 | 12.2 | 72.1 |

The continuous method used batch neutralization followed by continuous extraction in a series of mixing and settling tanks (5 for Example IV, 3 for Examples V-IX) with continuous flow of organic solution and ethyl acetate extractant in a countercurrent way. Mixers had 250 (Example IV-VI) or 750 ml (Examples VII-IX) of volume, whereas the settlers had volumes of 3000 ml, for these examples. Common successful conditions were flow rates of 300 ml/min of the neutralized feed and 210 ml/min of the ethyl acetate. Overall the material balance for the various extractions was >95%. Equilibrium in this system is achieved quickly, i.e., within 0.5 to 1 minute mixing time, the yields of extraction are identical to those one obtains by increasing the mixing times to 4 to 5 minutes. For 1 minute mixing times with this equipment, settling times of 1, 3, and 5 minutes respectively, were observed for the combinations of mixer/settler numbers 1 (solvent entrance), 2, and 3 (feed entrance). Because the equilibrium is achieved very rapidly, a number of conventional extraction procedures can be employed to prepare the P/N product. Specific details of extraction conditions and yields are given in Table V.

5) Mode of solvent (ethyl acetate) evaporation. Rotary evaporation (RV) was one method used, with the bath at the specific temperature indicated in the table. In addition to RV, two methods were tested in conjunction with RV or alone. For instance, a falling film evaporator was used in conjunction with RV and a wiped film evaporator was tested on its own to drive off most of the ethyl acetate. In order to reduce the amount of residual ethyl acetate in rotoevaporation, it was found advantageous to add water to the evaporating P/N fraction so that the azeotrope of water/ethyl acetate is evaporated at a fixed pressure A very low residual amount of ethyl acetate remaining in the P/N product is thus obtained. For instance, from a 25-50% by weight ethyl acetate in the P/N product, produced in the falling film evaporator (used in conjunction with the continuous solvent extraction), the solution was rotoevaporated at 45° C. (bath pressure to 20 mmHg for 45 min. This method produced P/N products with 1-6% residual ethyl acetate.

changed from steam to nitrogen. For instance, bark derived phenolic products have phenolic hydroxyl group contents of 7.4-11.5% on going from steam to nitrogen in the pyrolysis. These higher phenolic hydroxyl contents make bark-derived P/N products or the isolated phenolic product (see Table II) very attractive for replacement of phenol in phenol-formaldehyde thermosetting resins. Note that P/N products from wood do not exhibit the same effect (see Table III) on pheno-

TABLE V

SUMMARY OF NEUTRALIZATION AND EXTRACTION CONDITIONS
Values Given are Net per kg Dry Wood Fed in the Pyrolysis Run

| P/N No. | RUN | DRY WOOD FED kg | Neat Condensates* kg | BASE[8] kg | WASH EA. kg | TOTAL EA. kg | P/N kg | SOLID PPT. kg | BASE[8] gew | FINAL pH |
|---|---|---|---|---|---|---|---|---|---|---|
| 1 | 110 | RW 19.4 | 0.54[6] | — | 0.038 | ND | 0.15 | — | | |
| 2 | 82 | CP 24.7 | 0.63[6] | — | — | ND | 0.15 | — | | |
| 3 | 101 | CP 23.6 | 0.55[2] | 0.049 BCS | — | 1.52 | 0.08[5] | — | 0.58 | |
| 3 | 102 | CP 14.5 | 0.66[2] | 0.096 BCS | — | 1.90 | 0.10[7] | — | 1.14 | |
| 4 | 108 | CP 32.3[1] | 1.99 | excess DBC | 0.383 | 2.55 | 0.17 | — | — | |
| 5 | 109 | CP 24.7 | 2.47 | 0.089 DBC | 0.244 | 2.56 | 0.18 | 0.019 | 1.06[10] | 7.4 |
| 6 | 113 + 114 | CP 56.5 | 2.58 | 0.082 DBC | 0.208 | 2.54 | 0.21 | 0.026 | 0.98[10] | 6.8 |
| 7-8-9 | 116 | CP 26.9 | 2.57 | 0.059 DC | 0.479 | 2.97 | 0.20 | — | 0.95 | |
| 10 | 118 + 119 | CP 65.3[1] | 2.08 | 0.054 DC | 0.483 | 1.60 | | | 0.87 | 7.4 |
| 13-19 | 121[1] | SP1 25.8[1][3] | 1.89 | 0.042 DC | 0.717 | 1.77 | 0.19 | 0.0008 | 0.68 | 6.9 |
| 13-19 | 122 | SP1 78.4 | 1.96 | 0.050 DC | 0.427 | 2.34 | 0.19 | 0.069 | 0.81 | 6.8 |
| 13-19 | 123 | SP1 30.9 | 2.63 | 0.055 DC | 0.510 | 2.39 | 0.19 | 0.031 | 0.89 | 7.3 |
| 13-19 | 124 | SP1 32.4 | 2.38 | 0.054 DC | 1.106 | 3.05 | 0.19 | 0.024 | 0.87 | 6.4 |
| 13-19 | 125 | SP1 116.8 | 2.11 | 0.053 DC | 0.562 | 1.82 | 0.19 | 0.050 | 0.86 | 6.9/6.5 |
| 13-19 | 126 | SP1 124.8 | 2.07 | 0.046 DC | 0.804 | 2.55 | 0.19 | 0.045 | 0.74 | 6.8/7.4 |
| 13-19 | 127 | SP1 119.8[3] | 2.02 | 0.057 DC | 0.860 | 2.45 | 0.19 | 0.044 | 0.92 | 7.4 |
| 20 | 130 | SP1 59.4 | 2.17[92] | 0.082 DC | 1.102 | 2.90 | ND | 0.032 | 1.32 | 7.15 |
| 21 | 131 | SP2 43.7 | 1.94 | 0.074 DC | 0.699 | 2.34 | 0.18 | 0.046 | 1.19 | 7.4 |
| 22 | 132 | SP3 32.3 | 1.97 | 0.076 DC | 0.789 | 2.62 | 0.18 | 0.028 | 1.23 | 7.5 |
| 23 | 133 | SP1M 39.5[1] | 2.61 | 0.090 DC | 0.939 | 3.29 | 0.16 | 0.039 | 1.45 | 7.8 |
| 24 | 84 | A 18.3 | 0.61 | — | — | — | ND | | | |

*Aqueous and Organic Condensate (not ethyl acetate)
[1]Corrected for slip stream removed for catalyst bed
[2]Extra water added
[3]Condensate samples removed, feed amount adjusted accordingly
[4]Bone dry basis, but 8% moisture in feed
[5]Oils washed excessively during extraction
[6]$N_2$ carrier gas
[7]neutralization problems
[8]15% sodiumbicarbonate solution (BCS), dry sodiumbicarbonate (DBC), dry sodium carbonate monohydrate (DC)
[9]Colorado Pine (CP); Southern Pine-South Boston, VA (SP1); Southern Pine-Montecello, GA (SP2); Southern Pine-Russelville, SC (SP3)

However, if water is added in excess and the rotary evaporation continued, for instance, at 60 mmHg and 35°-38° C. vapor temperature (or 55° C. bath temperature), the ethyl acetate/water azeotrope was evaporated and the levels of residual ethyl acetate were reduced to near or less than 1%. Example X details this procedure. Wiped film evaporation can indeed lower the residual ethyl acetate content to 0.5% or less. The yields of P/N product range from 16 to 21% of the starting dry wood weight in the pyrolysis for P/N products Numbers 4-23. These yields are assembled in Table V for the various P/N products described in Table III.

The P/N products thus produced have been characterized by a number of methods (see Table III), such as the determination of the residual amounts of water and ethyl acetate, which strongly modify their physical properties such as viscosity as shown in FIG. 2. The content of phenolic hydroxyl groups, determined through conductimetric titration, can be expressed as weight % of the P/N product or as the phenol equivalent percent. The phenolic hydroxyl content serves as a guideline for the ability of the P/N product to replace phenol, which has 18.1 wt % of phenolic hydroxyl groups. From the examples in Table III the weight percent of phenolic hydroxyl groups in the various P/N products from wood ranges from 5.6-7.2%. For Douglas fir bark (Example III) higher phenolic hydroxyl contents were observed when the carrier gas was lic hydroxyl contents on going from nitrogen to steam within the experimental error of the measurements. The suitable ranges of phenolic hydroxyl contents are thus between 5 and 12% for the P/N products or isolated phenolic products. The 5-15% is the preferred range of phenolic hydroxyl contents for phenolic products derived from fast pyrolysis of lignocellulosic materials.

These various samples were employed to prepare novolaks and gel times and comments on the physical properties of these novolaks are given in Table III.

The P/N products are also characterized by a variety of methods as follows:

Low Molecular Weight, Volatile Components

Gas chromatography—Mass spectrometric detection with a Hewlett Packard GC/Mass Spectral Detector (GC/MSD HP 5970 B) using an Ultra 2 capillary column (25 m in length by 0.20 mm internal diameter) was employed. Chromatographic conditions were linear velocity of 27 cm/s, and the following temperature program: hold at 0° C. for 2 minutes; increase the temperature to 100° C. at 5° C./min, hold for 3 min; increase the temperature to 150° C. at 3° C./min, and then increase the temperature to 300° C. at 10° C./min, hold for 15 min at 300° C. (total time 71 min) to allow maximum separation of components. Verification of peak assignments is based on the library of spectra supplied by the GC/MS manufacturer and was verified, where possible, by injection of pure samples, and by acetylation of the P/N oil to increase as much as possible the amounts of volatile materials eluted from the column. Regardless of the method used, the gas chromatographic method detects less than about 15% of the total compounds, as seen in Table VI. The calibrated compounds represent those that could be verified and calibrated by injection of pure compounds in known amounts. The uncalibrated compounds were not verified and their assignments are tentative. In particular, the absolute position of substituents is the most uncertain feature of these data. The amounts of uncalibrated products and unidentified peaks is based purely on the areas percent of these peaks, without the use of a response factor, and therefore, these numbers are approximate, and serve only as a guide for estimating amounts of volatile products present. Thus, 21 compounds have been identified and the identification of an additional 15 compounds is suggested.

Molecular-Weight Distribution of Components

High-Performance Size Exclusion Chromatography (HPSEC) was performed using a Hewlett-Packard HP1090 high performance chromatograph with an ultraviolet diode- array detector (HP1040) and a refractive index detector (HP1037) as described by Johnson, D. K. and H. L. Chum, in "Some Aspects of Pyrolysis Oils Characterization by High Performance Size Exclusion Chromatography (HPSEC)," in Chapter 15, *Pyrolysis Oils from Biomass—Producing, Analyzing and Upgrading*, edited by E. Soltes and T. Milne, ACS Symposium Series 376, pp. 156-166, 1988. An HPSEC column (Polymer Labs, PL Gel, 300×7.5 mm) of polystyrene-divinylbenzene copolymer particles (5 μm diameter) with a mean pore diameter of 50 angstroms was used; tetrahydrofuran was the eluant at a flow rate of 1 ml/min. Calibrations were made with polystyrenes and Igepals standards of known molecular weight. The weights for the P/N products are relative to these standards and are called apparent molecular weights. The P/N products have approximately 42% of components in the range of 0-250 apparent molecular weight, 25% in the 250-450 range, and 25% from 450 to several thousand. The fact that the HPSEC suggests that the P/N product has a higher amount of low molecular weight materials compared to those that elute from the gas chromatographic set up described above is not surprising, since not all these materials are volatile; they contain more polar groups than simple phenolic compounds, and are, therefore, more difficult to chromatograph under the conditions employed. From the HPSEC, for instance, monomeric, dimeric, trimeric, tetrameric, and pentameric phenolic substances are present in the P/N product. Low amounts of polymers of higher molecular weight are present in the P/N product compared to isolated lignins by aqueous or solvent methods. The products are mixtures of compounds, and the GC/MSD detects only volatile monomers and a few dimeric species under the conditions above. The acids and neutrals fractions exhibit lower molecular weight components as determined by HPSEC than the P/N product.

TABLE VI

| GC/MSD Quantities of Volatile Monomeric Products in the P/N Products from Various Lignocellulosic Feedstocks. | | | | | | |
|---|---|---|---|---|---|---|
| Compound Name (AVG WT % IN OH) | R.T. (min.) | ASPEN BIII-13-PN | REDWOOD XIX-80-PN | SO. PINE XXI-71-PN | SO. PINE XX-84-PN | CO. PINE B114-2-PN |
| CALIBRATED | | | | | | |
| Butyrolactone | 17.47 | 0.61 | 0.54 | 0.53 | 0.41 | 0.51 |
| 3-Methyl-2-Cyclopentanediene | 19.30 | | 0.03 | 0.15 | 0.12 | 0.11 |
| 3-Methyl Furnival | 19.22 | 0.05 | 0.06 | 0.08 | 0.08 | 0.08 |
| Phenol | 20.01 | 0.67 | 0.51 | 0.14 | 0.09 | 0.06 |
| o-Cresol | 22.52 | 0.08 | 0.06 | 0.09 | 0.07 | 0.06 |
| p-Cresol | 23.31 | 0.08 | 0.22 | 0.15 | 0.13 | 0.11 |
| Cusiscol | 23.86 | 0.28 | 0.50 | 0.46 | 0.55 | 0.54 |
| 2,4-Xylenol | 26.55 | 0.05 | 0.06 | 0.10 | 0.08 | 0.06 |
| Methyl Cusiscol | 28.75 | 0.18 | 0.83 | 0.43 | 0.67 | 0.70 |
| 3,4-Xylenol | 28.71 | 0.02 | | 0.03 | 0.03 | 0.04 |
| Catechol | 29.22 | 0.35 | 0.58 | 0.79 | 0.53 | 0.44 |
| Hydroquinone | 32.73 | 0.09 | 0.10 | 0.01 | 0.01 | |
| 4-Ethyl Cusiscol | 32.83 | 0.09 | 0.25 | 0.16 | 0.22 | 0.21 |
| 4-Vinyl Cusiscol | 34.51 | 0.28 | 2.49 | 1.13 | 1.45 | 1.46 |
| Syringol | 36.29 | 0.47 | | 0.03 | 0.05 | |
| Eugenol | 36.53 | 0.10 | 0.27 | 0.18 | 0.29 | 0.32 |
| 4-Propyl Cusiscol | 36.93 | 0.03 | 0.09 | 0.04 | 0.07 | 0.07 |
| Vanillin | 38.69 | 0.09 | 0.38 | 0.46 | 0.50 | 0.64 |
| Isoeugenol | 40.75 | 0.19 | 0.87 | 0.38 | 0.71 | 0.70 |
| Acetovanillone | 42.43 | 0.08 | 0.27 | 0.24 | 0.30 | 0.37 |
| Coniferyl Alcohol | 48.25 | 0.10 | 0.10 | 0.10 | 0.32 | 0.19 |
| TOTAL WT % CALIBRATED | | 3.9 | 1.0 | 5.7 | 6.7 | 6.7 |
| UNCALIBRATED | | | | | | |
| 1-Pentanol | 12.74 | 0.10 | 0.09 | 0.10 | 0.01 | 0.05 |
| 1-Acetoxy-2-Propanone | 15.82 | 0.01 | 0.02 | 0.06 | 0.06 | 0.02 |
| Ethyl Benzene | 16.41 | 0.01 | | 0.01 | | |
| 2-Methyl Furestone | 19.83 | | | 0.08 | 0.07 | 0.06 |
| 3-Methyl-1,2-Cyclopentanediene | 21.69 | 0.06 | 0.09 | 0.05 | 0.13 | 0.04 |
| 2-Methyl-1-Pentene-3-one | 22.26 | 0.02 | | 0.09 | 0.09 | 0.09 |
| 2-Ethyl-3-Methyl Phenol | 30.86 | 0.03 | 0.17 | 0.19 | 0.14 | 0.16 |
| 5-Hydroxy Methyl Futfural | 31.00 | | | 0.13 | 0.19 | 0.23 |
| 2-Methyl Pentadiene | 32.12 | 0.24 | 0.10 | 0.10 | 0.12 | 0.04 |
| 3-Methyl Catechol | 33.61 | 0.12 | 0.26 | 0.44 | 0.27 | 0.20 |
| Methoxy Proponyl Phenol | 38.85 | 0.10 | 0.21 | 0.15 | 0.19 | 0.20 |
| 1-(4-Hydroxy-3-Methoxy-Phenyl)-Propene-2-one | 43.84 | 0.09 | 0.21 | 0.17 | 0.20 | 0.21 |

TABLE VI-continued

GC/MSD Quantities of Volatile Monomeric Products in the P/N Products from Various Lignocellulosic Feedstocks.

| Compound Name (AVG WT % IN OH) | R.T. (min.) | ASPEN BIII-13-PN | REDWOOD XIX-80-PN | SO. PINE XXI-71-PN | SO. PINE XX-84-PN | CO. PINE B114-2-PN |
|---|---|---|---|---|---|---|
| 4-Hydroxy-3-Methoxy-Benzene Acetic Acid | 46.63 | 0.14 | 0.36 | 0.21 | 0.33 | 0.30 |
| (Hydroxy-Propenyl) Methoxy Phenol | 47.05 | 0.08 | 0.10 | 0.15 | 0.24 | 0.19 |
| MW 178 | 48.33 | 0.33 | 0.74 | 0.49 | 0.67 | 0.83 |
| TOTAL WT % UNCALIBRATED | | 1.3 | 2.3 | 2.4 | 2.8 | 2.6 |
| UNIDENTIFIED | | 4.8 | 2.8 | 2.9 | 4.5 | 4.9 |
| TOTAL WT % HY CC | | 9.2 | 14.2 | 14.0 | 14.0 | 14.2 |

Apparent weight-average molecular weights ($M_w$) and polydispersities (the ratio between the apparent weight-average and the number-average molecular weights) were measured for Spherogel) placed in series, with mean pore diameters of 100, 500, and 1000 angstroms (particle size 10µ). A broad bandwidth (80 nm) centered at 260 nm was used to produce the chromatographic signal that was then integrated. These columns were also calibrated as before, and conditions are the same as described above. These results are assembled in Table VII.

TABLE VII

Apparent Weight-average Molecular Weights and Polydispesities for Selected P/N Products and corresponding viscosities at 45° C.

| P/N Product # of Table III | $M_w$ | Polydispersity | Viscosity, cP |
|---|---|---|---|
| 1 | 430 | 1.5 | 77300 |
| 6 | 410 | 1.6 | 7625 |
| 11 | 460 | 1.7 | 17500 |
| 17 | 440 | 1.6 | 1710 |
| 21 | 440 | 1.7 | 5810 |
| 22 | 400 | 1.6 | 6470 |
| 23 | 420 | 1.6 | 1970 |
| 24 | 510 | 1.8 | 29800 |

Molecular-beam Mass Spectrometry (MBMS) of the P/N products

In this technique the P/N product is revolatilized directly into the sampling system of the molecular beam mass spectrometer. The equipment and the interpretation of the results are described by Evans, R. J. and T. A. Milne, in "Molecular Characterization of the Pyrolysis of Biomass. 1. Fundamentals," Energy & Fuels, Vol. 1, pp. 123-137, and "Molecular Characterization of the Pyrolysis of Biomass. 2. Applications," Energy & Fuels, Vol 1, pp. 312-319, 1987. From the molecular beam mass spectra of the P/N product, a number of phenolic compounds can be identified: guaiacol (2-methoxyphenol) m/z 124; catechols m/z 110; isomers of substituted 2-methoxyphenols with alkyl groups such as methyl (m/z 38), vinyl (m/z 150), 3-hydroxypropen(1)-yl (m/z 180), allyl (m/z 64), hydroxyethyl (m/z 168), and ethyl (152), most likely in the para position to the hydroxyl group. Carbonyl groups are also present in para position and give rise to vanillin (m/z 152), coniferyl aldehyde (m/z 178), and acetovanillone (m/z 166). Thus, from this technique, validation of the identification of a number of the compounds listed in Table VI is achieved, and the identification of very reactive compounds such as vinylphenol (m/z 120), vinyl catechol (m/z 136), vinylguaiacol (m/z 150), furfural, and 5-hydroxymethyl furfural. The latter two compounds are carbohydrate-derived. Using the standard addition method, it is possible to estimate that the Colorado pine samples (e.g., P/N product 11) contains about 4% each of 5-hydroxymethyl furfural and furfural. These two compounds are examples of neutral compounds present with the phenolic compounds in the P/N product. These compounds are difficult to detect with the gas chromatographic set up described above. Independent measurements of the furfural content by gas chromatography with a different column and protocol were 5% for a Southern pine P/N product (No. 20). Large uncertainties are associated with the quantitative method, but not with the identification procedure of the compounds with reactive aldehydic components. Reactions of these aldehyde-containing compounds will be similar to those of formaldehyde; with furfural and 5-hydroxymethylfurfural, the possibility of crosslinking with phenol exists as well.

Methoxyl Content

Methoxyl contents of the P/N products were determined by reaction of the P/N product with HI and gas chromatographic determination of the evolved methyl iodide as employed by W. G. Glasser, C. A. Barnett, P. C. Muller, and K. V. Sarkanen (The Chemistry of Several Bioconversion Lignins, J. Agricultural and Food Chemistry, vol. 31, pp. 921-930, 1983). Direct measurement of methoxyl content for Colorado pine P/N product indicates 8-9% content versus 15.0% for Ponderosa pine milled wood lignin; for a variety of conifer (softwood) lignins it ranges from 14 to 16% wt basis of lignin (see K. V. Sarkanen and H. L. Hergert, "Classification and Distribution", in Lignins—Occurrence, Formation, Structure and Reactions, edited by K. V. Sarkanen and C. H. Ludwig, Wiley- Interscience, New York, 1971, p. 55). For another softwood, redwood, the methoxyl content of the P/N product is 9-10%, similar to that for the pines. For the aspen P/N product, a content of 10-11% versus 21-22% for the starting wood (same reference above p.68). The Douglas fir bark P/N product has a very low methoxyl content (<5%). Therefore, the P/N products are characterized by a low methoxyl content relative to the methoxyl content of the lignins in the corresponding starting materials, which is a desirable property to produce a suitable replacement for phenol in phenol-formaldehyde thermosetting resins since high methoxyl content lowers the reactivity of the corresponding phenolic compounds towards formaldehyde. The methoxyl content can be tailored by the conditions of pyrolysis and post-pyrolysis thermal treatment, as they emerge from the evolving understanding of lignocellulosic biomass pyrolysis through multivariate analyses (see references of Evans and Milne above and R. J. Evans and T. A. Milne, "Mass Spectrometric Studies of the Relationship of Pyrolysis Oil Composition to Formation Mechanisms and Feedstock Composition," in *Research in Thermochemical Biomass Conversion*, edited by A. Bridgwater and J. Kuester, London: Elsevier Applied Science, pp. 264-279, 1988).

Demonstrated ranges of methoxyl contents of P/N products from a variety of lignocellulosic materials is 5-12%. The prefered ranged is 2-14%.

Taking together the functional group content analyses and the types of monomeric units that are present in these materials, and assuming an average of all types of monomers, the aromatic structure present in these molecules would have a molecular weight of 150±30, and one can then calculate the proportions of these functional groups relative to a monomeric unit. Using the average phenolic hydroxyl and methoxyl contents, respectively, of the various P/N products these contents translate into 0.5 to 0.7 phenolic hydroxyl and 0.4 to 0.5 methoxyl per aromatic unit. The corresponding numbers for conifers milled wood lignins correspond to 0.1-0.2 phenolic hydroxyl and 0.9-1 methoxyl per aromatic unit. Pyrolysis/fractionation/solvent evaporation increases substantially (by factors of 3 to 5) the free phenolic content and decreases by a factor of two the methoxyl content of the P/N product, compared to the original starting milled wood lignin.

Pyrolysis/fractionation/solvent evaporation produces a number of very reactive monomeric compounds, which have unsaturations at the side chains. These unsaturated structures can also enter into the polymerization reactions and are likely to be also present in the higher oligomeric fractions. These characteristics of the P/N product work together to make products that can be superior for use in molding compounds and adhesives in general, such as phenol-formaldehyde resole resins, compared to the use of lignins isolated from wood through pulping methods.

Spectroscopic Methods for Whole P/N Product Characterization

Figure 3:
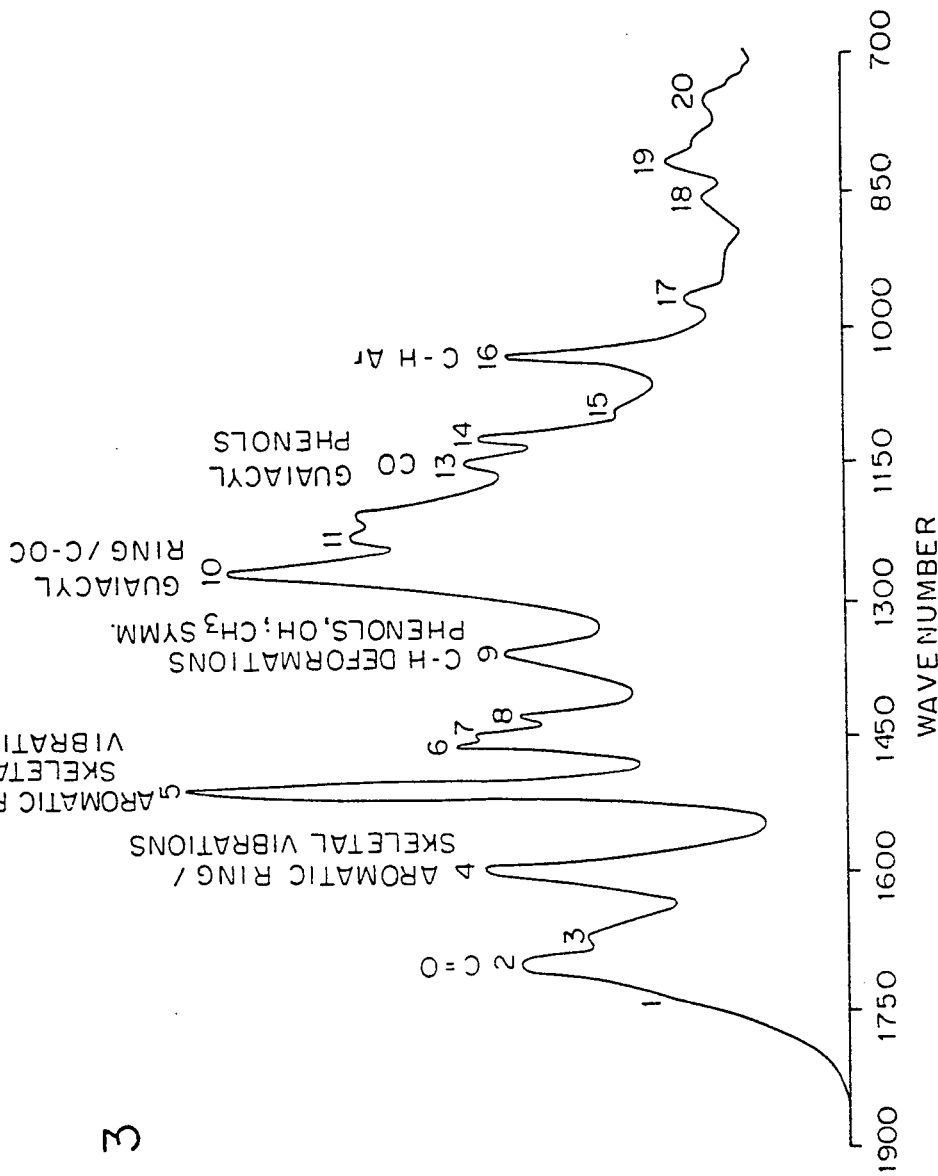
FIG. 3 illustrates the Fourier-transform infrared spectrum of a Colorado pine P/N product in the region of 700 to 1900 wavenumbers.

Fourier Transform Infrared (FTIR) Spectroscopy [see P. R. Griffiths and J. A. de Haseth, Fourier transform infrared Spectrometry. Series: Chemical Analysis. Wiley and Sons, New York, 656 pp., 1986, and A. J. Michell, Infrared spectroscopy transformed—new applications in wood and pulping chemistry, Appita, vol. 41, pp. 375-380, 1988] is a powerful technique for characterizing complex substances, such as lignocellulosic biomass, its components, and derivatives therefrom, such as the P/N fraction. The P/N product spectra can be obtained as transmission in pellets with KBr, attenuated total reflectance (on films of pure P/N product), or diffuse reflectance (on films of P/N product), displaying intensity of absorption at frequencies in the range of 700-4000 $cm^{-1}$. Due to the complexity of components, individual monomeric subunits, and the presence of polymeric structures linked by a variety of bonds, the assignment of bands is done by comparison with the spectra of known lignins, model compounds, and related substances. Only a few of these frequencies correspond to unequivocally assigned modes, such as the aromatic skeletal vibration at 1600 $cm^{-1}$, but many result from combinations of modes (skeletal vibrations and stretching modes, etc.). Table VIII displays the most important bands of the P/N product for a variety of feedstocks. A list of potential assignments of several of these bands based on the literature (see, for instance, 0. Faix and 0. Beinhoff, "FTIR spectra of milled wood lignins and lignin model polymers (DHP's) with enhanced resolution obtained by deconvolution", in Journal of Wood Chemistry and Technology, vol. 8, pp. 505-522, 1988, and references therein) is given in Table IX. Examples of FTIR spectrum for one of these products from Colorado pine is shown in FIG. 3. FTIR is a very powerful fingerprint method for the P/N product, its feedstock, the method of preparation, and the thermal history of the P/N sample. There are similarities between the FTIR of the P/N product and the FTIR of the corresponding wood lignins. There is an expected reversal in the order of importance of the bands at 1512 $cm^{-1}$ (intensity proportional to the aromatic ring content) and 1265 $cm^{-1}$ (intensity proportional to the content of aromatic methoxyl groups); for the P/N product the 1265 $cm^{-1}$ band is less intense than in the case of a milled softwood lignin, which suggests that the methoxyl content per aromatic group is smaller in the P/N product than in the milled wood lignin. This fact is confirmed by direct measurement of methoxyl content (see above). The presence of reactive phenolic units with unsaturated side chains is also confirmed by the band at 966 $cm^{-1}$. The FTIR spectrum contains a complete set of structural information on the P/N product. Differences exist between softwood- derived P/N products and even greater differences between softwood- and hardwood- derived P/N product, both quantitatively and qualitatively (see Table VIII).

TABLE VIII

| | Listing of Peaks and Intensities of Phenolics-containing/Neutrals Fractions | | | | |
|---|---|---|---|---|---|
| Wavenumbers | XIV80PN REDWOOD | XX84PN SO. PINE | BH42PN CO. PINE | XX117PN MO. PINE | BH113PNA ASPEN |
| 966 | 0.112 | 0.058 | 0.081 | 0.066 | 0.080 |
| 1030 | 0.315 | 0.187 | 0.240 | 0.170 | |
| 1037 | | | | | 0.228 |
| 1081 | | 0.110 | | | |
| 1093 | | 0.111 | 0.134 | 0.115 | |
| 1111 | | | | | 0.347 |
| 1121 | 0.294 | 0.148 | 0.189 | 0.149 | |
| 1151 | 0.309 | 0.143 | 0.196 | 0.157 | 0.174 |
| 1203 | 0.339 | | 0.223 | 0.193 | |
| 1209 | | 0.182 | | | 0.325 |
| 1233 | 0.314 | 0.181 | 0.222 | 0.188 | |
| 1237 | | | | | 0.273 |
| 1265 | 0.349 | 0.206 | 0.253 | 0.216 | |
| 1330 | | | | | 0.120 |
| 1361 | | | | 0.096 | |
| 1372 | 0.117 | 0.093 | 0.097 | 0.095 | 0.136 |
| 1428 | 0.147 | 0.095 | 0.103 | | 0.118 |
| 1451 | 0.152 | 0.104 | 0.114 | 0.107 | |
| 1455 | | | | 0.107 | |

TABLE VIII-continued
Listing of Peaks and Intensities of Phenolics-containing/Neutrals Fractions

| Wavenumbers | XIV80PN REDWOOD | XX84PN SO. PINE | BH42PN CO. PINE | XX117PN MO. PINE | BH113PNA ASPEN |
|---|---|---|---|---|---|
| 1463 | 0.157 | 0.104 | 0.115 | | 0.166 |
| 1512 | 0.352 | 0.166 | 0.206 | 0.154 | 0.194 |
| 1596 | 0.157 | 0.128 | 0.114 | 0.128 | 0.138 |
| 1603 | | | | | 0.139 |
| 1635 | | | | 0.074 | 0.057 |
| 1653 | | | | 0.102 | 0.077 |
| 1662 | | 0.104 | | 0.104 | |
| 1668 | 0.085 | | 0.094 | 0.104 | |
| 1675 | | | | | 0.0899 |
| 1684 | | | | 0.097 | |
| 1705 | 0.089 | 0.104 | 0.120 | 0.110 | 0.125 |
| 1716 | | | | 0.103 | |
| 1727 | | | | | 0.118 |
| 2934 | 0.059 | 0.072 | 0.072 | 0.075 | 0.067 |
| 2959 | 0.052 | 0.066 | 0.062 | 0.068 | 0.059 |
| 3382 | | | | | 0.073 |
| 3387 | 0.097 | 0.111 | 0.081 | 0.097 | 0.074 |

TABLE IX
FTIR of P/N products — Bands and Assignments

| Wavenumber cm$^{-1}$ | Band Number (see FIG. 3) | Possible Band Origin* |
|---|---|---|
| 1730 (shoul) | 1 | C=O stretch in unconjugated ketone; ester groups; aldehydes (conjugated), acids; |
| 1705 | 2 | C=O stretch in conjugated C=C; |
| 1675 | 3 | C=O stretch in conjugated quinone (e.g., p- substituted aryl ketones) |
| 1596 | 4 | Aromatic skeletal vibrations |
| 1512 | 5 | Same |
| 1463 | 6 | C—H deformations —CH$_3$ and —CH$_2$— asymmetric |
| 1428 | 7 | Aromatic skeletal vibrations |
| 1428 | 8 | same |
| 1361 | 9 | C—H deformation —CH$_3$ symmetric (not in OMe); phen. OH |
| 1265 | 10 | C—O—C strech in ArOCH$_3$ |
| 1233 | 11 | same and C—C/C—O stretch |
| 1209 | 12 | same |
| 1151 | 13 | C=O in carboxyl and carbonyl groups (?) |
| 1121 | 14 | secondary alcohols and C=O stretch |
| 1093 (shoul) | 15 | C—O deformation in secondary alcohols and aliphatic ethers |
| 1030 | 16 | C—O deformation in primary alcohols; C—H aromatic in-plane deformation |
| 968 | 17 | —HC=CH— (trans) out-of-plane deformation |
| 860 | 18 | C—H aromatic out-of-plane deformation |
| 810 | 19 | same (guaiacyl units) |
| 750 | 20 | same |

The position of the peaks can be modified by the presence of small amounts of ethyl acetate, which has peaks at the following wavenumbers (in cm$^{-1}$), with the intensity in parenthesis denoted as low (l), medium (m), and strong (s): 1889(l), 1829(l), 1757(s), 1558(l), 1468(m), 1465(m), 1445(m), 1374(s), 1300(m), 1241 & 1245(s), 1172(l), 1068(m), 1052(s), 938(m), 847(m), 787(l). (shoul) = shoulder

*Assignments based on the article by Faix above, and Bruce F. Briggs, "Modification of Kraft Lignins by Sulfomethylation and Oxidative Sulfonation: Structure and Mechanisms", Ph.D. thesis, North Carolina State University, 1985.

Proton Magnetic Resonance Spectra

P/N product spectra for pine samples exhibit three main spectral regions. Of the total protons in the product, the aromatic protons and unsaturated structures (6.5–8 ppm) constitute 25–35%, the aliphatic (0–3.0 ppm) about 30–40%, and the oxygenated side-chain (3.0–6.0 ppm) constituted about 30%. These proportions are compatible with the types of compounds identified by GC/MS and MB/MS as present in the P/N product. In addition, proton NMR identifies clearly the presence of reactive aldehyde protons from coniferyl aldehyde, furfural and derivatives, vanillin, cinnamaldehyde, and potentially others, because of the presence of sharp proton resonances at 9.55, 9.59, 9.62, 9.63, 9.7, and 9.8 ppm (on a 300 MHz NMR spectrometer). Aspen P/N products appear richer in reactive aldehydes than the pine species.

Carbon-13 Nuclear Magnetic Resonance (NMR) Spectra

The P/N product spectra are characterized by four spectral regions: 200–165 ppm, due to signals assignable to carbonyl and carboxyl types of carbons; 165–100 ppm, caused by aromatic and olefinic carbons; 100 to about 50 ppm arising from oxygenated side-chain carbons; 40–20 ppm, contributed by —CH$_3$ and —CH$_2$— carbons. Table X contains examples of peaks from a high resolution broad-band decoupled carbon-13 NMR spectrum of P/N products from various feedstocks in deuterated acetone solvent and assignments based on comparisons with lignins and model compounds (see E. Breitmeier and W. Voelter, 13 Carbon NMR Spectroscopy, 3rd edition, VCH, Weinheim, 515 pp., 1987 for references to the technique; H. Nimz, D. Robert, O. Faix, M. Nemr, "C-13 NMR Spectra Softwoods and Compression Wood", Holzforschung, vol. 35, pp. 16–26, 1981, J. McKinley, G. Barras, and H. L. Chum, "The Application of Nuclear Magnetic Resonance to the Characterization of Biomass Liquefaction Products," in Research in Thermochemical Biomass Conversion, edited by A. Bridgwater and J. Kuester, London: Elsevier Applied Science, pp. 236–250, 1988, and references therein).

TABLE X
Examples of peak positions of carbon-13 nuclear magnetic resonance spectra and corresponding intensities for various P/N products in deuteroacetone (300 MHz spectrometer)

| XIX-12-PN CO PINE | | BH1-13-PN ASPEN | | XX-84-PN SOUTHERN PINE | |
|---|---|---|---|---|---|
| FREQ., PPM | INT. | FREQ., PPM | INT. | FREQ., PPM | INT. |
| —CH$_3$ groups in C=O environments | | | | | |
| 18.4 | 33.4 | 18.4 | 40.0 | 18.4 | 32.5 |
| 20.7 | 36.2 | 20.7 | 18.9 | 20.7 | 25.5 |
| 24.3 | 28.4 | | | 24.3 | 35.1 |
| 25.3 | 33.5 | | | 25.4 | 36.1 |
| 26.2 | 24.0 | 26.2 | 17.3 | 26.2 | 22.3 |
| —CH$_3$ and —CH$_2$ groups in saturated aliphatic groups | | | | | |

TABLE X-continued

Examples of peak positions of carbon-13 nuclear magnetic resonance spectra and corresponding intensities for various P/N products in deuteroacetone (300 MHz spectrometer)

| XIX-12-PN CO PINE | | BH1-13-PN ASPEN | | XX-84-PN SOUTHERN PINE | |
|---|---|---|---|---|---|
| FREQ., PPM | INT. | FREQ., PPM | INT. | FREQ., PPM | INT. |
| 32.3 | 26.8 | 32.3 | 41.5 | 32.2 | 29.0 |
| 32.5 | 23.2 | 32.5 | 27.0 | 32.5 | 31.9 |
| 34.1 | 27.3 | 33.9 | 49.1 | 34.1 | 28.9 |
| 34.2 | 31.6 | 34.2 | 18.1 | 34.3 | 20.4 |
| 35.5 | 24.9 | 35.5 | 42.8 | 35.5 | 24.3 |
| 37.4 | 27.3 | | | 37.4 | 20.6 |
| 37.9 | 21.7 | | | 37.9 | 19.6 |
| 38.8 | 26.5 | 39.4 | 29.0 | 38.8 | 25.7 |
| —OCH₃ groups | | | | | |
| 55.7 | 14.8 | 55.8 | 10.4 | 55.8 | 9.6 |
| 56.1 | 201.2 | 56.1 | 193.5 | 56.1 | 149.8 |
| 56.2 | 138.4 | 56.2 | 116.6 | 56.2 | 100.3 |
| Other oxygenated carbons | | | | | |
| 68.9 | 34.9 | | | 68.9 | 38.5 |
| 73.0 | 24.6 | | | 73.1 | 20.1 |
| Aromatic carbons and unsaturated carbons | | | | | |
| 109.5 | 37.3 | 109.5 | 64.5 | 109.6 | 33.9 |
| 109.7 | 41.1 | 109.7 | 79.0 | 109.8 | 37.3 |
| 109.9 | 39.0 | 109.9 | 42.4 | 110.0 | 28.1 |
| 110.7 | 36.8 | 110.8 | 31.8 | 110.8 | 30.8 |
| 111.3 | 33.5 | 111.4 | 32.6 | | |
| 111.4 | 56.9 | 111.4 | 57.2 | 111.4 | 25.9 |
| 112.3 | 42.2 | 112.3 | 43.0 | 112.4 | 39.8 |
| 112.5 | 26.2 | 112.6 | 28.6 | 112.7 | 33.2 |
| 112.7 | 29.6 | 112.7 | 35.3 | 112.8 | 29.5 |
| 112.8 | 24.7 | 112.8 | 33.6 | | |
| 112.9 | 23.8 | 113.0 | 23.6 | | |
| 113.0 | 27.5 | 113.0 | 20.6 | 113.0 | 23.1 |
| 113.1 | 32.7 | 113.1 | 29.6 | 113.2 | 32.2 |
| 113.2 | 58.8 | 113.2 | 68.8 | 113.2 | 33.1 |
| 113.3 | 38.1 | 113.3 | 25.1 | 113.4 | 31.1 |
| 115.1 | 26.4 | | | 115.2 | 30.3 |
| 115.2 | 51.7 | | | 115.2 | 31.6 |
| 115.3 | 55.3 | 115.4 | 51.2 | 115.3 | 56.5 |
| 115.4 | 98.0 | 115.5 | 115.2 | 115.4 | 47.3 |
| 115.6 | 96.0 | | | 115.5 | 108.7 |
| 115.6 | 109.6 | 115.6 | 136.3 | 115.7 | 99.2 |
| 115.8 | 90.0 | 115.8 | 90.1 | 115.8 | 72.0 |
| 115.8 | 150.9 | 115.8 | 130.7 | 115.8 | 98.1 |
| 116.0 | 65.1 | 116.0 | 80.4 | 115.9 | 104.7 |
| 116.1 | 166.6 | 116.1 | 120.6 | 116.1 | 152.3 |
| 116.5 | 42.7 | 116.5 | 25.1 | 116.5 | 42.2 |
| 116.8 | 52.4 | 116.8 | 27.0 | 116.8 | 45.8 |
| 119.8 | 44.4 | 119.8 | 62.8 | 119.8 | 45.3 |
| 120.1 | 26.9 | 120.1 | 38.2 | 120.2 | 29.0 |
| 120.3 | 47.1 | 120.4 | 40.2 | 120.3 | 48.5 |
| 120.5 | 51.9 | 120.5 | 52.3 | 120.5 | 143.3 |
| 120.6 | 137.8 | 120.7 | 72.2 | 120.7 | 29.0 |
| 120.9 | 63.6 | 120.9 | 33.8 | 120.7 | 55.2 |
| 121.4 | 31.5 | 121.4 | 41.8 | 121.4 | 36.4 |
| 121.6 | 29.1 | 121.5 | 25.7 | 121.5 | 31.1 |
| 121.8 | 47.9 | 121.8 | 44.1 | 121.8 | 50.7 |
| 121.9 | 45.3 | 122.0 | 53.6 | 121.9 | 50.1 |
| 122.5 | 29.1 | 122.6 | 21.1 | 122.6 | 23.9 |
| 122.7 | 38.4 | 122.7 | 28.4 | 122.7 | 29.7 |
| 123.0 | 34.7 | 123.0 | 43.7 | 122.9 | 41.1 |
| 124.6 | 49.9 | 124.6 | 36.6 | 124.7 | 51.2 |
| 126.9 | 35.1 | 126.9 | 58.5 | 126.8 | 29.8 |
| 127.0 | 37.4 | 127.0 | 20.2 | 127.0 | 37.3 |
| 127.7 | 29.5 | 127.7 | 26.6 | 127.7 | 28.1 |
| 130.1 | 29.7 | 130.1 | 34.4 | 130.1 | 27.4 |
| 130.5 | 29.6 | 130.5 | 27.0 | 130.6 | 32.5 |
| 131.8 | 32.2 | 131.8 | 44.7 | 131.8 | 39.6 |
| 144.9 | 30.9 | 145.0 | 33.9 | 145.0 | 20.3 |
| 145.1 | 27.8 | 145.2 | 26.0 | 145.2 | 23.2 |
| 145.2 | 27.1 | 145.2 | 29.1 | 145.2 | 22.3 |
| 145.3 | 28.2 | 145.3 | 27.5 | 145.3 | 20.3 |
| 145.4 | 28.9 | 145.4 | 25.5 | 145.4 | 19.4 |
| 145.4 | 31.2 | 145.4 | 28.6 | 145.4 | 24.0 |
| 145.6 | 32.3 | 145.6 | 25.4 | 145.6 | 32.4 |
| 145.7 | 31.9 | 145.7 | 24.3 | 145.7 | 21.1 |
| 145.8 | 99.6 | 145.8 | 57.7 | 145.8 | 22.6 |
| 145.9 | 33.0 | 145.9 | 25.2 | 145.9 | 52.1 |
| 146.1 | 24.7 | 146.1 | 27.1 | 146.1 | 19.1 |
| 146.2 | 23.2 | 146.2 | 23.4 | 146.2 | 16.6 |
| 146.4 | 23.1 | 146.4 | 22.8 | 146.4 | 14.8 |
| 146.5 | 23.1 | 146.5 | 32.3 | 146.5 | 23.1 |
| 146.6 | 33.1 | 146.6 | 34.5 | 146.6 | 21.4 |
| 147.0 | 27.6 | 146.9 | 57.4 | 146.9 | 19.1 |
| 147.3 | 19.4 | 147.3 | 22.2 | 147.3 | 21.5 |
| 147.4 | 17.7 | 147.4 | 21.3 | 147.5 | 14.9 |
| 147.7 | 18.4 | 147.7 | 22.6 | 147.6 | 15.4 |
| 147.8 | 21.1 | 147.8 | 24.3 | 147.8 | 15.5 |
| 147.9 | 23.8 | 147.9 | 41.9 | 147.9 | 23.3 |
| 148.0 | 26.0 | 148.0 | 36.9 | 148.0 | 23.2 |
| 148.1 | 33.5 | 148.1 | 32.9 | 148.1 | 20.8 |
| 148.2 | 45.1 | 148.2 | 68.8 | 148.2 | 30.1 |
| 148.3 | 36.2 | 148.3 | 48.6 | 148.3 | 36.0 |
| 148.4 | 33.8 | 148.4 | 55.0 | 148.4 | 28.3 |
| 150.7 | 27.8 | 150.7 | 23.2 | 150.9 | 16.8 |
| 153.4 | 23.3 | | | | |
| 154.2 | 54.1 | 154.2 | 54.0 | | |
| | | | | 154.4 | 48.2 |
| 155.3 | 28.0 | | | 155.5 | 23.4 |
| Carboxylic Acids and esters | | | | | |
| 178.1 | 36.3 | 178.1 | 7.4 | | |
| 178.2 | 8.0 | | | 178.2 | 28.5 |
| 178.4 | 17.9 | 178.4 | 6.3 | 178.5 | 17.2 |
| Aldehydes and ketones | | | | | |
| 191.2 | 39.1 | 191.2 | 27.0 | | |
| 191.3 | 19.9 | 191.3 | 9.4 | | |
| 191.4 | 10.2 | 191.4 | 10.7 | 191.4 | 18.3 |
| 194.1 | 50.3 | 194.1 | 53.6 | | |
| 194.2 | 15.7 | 194.1 | 51.0 | | |
| 194.2 | 10.4 | 194.2 | 12.1 | 194.3 | 46.9 |

Compared to lignins, the P/N products exhibit a carbon-13 NMR composed of much sharper peaks overall, with a higher proportion of signals in the aliphatic region and fewer signals in the region of oxygenated side-chain structure, indicative of the lower degree of polymerization through ether-bonded structures in the pyrolyzed lignin molecules than in milled-wood lignins. A higher degree of free phenolic structures is also seen, as predicted by the free phenolic content. In addition, the NMR spectrum reveals a number of carbonyl-containing compounds such as residual solvent, acetovanillone, vanillin, and other compounds. The carbon-13 NMR spectral data thus confirm the previous spectroscopic and functional group assignments.

Viscosity

The viscosity of the P/N product is a function of the temperature and the amount of residual low molecular weight solvents (e.g., water, ethyl acetate, and added phenol as shown in FIG. 2 and Table VII). Viscosity measurements were made using a Brookfield Model LVTD viscometer equipped with a Thermosel system, which enabled measurements at various temperatures. At 30° C., the viscosity of a Southern Pine P/N product (P/N product 4) was 65,000 cP for a 1 wt % residual moisture. Increasing the moisture level to 5% drops the viscosity by a factor of ten. Increasing the temperature to 40° C., decreases the viscosity to 15,000 cP at 1% moisture level. Again, increasing the moisture to about 5% causes the viscosity to decrease by a factor of ten at the higher temperature. Other samples prepared differently in the evaporation step, subjected to less severe thermal treatments, have lower viscosities. Sample 17, with a residual level of 8.8% (water and ethyl acetate) displayed a viscosity of 13,000 cP at 30° C. or 2,000 cP at 45° C. Addition of 25 and 50 wt % of phenol decreases the viscosity to 680 and 80 cP, respectively, at 30° C., or to 150 and 30 cP at 45° C. The P/N product viscosity can thus be controlled and maintained at a desired practical level by addition of small or large levels of low-molecular weight compounds, such as water or phenol, or by an increase in operating temperature, or a combination of both. Colorado pine samples (212) had viscosities in the 4,000 to 50,000 cP at 45° C., for total levels of water and ethyl acetate (from 2 to 10 wt %) shown on Table III. A sample that was evaporated at higher temperatures than others (P/N product 9) had a higher viscosity (140,000 cP at 45° C.).

P/N Product Stability

Spectral properties (FTIR, NMR, and MBMS), viscosity, and molecular weight distribution were used to assess changes upon storage at room temperature and at higher temperatures. Effects of various materials on aging were also assessed to better define the materials to be used for plant construction and storage. Materials investigated were glass, stainless steel, mild steel, and fiberglass. Colorado pine P/N product No. 6 and Southern pine P/N product No. 17 were used in these studies. Temperatures investigated were 22° C., 36° C., and 60° C. or 80° C. The properties that vary the most with aging of the P/N product are viscosity and molecular weight distribution. These changes are accompanied by less marked spectral changes, such as shown by FTIR and NMR. As expected, viscosity increases with increased time especially at elevated temperatures. The viscosity changes can be directly correlated to increases in the proportion of high- molecular weight components present in the P/N product as it ages (polymeric products with more than 2000 apparent molecular weight). Initial rates treatment measuring the increase in the concentration of these high-molecular weight polymeric materials at the beginning of the aging studies is compatible with a pseudo-first order dependence on the disappearance of low-molecular weight components into the high molecular weight polymers. Linear plots of log of a parameter, proportional to the concentration of [1-(high-molecular weight polymers by HPSEC)] versus time were obtained, and an activation energy of 24 kcal/mole, and a pre-exponential factor of $3.7 \times 10^8 \sec^{-1}$ were calculated for the aging of the P/N product.

At 22° C., the storage of the P/N product on any of these materials for 140 days increased the amount of high-molecular weight materials by a factor of 1.5; viscosity increased by a factor of two during the same time period. These are actually small changes. In order to observe aging of the materials, the temperature has to be raised to at least 37° C., in which case, increases in viscosity by of a factor of two can be seen in about 30 days. At 60° C., a doubling of viscosity was achieved in one day. A usable storage life of 4–6 months is expected for these materials at 22° C. For the P/N product 17, at room temperature, a 17% increase in viscosity was observed in one month. By addition of 25 and 50% by weight of phenol, the increase in viscosity were 17 and 16%, respectively. Within the experimental error of the various techniques employed, the materials tested had no effect on the aging of the neat P/N products; only time and temperature caused changes in the P/N product.

Figure 4A:
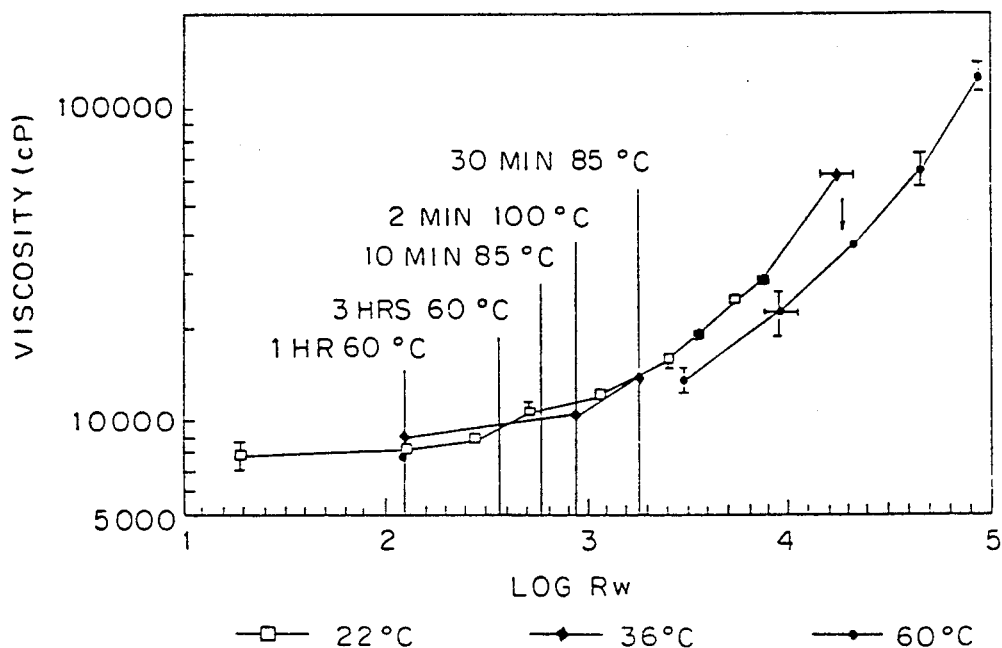
FIG. 4a illustrates the effect of the increase in the severity of storage upon the viscosity of the P/N product at 45° C.
Figure 4B:
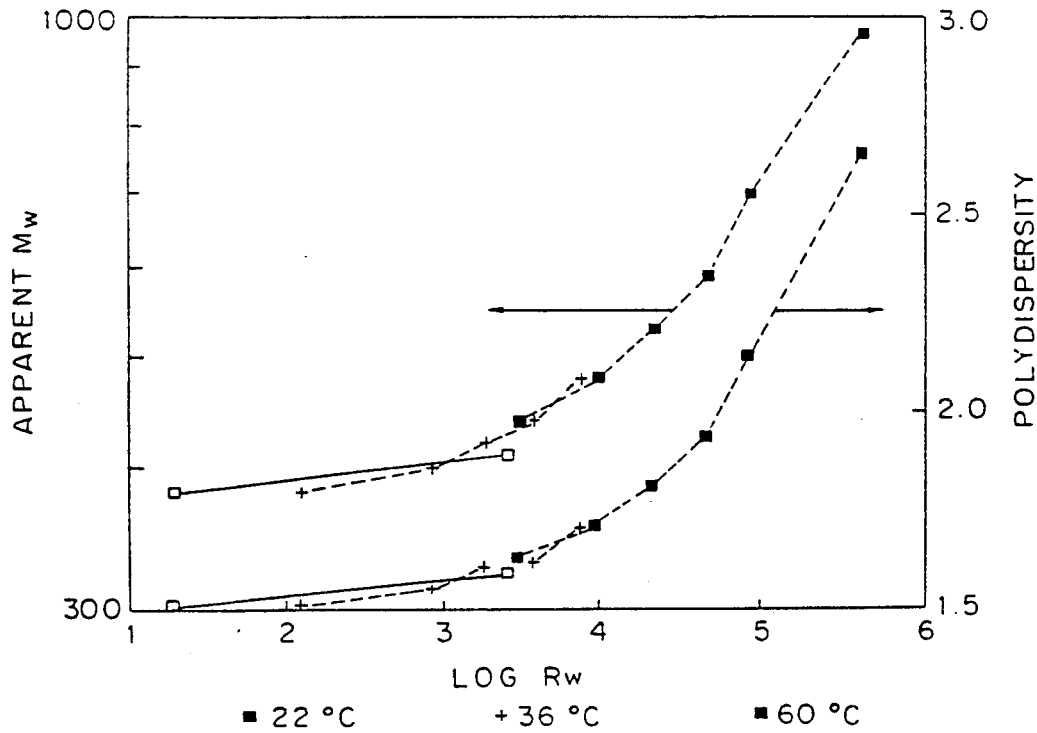
FIG. 4b illustrates the same effect on the apparent molecular weight of the P/N product as well as its polydispersity.

Effects of time and temperature can be jointly observed to provide a guide for the production of the P/N product as far as acceptable time/temperature profiles for solvent evaporation or storage are concerned. This treatment is based on severity concepts in the literature that have been utilized in pulping, fractionation of lignocellulosics, and other processes [e.g., K. E. Vroom, "The "H" factor: A means of expressing cooking times and temperatures as a single variable", *Pulp and Paper Magazine of Canada*, vol. 58, pp. 228–231 (1965); R. P. Overend and E. Chornet, "Fractionation of Lignocellulosics by Steam-aqueous pretreatment", *Phil. Transaction of the Royal Society London, A*, vol. 321, pp. 523–536, 1987; H. L. Chum, D. K. Johnson, and S. K. Black, "Organosolv Pretreatment for Enzymatic Hydrolysis of Poplars. II. Catalyst Effects and the Combined Severity Parameter," *Ind. Eng. Chem. Res.* Vol. 29, 156–162, 1990; H L. Chum, S. K. Black, D. K. Johnson, and R. P. Overend, "Pretreatment—Catalyst Effects and the Combined Severity Parameter" *Appl. Biochem. Biotechnol.*, Vol. 24/25, pp. 1–14, 1990]. A reaction ordinate, the severity factor, is defined as $R_w = \exp[(T_r - T_b)/w] \times t$, where $T_r$ is the reaction temperature, $T_b$ is the base temperature (a temperature at which the reactions are negligible), t is the duration of the reaction, and w is an experimental parameter, related to the activation energy, and equal to 7.4 degrees K. in the present case (or 26 kcal/mol). Following the procedure described in the last paper mentioned in this paragraph, the plot shown in FIG. 4a can be made, which unifies the time-temperature viscosity data for the lower temperatures, and depicts the effect of solvent evaporation at various time-temperature profiles on the viscosity of the corresponding solutions. FIG. 4b shows the effect of severity on the apparent weight average molecular weight and polydispersity of the polymers formed upon aging. The activation energy calculated using this first-order kinetic model is 26 kcal/mol, in close agreement with that from the initial rates kinetic treatment of 24 kcal/mol, within the experimental errors of both procedures.

Insight into the nature of the polymers formed upon aging comes from chemical and spectroscopic analyses. For the studies involving the P/N product No. 6, the ethyl acetate content decreased from 5% to 2.5% in 140 days at 60° C., while the water content increased from 1% to 2%. The changes that are responsible for the decrease in ethyl acetate content are chemical in nature, and not simple evaporation, since the samples were stored in reasonably well sealed bottles. Through solution carbon-13 NMR spectroscopy, on a JEOL instrument at 90 MHz, spectra were obtained as a function of temperature. There is a substantial increase in a peak at 175 ppm for samples aged at 60° C., whereas the signals decrease at 172.85 (ethyl acetate carbonyl) and 61.4 ppm (methyl carbon of ethyl acetate). The signal at 175 ppm is compatible with the formation of phenol acetates by transesterification, which releases ethanol, and decreases the ethyl acetate content. Signals at 116 ppm (carbons 3 and 5 in the guaiacyl ring) do not change within the experimental error.

A significant peak appears at 57.9 ppm, which can be assigned to $-CH_x-O-$ carbons, which would be present if the high-molecular weight polymers formed were ether bonded. The formation of these ether-bonded polymers releases water. Similar information can be inferred from the FTIR spectral changes upon aging. Increases in the intensities of peaks at 1201 and 1705 cm$^{-1}$ versus 1515 cm$^{-1}$ were observed, also indicating ether formation, whereas a decrease in the peak at 1668 cm$^{-1}$ relative to 1515 cm$^{-1}$ was observed. The 1668 cm$^{-1}$ peak contains major contributions from the ethyl acetate solvent. The most likely ether-forming polymerization reactions under neutral conditions involve polymerization of the reactive hydroxyl-containing components of the P/N product such as 5-hydroxymethyl furfural and phenolic moieties that contain side chains with activated hydroxyl groups adjacent to the ring in α-position. Simple etherification reactions could be taking place. Polyether formation exhibits a constant rate, though the viscosity increases substantially, and has an activation energy of 23 kcal/mol (P. J. Flory, Journal of the American Chemical Society, vol. 59, p. 466, 1937 or vol. 61, p. 3334, 1939; see also A. Pizzi, Phenolic Resin Wood Adhesives in "Wood Adhesives", A. Pizzi ed., Marcel Dekker, New York, pp. 105-176, 1983), which is very similar to that observed for the P/N product aging. The P/N product aging reactions, in fact, lead to prepolymer formation. Such prepolymers are expected to cure well upon heating. In fact, a prepolymerized sample (>600,000 cP at 30° C.) treated for resin formation in the same way as described in Table III, gave about a 100 sec cure time at 150° C., versus 93 sec for the equivalent sample unpolymerized (P/N product No. 3), identical within the experimental error of the measurement. Other indirect evidence for the fact that the aged P/N product is a polyether is the fact that pyrolysis molecular beam mass spectrometry cannot differentiate between samples as a function of age. Ether bonds are very easy to cleave under thermal conditions, leading to the same or similar monomers that would be present in the unaged sample, thus, one would not expect to detect major differences using this technique.

Condensation reactions could also be taking place, involving the reactive aldehyde groups. All these reactions are compatible with the observed increase in molecular weight and viscosity. Consequently the aging proceeds through molecule-building chemical reactions which are thought to involve etherification and condensation. Direct evidence for the disappearance of the reactive aldehyde compounds, involved in these condensation reactions, is provided by the almost complete disappearance of the signals at 9.5 to 10 ppm in the proton NMR spectra upon aging.

DETAILED DESCRIPTION OF THE PREFERRED EMBODIMENTS

Part B

Novolaks Prepared with Fractionated Fast Pyrolysis Oils

EXAMPLE XI

Resin Preparation 282.5 g of the P/N product #2 from Table III derived from a fast-pyrolysis oil obtained from pine sawdust according to the process described in Example IV was placed in a reaction container. 312.2 g of 90% phenol (aqueous) and 6.0 g of concentrated hydrochloric acid were added to the P/N product. Other acids such as sulfuric acid could have been used and have been used; in the examples given the samples were prepared with HCl. There are no major differences in behavior by using the preferred-less corrosive sulfuric acid, although both are used (see, for instance, Shinohara et al., U.S. Pat. No. 3,862,089 of 1975). The mixture was heated to about 96° C. and 175.7 g of 37% formalin was added slowly under constant stirring. During the addition of the first half of the formalin, a brisk exotherm occurred and gradually died down upon continuation of the formalin addition.

After all of the formalin was added, the reaction mixture was kept at 90° to 95° C. for an additional hour. The mass was then cooled to 85° C. and a solution of 3.34 g of sodium carbonate dissolved in 70.0 g of water was slowly added under constant stirring. The reaction mass was heated under slowly increasing vacuum until a vacuum of 27 inches was reached at a temperature of 150° C. The vacuum and heating were discontinued and, while still hot, the resulting resin was poured into a cooling pan. The yield was 523 g. After the resin had cooled to room temperature, it was crushed to produce small pieces for further grinding and processing.

Three 1.25 g samples of the resin were ground to a coarse grind by hand in a mortar and pestle and mixed with hexamethylene tetramine and lime (calcium hydroxide) as follows:

|  | A | B | C |
| --- | --- | --- | --- |
| Resin, g | 1.25 | 1.25 | 1.25 |
| Hexamethylene tetramine, g | 0.20 | 0.26 | 0.30 |
| Lime, g | 0.20 | 0.23 | 0.30 |
| Stroke cure, seconds at 150° | 170 | 162 | 150 |

These stroke cure times are well within commercially acceptable ranges.

| Compounding In preparing the molding compound, a mixture comprising the following materials was made: | |
| --- | --- |
| Novolak resin | 250.0 g |
| Hexamethylene tetramine | 37.5 g |
| Lime | 25.0 g |
| Zinc stearate | 7.5 g |
| Wood flour (filler) | 150.0 g |

The mixture was pebble milled for about 1 hour to a very fine well blended powder and nip rolled a few seconds at 100° to 105° C. and sheets were pulled off and cooled. The sheets were broken up into pieces smaller than ¼" in any dimension and used in molding compounds.

Molding was done in a mold heated to 330° F. at a pressure of 6,600 psi to obtain small disc of 1" diameter.

It should be noted that, when the novolak prepared using the P/N fraction of the invention as a replacement for phenol is cooled to about 110° C. (the melt is of a gel consistency that is easily injection moldable) and has a "snap" cure. Both of these properties are highly desirable for injection molding and many other types of commercial applications.

EXAMPLE XII

A novolak was prepared from the P/N product #1 (see Table III) derived from fast-pyrolysis of redwood as feedstock using a batch fractionation step.

The following parts by weight of materials was used in preparing the novolak resin:

| | |
| --- | --- |
| P/N Fraction | 18.8 |

| | |
|---|---|
| 88% Phenol | 21.3 |
| HCl (Concentrated) | 0.42 |
| 37% Formaldehyde | 11.80 |
| Sodium Carbonate (anhydrous) | 1.00 |
| Water | 15.00 |

A mixture of the P/N fraction, phenol and hydrochloric acid was heated to 95°–97° C. for about 30 minutes. Formaldehyde was added dropwise under constant stirring and the heating was continued on a steam bath for another 30 minutes after the formaldehyde addition was completed. Sodium carbonate dissolved in water was added slowly to achieve neutralization. The resulting resin was washed several times with hot water and the pH of the last wash water was 7.0.

Blends of the resin with hexamethylene tetramine and lime in the following amounts by weight gave the following gel time at 150° C.:

| | |
|---|---|
| Resin | 1.25 |
| Hexamethylene Tetramine | 0.30 |
| Lime | 0.30 |
| 150° C. gel time, seconds | 280 |

EXAMPLE XIII

Similar to Example XII, except that pine sawdust was the feedstock and a sample of P/N product #5 was used. The gel time was 175 seconds on a parallel determination of sample #5 and 1. A latter sample of P/N product #5 run in parallel with samples 2-5, 7-12, gave 138 second gel time. These comparative gel times are shown in Table III for all these samples and others described before.

It is clear from a comparison of Examples XII and XIII that the reactivity of the novolak resin products from this redwood P/N fraction is less than that obtained from the pine sawdust P/N fraction when used under phenolic resin type reaction conditions.

When the fast-pyrolysis oil derived from pine sawdust according to Example VI is fractionated on a continuous basis and the oil flow rate is doubled (10 ml/min), the P/N fraction obtained therefrom produces a novolak resin which, when prepared according to Example XX, cures at 150° C. in 128 seconds (P/N product #12).

When the oil flow rate is tripled (15 ml/min), the P/N fraction obtained therefrom produces a novolak resin which, when prepared according to Example, cures at 150° C. in 95 seconds (P/N Product #11). While the exotherms in the double and triple flow rate oil materials are about 115° C. (compared to about 108° C. for the single flow rate oil materials), it was found that the novolak prepared from the triple flow rate oil material was best in brittleness, was non-caking and glossy and gave better cured resins with much better hot rigidity. Also, it dehydrated easier when compared to standard novolaks (without the P/N fast pyrolysis fraction replacing a portion of the phenol), and this is a processing advantage with much merit under commercial molding conditions.

Similarly, it was found that novolaks wherein up to 50 weight percent of the phenol was replaced with 50% of P/N phenolic fractions obtained from P/N products of fast-pyrolysis oils obtained from Douglas fir bark have much better (shorter) cure times compared with their corresponding pine sawdust derived analogues (Example III).

Table XI shows test data for molds prepared in which 50% by weight of phenol in a novolak resin is replaced with a P/N fraction obtained from a fast-pyrolysis oil from pine sawdust.

TABLE XI

| FLOWS | POWDER PROPERTIES | PHYSICALS | |
|---|---|---|---|
| Small cup ct/wt/15.112 | Sp.Gr. 1.340 Izod | Impact strength | .25 |
| | | Tensile strength | 6,000 |
| | | Flexure | 9,300 |
| | | Water absorb. | .56 |
| Brabender 125° C. - 253 | | | |
| Low Torque - 550 | | | |
| pH 10.7 | | | |

While any acid may be used to catalyze the P/N fraction and phenol reaction with formaldehyde in preparing the novolak resins, it is preferred to use sulfuric acid, hydrochloric acid, phosphoric acid and oxalic acid. Most preferred, however, is sulfuric acid since hydrochloric acid can be corrosive to molding equipment.

In order to produce a useful novolak resin and/or molding composition containing the P/N fraction from the fast-pyrolysis oil process according to the invention, it has been found that from about 25 to about 75% by weight of the phenol normally used in a phenol-formaldehyde novolak resin can be replaced with the P/N fraction. Examples XI–XIII only illustrate formulations that can be made using the various P/N products obtained by fast pyrolysis and fractionation of these oils as described in Examples I through X, and summarized on Table III. The intent of Table III is to show comparative results on a variety of P/N products. The gel times values listed on the Table are those performed with as many samples as possible for comparative purposes. Comments on their performance are also listed on Table III. These tests are done on small samples, and for this reason, the absolute values of the gel times are not as meaningful as their relative values.

The various novolaks made have been characterized by physico-chemical methods.

Molecular-Weight Distribution of Components

Figure 5A:
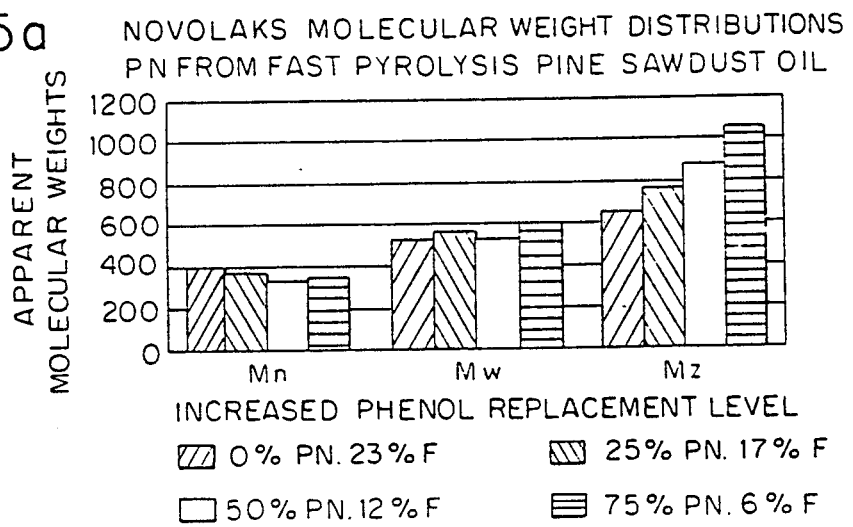
FIG. 5a illustrates the molecular weight distributions of the various novolaks containing P/N product No. 2 (defined in Table III) in replacement of phenol at various levels; also indicated are the levels of formaldehyde. The catalyst is HCl.
Figure 5B:
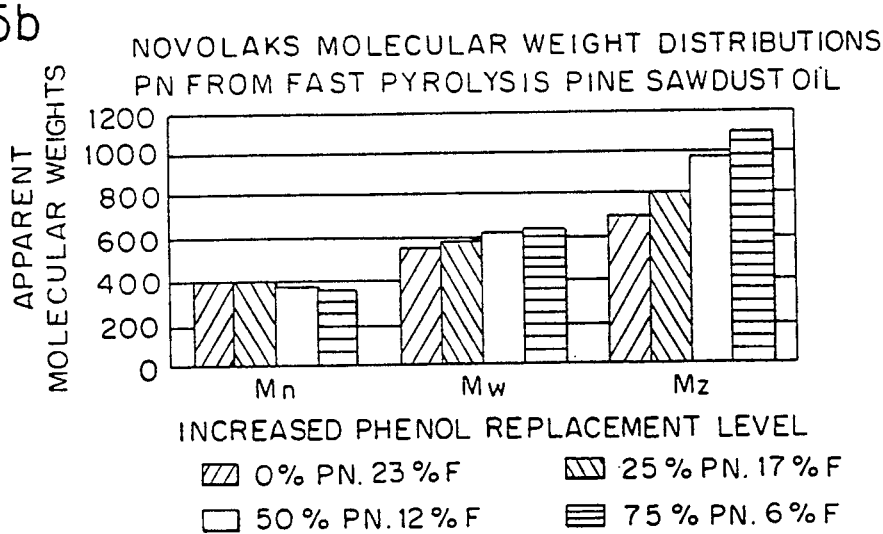
In FIG. 5b the same properties are illustrated, except that the catalyst was sulfuric acid.
Figure 5C:
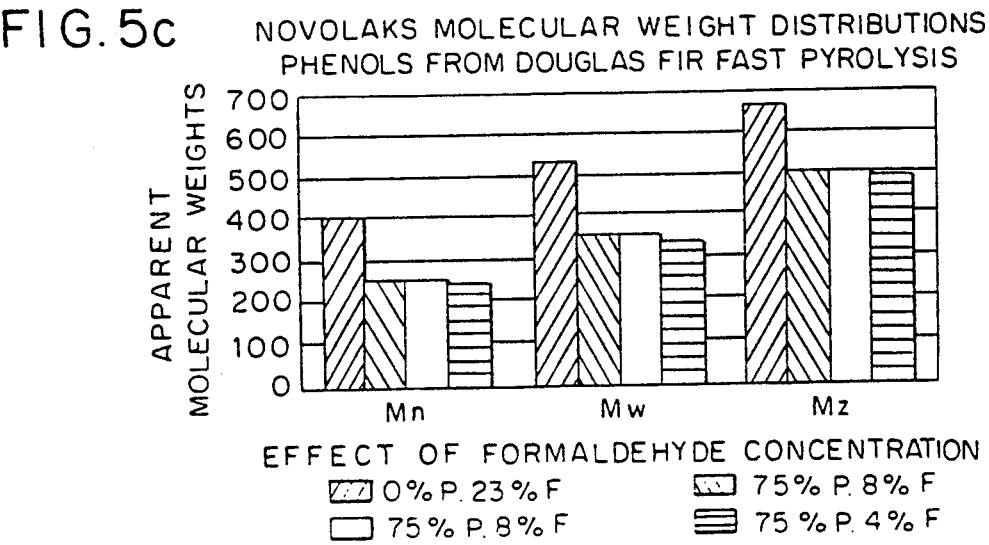
In FIG. 5c, the replacement of phenol was made with the phenolic material derived from Douglas fir bark as described in Example III.

A method similar to that employed in the characterization of the P/N product above was employed to investigate novolaks made from the Colorado Pine mixture and the Douglas fir bark. Examples of that distribution are given for a wide variety of proportions of the formaldehyde and the phenol, and are shown on FIGS. 5a (pine HCl catalyst), 5b (pine $H_2SO_4$ catalyst), and 5c (Douglas fir phenolics, HCl catalyst). From the distribution of molecular weights it is apparent that the different acid catalysts produce very similar novolak resins. The apparent number-, weight-, and z-average molecular weights of the novolaks prepared with replacement of 25, 50, and 75% of phenol with the P/N product No. 2 and various amounts of formaldehyde are shown on FIGS. 5a and 5b as a function of the acid catalyst. These weight distributions are identical within the experimental error for the catalysts. Whereas there is a slight decrease in the apparent number-average molecular weight, both the weight- and z-average molecular weights increase slightly upon replacement of phenol with the P/N products. However, the changes are small. The polydispersities are very similar to those of the corresponding phenolic resins, or slightly higher. However, the apparent number-, weight-, and z-average molecular weights are all much smaller with the phenolic materials produced from the phenolic portion of the P/N product of Douglas fir bark. This prepolymeric material is indeed significantly lower in molecular weights than the corresponding materials derived from phenol alone. The bark materials all presented a very low polydispersity, a property that is highly desirable in a variety of resins. They are also faster than other materials tested at the same time.

Carbon-113 Nuclear Magnetic Resonance (NMR) Spectra The phenolic novolaks and P/N-containing novolaks produce NMR spectra (see FIG. 6), which are characterized by the following spectral regions:
a) 150 ppm due to hydroxy-substituted carbons (HSC);
b) 130 ppm due to unsubstituted meta aromatic carbons (UMAC);
c) 125 ppm due to methylene-substituted aromatic carbons (MSAC);
d) 120 ppm due to unsubstituted para aromatic carbons (UPAC);
e) 115 ppm due to unsubstituted ortho aromatic carbons (UOAC);

Aliphatic Methylene Bridge Carbons f) 40 ppm due to para-para methylene bridge (PPMB)
g) 35 ppm due to ortho-para methylene bridge (OPMB);
h) 30 ppm due to ortho-ortho methylene bridges.

These assignments are based on various solution state carbon-13 NMR data, such as taught by S. A. Sojka, R. A. Wolfe, E. A. Deitz, B. F. Daniels, Macromolecules, vol. 12, 767–770, 1979. In addition, for the P/N-containing novolaks, the region of 56 ppm has a strong peak corresponding to the methoxyl groups linked to the aromatic rings. While these spectra have not been recorded under quantitative conditions, the comparison of each spectral region can be made from sample to sample. These changes can be seen for the aromatic and aliphatic carbon regions on FIGS. 7a and 7b. While the changes are modest, some of them (UMAC and UPAC) do not behave as the addition of the spectra of the unsubstituted and 100% substituted resin would dictate, thus suggesting participation of the P/N materials in the bonding. A small increase in the OOMB content is also seen as the materials get enriched in P/N product, which is reasonable, since these materials have both ortho and para positions with more substituents than the pure phenol-derived resin. The increase in the OOMB in the case of the Douglas-fir derived novolak is illustrated in FIG. 7c. The amount of OOMB is significantly increased at 50%, much more than the increase in the corresponding P/N product derived from pine. Therefore, the Douglas-fir bark material produces a high-ortho novolak, which is a desired material because of its increased reactivity relative to other novolaks. Whereas P/N product #2 gave 120 seconds gel time, the Douglas fir bark phenolics under similar conditions gave 48 seconds and had a good hot rigidity. These resins can be used in many applications because of short cure times.

The NMR spectra confirm independently the molecular weight distribution determined by high performance size exclusion chromatography. Using the ratio of phenolic carbon integrals that represent terminal and internal carbons (155–158 to 150–153 ppm, respectively), one can calculate that the weight-average molecular weight ranges from 400 to 600, in good agreement with the other technique (see FIG. 5a). The ratio of free phenolic structures in ortho versus para positions has also been shown to depend critically on the amount of formaldehyde. Thus, for bark, using a 4% formalin level one can obtain a ratio of 6 (ortho-/para-) (the ratio for pure phenol-formaldehyde), whereas doubling the amount of formaldehyde, the ratio decreases to one at 75% level of substitution. For Pine P/N-containing novolaks this ratio varies from 5 to 2 (35 to 75% replacement, respectively).

In conclusion, the P/N products from pine and the Douglas fir phenolic materials give novolaks that can be made to fulfill a wide range of properties. The Douglas fir materials have lower molecular weights and high reactivity; they lead to high ortho-novolaks. The pine-derived materials have similar distribution of molecular weights than phenol-formaldehyde and similar cure rates.

P/N PRODUCT in Novolak systems—property-performance relationship.

A key property that will determine the utility of the P/N product in commercial applications is the ability of the fast pyrolysis/fractionation/solvent evaporation processes to lead to a reproducible mixture of compounds, capable of replacing phenol to the desired extent in phenol-formaldehyde thermosetting resins. Since there are over 100 individual compounds in the P/N product mixture from pine species, it is necessary to develop simple methods capable of assessing product reproducibility, and predict product properties based on spectral information, such as from fast physical measurements, and chemometrics of the spectroscopic data (e.g., FTIR or MBMS). Cluster analysis, dendrograms, principal component factor analysis, and multiple linear regression are examples of the chemometric techniques employed to assess reproducibility and physical property prediction of parameters such as gel times and viscosity based on the spectral properties of the various P/N products (see, for instance, M. A. Sharaf, D. L. Illman, B. R. Kowalski, Chemometrics, Wiley, New York, 1986). These techniques offer exploratory data analysis and pattern recognition through a combination of mathematical and interpretative methods. The goal is to effectively display all data in a simplified way which contains the bulk of the information in the original measurement set, while giving some insight into the fundamental influences in the set of samples. The current data set was treated with the Ein*Sight TM software by Infometrix, Inc. for MS DOS systems. The FTIR spectra of the various samples from Table III contain, in addition to structural information on the types of compounds present in the P/N fraction, information related to the ability of the P/N fraction to perform well in replacement of phenol in phenol-formaldehyde resins. By applying, for instance, cluster analysis to the FTIR (or MBMS, or NMR) data, the relationships between the variables (absorbances at certain wavenumbers, which are independent from one another, i.e., not linearly correlated) and samples (the various P/N products), which are not completely understood, are uncovered. The cluster analysis approach searches the system, without a priori assumptions about the data, to uncover the intrinsic structure or underlying behavior of the data set (see Sharaf et al. pp. 219–228). Samples, initially assumed to be unique, are systematically scanned and grouped together in clusters based on the degree of similarity of the spectra in the various samples. This is done by various mathematical methods, and in the data of FIG. 8, the centroid method was used. The figure, called a dendrogram, is a visual aid to the method, in which nine non-linearly correlated wavenumbers were used along with the absorbance information at each wavenumber, and the sample name. Samples with identical spectra have degrees of similarity of 1, whereas samples with very dissimilar spectra (such as outliers) have very low values in the degree of similarity (zero is the most dissimilar). For instance, in FIG. 8, the leftmost branch of the figure, the P/N product 14 is an outlier (batch, neutralized with dry carbonate in a very small scale, which did not reproduce very well the continuous sample preparation). The other sets of products cluster in groups: the redwood sample separated from the pine samples; within the pine samples, there are three clear families: Colorado pines, Southern pines, and high-severity samples from both Colorado and Southern pines (samples that were solvent-evaporated or transferred under high temperature for a long time). Indicated in the dendrogram are the clusters that also reflect qualitatively how good the gel properties of the samples are, and again, several Colorado and Southern pines P/N products lead to good gel properties in novolak production (see Table III for comments and gel times). Also indicated in the figure is that the reproducibility of the FTIR is good, since identical samples produce very high degrees of similarity (same value and near 1).

The fact that the spectral information distinguishes the degree of aging of the sample signifies that the spectral information could predict the physical property changes, such as viscosity changes of the various samples based on no knowledge of the thermal history of the sample.

In a similar way, principal component analysis was applied to the absorbance/wavenumber information without regard to the history or origin of the samples. The application of factor analysis to FTIR data for materials characterization has been widespread in the literature (see, for instance, P. M. Fredericks, J. B. Lee, P. R. Osborn, and D. J. Swinkels, "Materials Characterization using Factor Analysis of FTIR Spectra. Part 1: Results", Applied Spectroscopy, vol. 39, pp. 303-310, 1985, and "Materials Characterization using Factor Analysis of FTIR Spectra. Part 2: Mathematical and Statistical Considerations", Applied Spectroscopy, vol. 39, pp. 311-316, 1985; A. Holmgren and B. Norden, "Characterization of Peat Samples by Diffuse Reflectance FT-IR Spectroscopy", Applied Spectroscopy, vol. 42, pp. 255-262, 1988; S. M. Donahue, C. W. Brown, and R. Obremski, "Multicomponent Analysis Using Fourier Transform Infrared and UV Spectra", Applied Spectroscopy, vol. 42, pp. 353-359, 1988). Other physical property measurements and spectroscopic measurements such as the NMR, and other methods of data analyses such as partial least squares can be employed as well (M. P. Fuller, G. L. Ritter, and C. S. Draper, "Partial Least Squares Quantitative Analysis of Infrared Spectroscopic Data. Part II. Application to Detergent Analysis", Applied Spectroscopy, vol 42, pp. 228-236, 1988; L. Wallbacks, U. Edlund, and B. Norden, "Multivariate Analysis of In Situ Pulp Kinetics Using Carbon-13 CP/MAS NMR", J. Wood Chemistry and Technology, vol. 9, pp. 235-249, 1989). Fredericks et al. (see above) teach the application of such methods particularly well. Factor analyses of part (or all) of the FTIR spectra data set is used. In factor analysis, a combination of mathematical and interpretative methods derives a set of axes that efficiently displays the data vectors and the variance contained in the original measurement data, while giving some insight into the fundamental influences in the system represented by the data vectors (samples). Thus, the method allows the determination of the minimum number of factors (an eigenvector or other axis in the measurement space which can be interpreted according to the variables that contribute to it in a manner that identifies a source of influence in the data) and associated factor scores (the projection of the sample into the principal component plane) required to reproduce the spectra. Then multiple linear regression (using the software Statgraphics, in this case) of the factor scores ($X_1$ and $X_2$) against the measured properties, in this particular case, gel times and viscosities, gives close correlations which are used to predict the properties of unknown samples similar to those constituting the base set. Such methods are described as fast, compared to conventional techniques, and by suitable choice of the calibration set, can give semiquantitative results for a very wide range of samples, or quantitative results, of accuracy comparable with conventional techniques for a calibration set and unknowns from a narrower range of samples. The method has been applied successfully to substrates such as coal, peat, humic acid, bauxite, manganese dioxide ores, diesel fuel, wood pulp, detergents, and many others, to predict many different properties, such as energy content (of coal, peat, humic acids), ash content (coal, peat), and carbon, hydrogen, and oxygen contents (peat, coal, etc.), fine chemical structure and kinetics (wood delignification).

Table XII displays the results of the principal component analyses in terms of factor loadings (which relate the importance of each variable or wavenumber, in this case, in defining the principal component axis) and factor scores. The first two factor scores from the factor analysis of 17 wavenumbers in the FTIR of various P/N products, are used along with the observed gel times to derive the equation:

$$\text{Gel time} = 177 + 17.2X_1 - 9.5X_2 \ (r^2 = 0.84).$$

Figure 9:
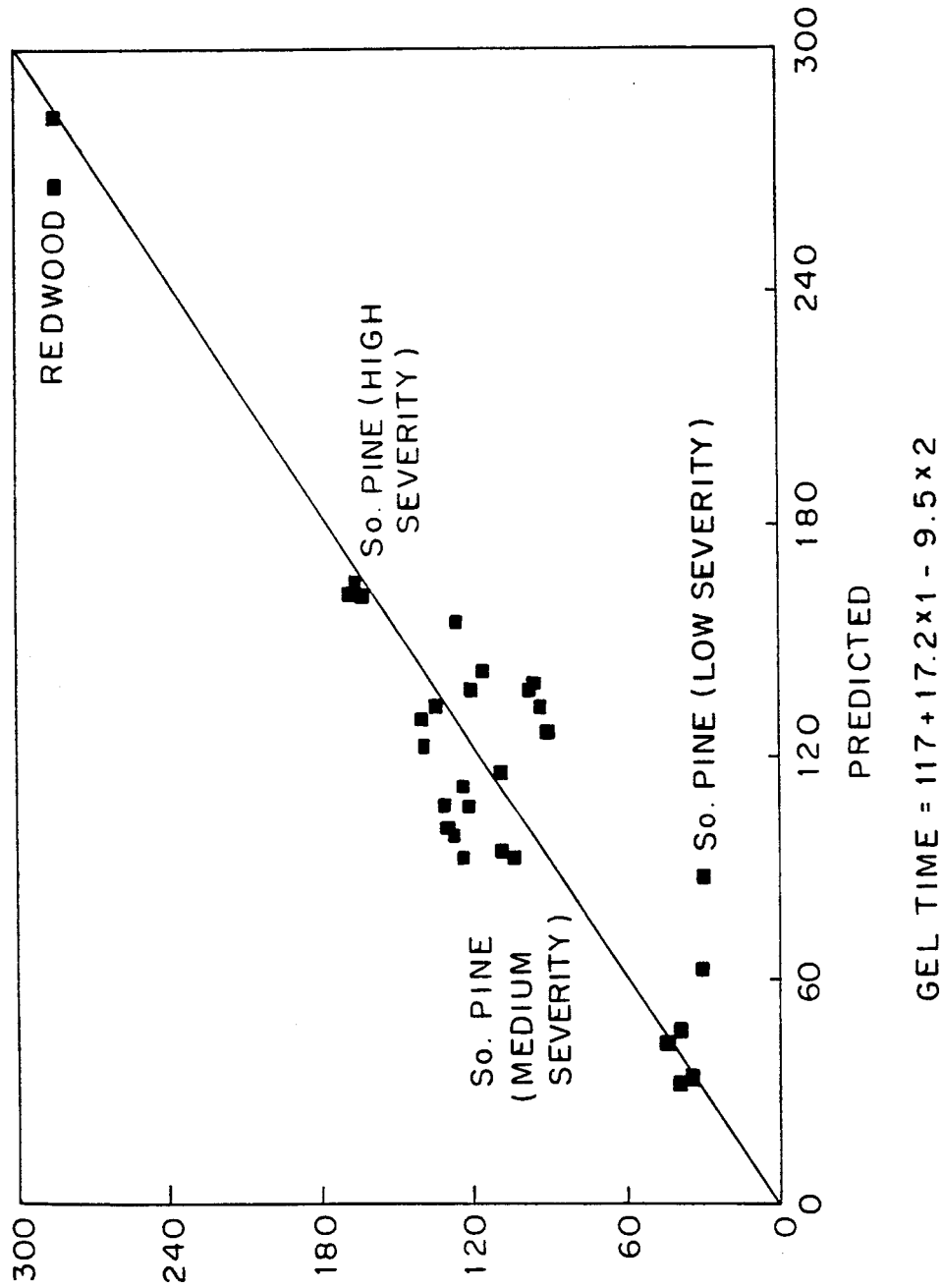
FIG. 9 illustrates the use of spectral data, similar to those shown in FIG. 3 for a variety of P/N products, in allowing the prediction of the resin properties such as gel times for a variety of feedstocks, through the use of principal component analysis and multiple linear regression of the factor scores ($X_1$ and $X_2$) and the gel times. The equation indicated in the figure allows the prediction of gel times based on knowledge of the factor scores from principal component analyses of a number of spectral data points.

Table XIII displays observed and predicted gel times for these P/N products, along with the residuals, also shown graphically on FIG. 9. Note that only two factors are necessary to explain the gel times. These two factors indeed contain the bulk ($>82\%$) of the variance in the measurement data set.

Similarly, a correlation was developed between the factor scores from the FTIR spectra (17 wavenumbers) and the water content of each P/N product with the log of the viscosity of these samples:

$$\text{Log viscosity} = 4.6 + 0.13X_1 + 0.25X_2 - 0.17$$
$$\text{water(wt \%)} \ (r^2 = 0.86).$$

Figure 10:
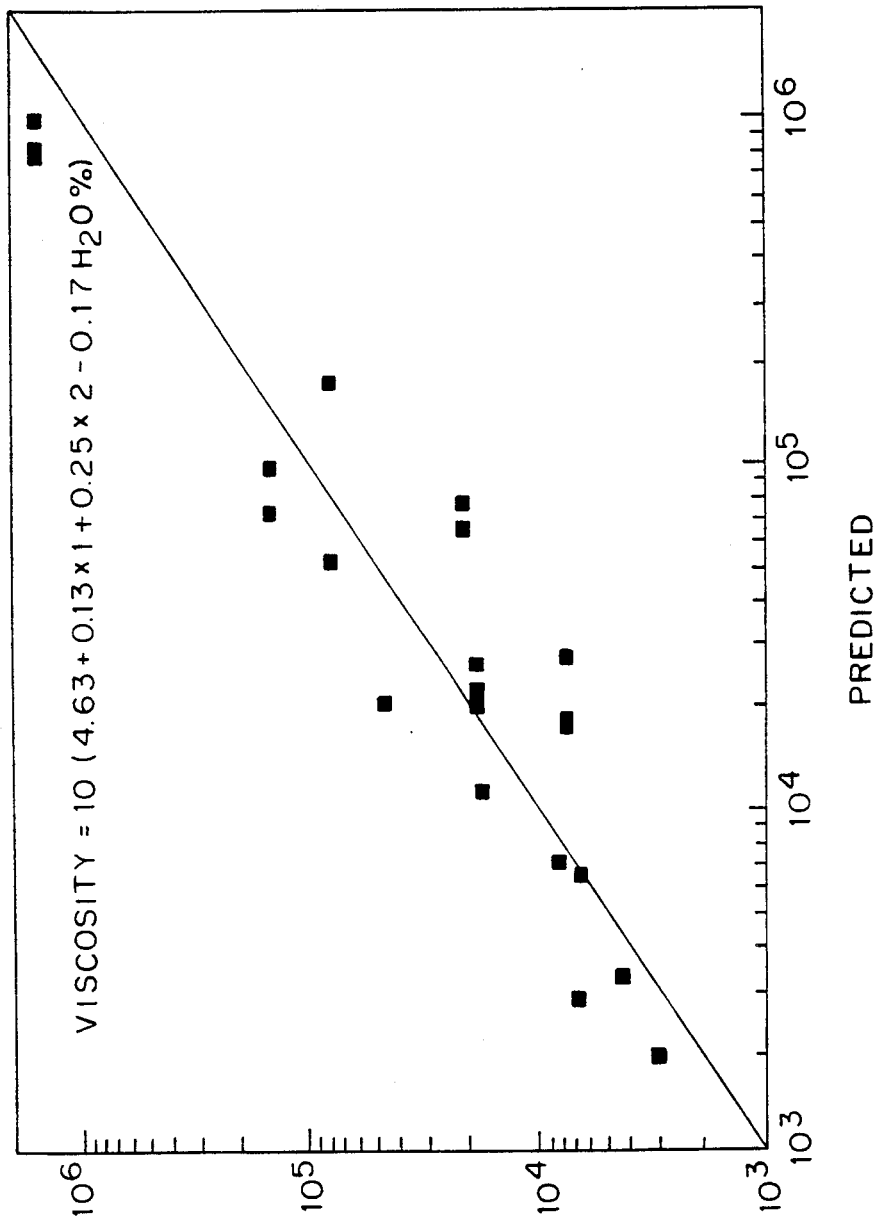
FIG. 10 illustrates in a manner analogous to that of FIG. 6, that the spectral properties combined with a knowledge of the water content allows one to predict the viscosity of the samples of P/N products from a variety of sources.

The plot of log viscosity predicted by this equation versus the observed values is shown on FIG. 10. The selected range of wavenumbers used in the principal component analysis do not include the key regions for water absorption in the IR spectral region, and for this reason, it is necessary to add the water content information from the direct measurement.

Sources of Variability in the P/N Products

Natural feedstocks have inherent composition variations, though pine species do not have as much variability as other feedstocks (see Sarkanen and Ludwig above). The examples described employed a mixture of Colorado Ponderosa and Lodgepole pines, as well as Southern pines from various locations (mostly loblolly, long, and shortleaf species). The southern pine species have on average, 28% lignin content, whereas the Colorado pines have about 26% lignin content. Another difference between Loblolly and Ponderosa pines (main representatives of Southern and Colorado pines, respectively) is the amount of extractives: 3 and 5%, respectively (these numbers are averages of more than 10 determinations each). A preliminary assessment of variability has been made for selected species: aspen *(Populus tremuloides)*, redwood, and douglas fir bark. Key differences were reported both in the phenolic hydroxyl and in the methoxyl contents (see above). The bark samples present a very high phenolic hydroxyl content, and in fact, contain resorcinol-type structures of higher reactivity towards formaldehyde than simpler phenolic structures. Preliminary novolaks made with this material indicated that they make prepolymers that have well defined low molecular weight distribution and a high ortho-novolak content. From these data it is clear that different feedstocks will yield P/N products of somewhat different properties, all of which are equally operable within the context of the invention.

The products are different in physical appearance. For instance, Douglas fir bark and redwood fast pyrolysis products tend to be solids, whereas the aspen and pine products are liquids under the pyrolysis conditions employed so far (increased severity of pyrolysis conditions is likely to move them into the lower molecular weight range of products, and therefore, into liquid products as well); solid P/N product formation requires different condensation techniques and optimization of fractionation for that particular species. Whereas aspen may not be as desirable a species as a softwood, because of a relatively low lignin content in the starting lignocellulosic material (e.g., 18-22% for aspen), it may have an offsetting cost advantage; bagasse is another species that produces upon pyrolysis the slate of products that is suitable for the replacement of phenol in phenol/formaldehyde thermosetting resins. The bark species may allow products in different markets to be penetrated because of the higher reactivity of these products.

From the data in FIGS. 9 and 10, the FTIR spectral information can provide a predictive tool for the quality and the relative gel time of the corresponding novolak and the P/N product viscosity (if the water is added as a parameter, since the viscosity is a marked function of the presence of low molecular weight components present in the P/N product). These characterization teachings and correlations demonstrate that the process described above can utilize a number of feedstocks, and that process conditions can then be tailored for the pyrolysis, fractionation, and solvent evaporation, so that a P/N product of desirable properties can be made. In the fractionation, the severity is imposed by the pH at which the extraction in ethyl acetate (or other solvent) is carried out. In order to produce reasonably high yields of P/N products, operation at about pH 6-7 is recommended. However, there are cases in which higher pHs may be desirable, and those can be reached with sodium carbonate or other bases. In the solvent evaporation, FIG. 4a clearly teaches how the severity of the process as a function of the operational conditions will affect the viscosity and molecular weight range of the P/N product. The higher the overall severity, the higher the viscosity, though it has been shown in one example that the higher viscosity products as well as the lower viscosity products can be used in the replacement of phenol in phenol-formaldehyde thermosetting resins, since the aging produces prepolymers which are primarily ether-bonded.

TABLE XII

Factor Loadings and Scores for the Two Most Important Factors in the Principal Component Analysis of the Absorbances at 17 Wavenumbers in the FTIR of the PN Samples.

| Wavenumber ($cm^{-1}$) | Factor Loadings | | Factor Scores | | |
|---|---|---|---|---|---|
| | X1 | X2 | Sample Code | X1 | X2 |
| 858 | 0.25 | 0.15 | XIV-48 | −2.69 | −2.64 |
| 1113 | 0.30 | 0.03 | XIV-84 | 0.58 | −0.38 |
| 1117 | 0.30 | −0.04 | XIV-80 | 6.84 | −3.06 |
| 1121 | 0.30 | −0.08 | XIV-80 | 8.52 | −1.89 |
| 1125 | 0.30 | −0.07 | XIV-48 | −1.75 | −1.72 |
| 1144 | 0.29 | −0.04 | XIV-84 | 0.49 | −0.18 |
| 1148 | 0.29 | −0.10 | XIX-93 | −0.61 | −1.42 |
| 1152 | 0.26 | −0.03 | BH-4-2 | −0.06 | −1.55 |
| 1206 | 0.15 | −0.45 | BH-4-1 | 1.37 | −1.22 |
| 1314 | 0.21 | 0.19 | XIX-84 | −1.11 | −0.54 |
| 1329 | 0.17 | 0.40 | XIX-12 | −0.04 | −0.87 |
| 1333 | 0.06 | 0.55 | XIX-12 | 0.44 | −1.08 |
| 1456 | 0.29 | 0.01 | XIX-50 | −1.90 | −0.54 |
| 1460 | 0.28 | 0.10 | XIX-12 | 0.79 | −0.56 |
| 1507 | 0.25 | 0.09 | XIX-50 | −1.30 | −0.34 |
| 1510 | 0.14 | −0.47 | XIII-27 | −0.21 | −2.70 |
| | | | XIII-27 | −0.50 | −2.80 |
| % of Variance explained | 64.5 | 18.2 | XX-84-RK | −4.20 | 1.30 |
| | | | XX-69-RK | −0.51 | 1.70 |
| | | | ARISTECH | 4.00 | 2.88 |
| | | | ARISTECH | 4.05 | 2.94 |
| | | | XX-84-RK | −3.60 | 1.30 |
| | | | XX-84-RK | −4.40 | 1.00 |
| | | | ARISTECH | 4.34 | 3.10 |
| | | | XX-69-RK | −0.67 | 1.60 |
| | | | XX-69-D | 0.71 | 2.16 |
| | | | Xx-84 | −3.29 | 1.56 |
| | | | XX-84-LOT1 | −0.74 | 1.90 |
| | | | XX-84-LOT2 | −2.40 | 1.40 |
| | | | XX-69-B | 1.05 | 2.28 |

Evaporation temperature (and pressure) as well as amount of added water for elimination of the azeotrope ethyl acetate/water allow process control to the desired degree of low molecular weight materials in the product, which decrease the viscosity and increase shelf life.

With respect to the economic benefits of the present invention, petroleum derived phenol costs about $0.34 (spot price) and $0.40 (list price) per pound. Prior to the present invention, the main competition has been the lignin-derived substitutes from commercial pulping processes. Kraft lignins have to be made chemically more reactive to replace phenol in phenol-formaldehyde resins with similar performance. These commercial products are sold as resin co-reactants, and their price ranges from $0.33-$0.85 per pound depending on the reactivity needed (based on Kraft lignins). Less expensive products available from the process of the present invention are co-reactants with the ability to replace about 50% of the phenol in phenol-formaldehyde resins as described above. Indications are that for molding compounds and for plywood adhesive resins, a 50% phenol replacement would provide comparable performance to the commercial phenolic adhesives. However, there is a significant cost reduction factor in that the phenol-replacing P/N products of the present invention have an amortized cost projection at approximately $0.16 per pound compared to $0.34-$0.40 per pound for commercial phenol. If the lignocellulosic starting material is bark, this cost is even less because the yield of phenolics from the bark is higher than that of sawdust or pine. These preliminary cost estimates were made for plant sizes of 250 to 1000 tons of feedstock per day, 15% return on capital, plant life of 10–20 years, and waste sawdust at $10.00 per dry ton.

As described above, the most developed application for the end products of the present invention is the replacement of about 50% and potentially more of the phenol in phenol-formaldehyde resins for use as molding compounds, foundry materials, and shell moldings. Other potential applications for the resulting product of the process of the present invention include the replacement of phenol in softwood and hardwood plywood resins, the insulation market, composite board adhesives, laminated beams, flooring and decking, industrial particle board, wet-formed hard boards, wet-formed insulation boards, structural panel board, and paper overlays. Alternative adhesive systems from the carbohydrate-rich fractions of the present invention could also be made.

In addition, another product that can be derived from the other fractions of the pyrolysis oils is an aromatic gasoline, rich in benzene, toluene and xylene. Passage of vapors of these compounds over zeolite catalysts produces high octane gasoline, as more clearly discussed in "Low-pressure upgrading of Primary Pyrolysis Oils from Biomass and Organic Waste," in Energy from Biomass and Wastes, Elsevier Applied Science Publishers, London, pp. 801–830 (1986).

A final advantage to the present invention is that about one-third of the usual amount of formaldehyde employed in conventional phenolic adhesives is necessary in producing adhesives wherein 50% of the phenol is substituted with P/N product provided by the present invention. Since there is significant environmental concern over formaldehyde emissions from resins, the products resulting from the process of the present invention therefore become very important from this context.

As can be seen from the above, a novel process for fractionating fast-pyrolysis oils to produce phenol-containing compositions having phenol/neutral fractions, the P/N product, contained therein, suitable for manufacturing phenol-formaldehyde resins is disclosed. The process is simple and economic, and can be used in either batch or continuous mode operations. The resulting P/N product composition can be subsequently utilized to produce novolaks and resole resins of comparable or superior performance characteristics relative to standard phenol-formaldehyde resins yet the pyrolysis-derived phenolic feedstocks are projected to cost less than half of the cost of petroleum-derived phenol. Moreover, these resulting resins have numerous different types of applications, and the cost benefits alone are significant.

While the foregoing description and illustration of the invention has been shown in detail with reference to preferred embodiments, it is to be understood that the foregoing are exemplary only, and that many changes in the compositions can be made without departing from the spirit and scope of the invention, which is defined by the attached claims.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is: The embodiments of the invention in which an exclusive property or privilege is claimed are defined as follows:

1. A process for fractionating organic and aqueous condensates made by fast-pyrolysis of biomass materials while using a carrier gas to move feed into a reactor to produce phenolic-containing/neutrals suitable for manufacturing phenol-formaldehyde resins, said process comprising:

admixing said organic and aqueous condensates with basic materials selected from the group consisting of sodium hydroxide, sodium bicarbonate, sodium carbonate, sodium sesquicarbonate, potassium hydroxide, potassium bicarbonate, potassium carbonate, ammonium hydroxide, ammonium bicarbonate, ammonium carbonate, lithium hydroxide, lithium bicarbonate, lithium carbonate, calcium hydroxide, calcium carbonate, magnesium hydroxide, magnesium carbonate, hydrates thereof, or mixtures thereof to neutralize acidic components of the condensates and to render said acidic components and polar compounds less soluble in organic phase;

admixing said neutralized condensates with an organic solvent having approximately 8.4 to 9.1 $(\text{cal/cm}^3)^{\frac{1}{2}}$ with polar components in the 1.9–3.0 range, a solubility parameter and hydrogen bonding components in the 2–4.8 range to extract phenolic-containing and neutral fractions from the organic and aqueous phases into a solvent phase;

separating the organic solvent-soluble fraction having the phenolic-containing and neutral fractions from the aqueous fraction; and removing the organic solvent to produce said phenolic-containing and neutrals compositions in a form substantially free from said solvent.

2. A process for fractionating organic and aqueous condensates made by fast-pyrolysis of biomass materials while using a carrier gas to move feed into a reactor to produce phenolic-containing/neutrals extract, wherein the neutral fractions have molecular weights of 100 to 800; said extract being suitable for a part of the phenol for manufacturing phenol-formaldehyde resins, said process comprising:

admixing said condensates with an organic solvent having a solubility parameter of 8.4 to 9.1 $(\text{cal/cm}^3)^{\frac{1}{2}}$ with polar components in the 1.9–3.0 range and hydrogen bonding components in the 2–4.8 range to extract phenolic-containing and neutral fractions from said condensates into a solvent phase;

admixing said organic and aqueous condensates with basic materials selected from the group consisting of sodium hydroxide, sodium carbonate, sodium sesquicarbonate, potassium hydroxide, potassium carbonate, ammonium hydroxide, ammonium carbonate, lithium hydroxide, lithium carbonate, calcium hydroxide, calcium carbonate, magnesium hydroxide, magnesium carbonate, hydrates thereof, or mixtures thereof to neutralize acidic components of the condensates and to render said acidic components and polar compounds less soluble in organic phase;

separating the organic solvent-soluble fraction having the phenolic-containing and neutral fractions from the aqueous fraction; and removing the organic solvent to produce said phenolic-containing and neutrals compositions in a form substantially free from said solvent.

3. The process of claim 1, wherein steam recycled gases plus steam on an inert gas is the carrier gas.

4. The process of claim 1, wherein said organic solvent also exhibits low mutual solubility with water.

5. The process of claim 1, wherein said organic solvent is selected from the group consisting of acetate esters, methyl ketone, ethyl ketones and mixtures thereof.

6. The process of claim 5, wherein said organic solvent is selected from the group consisting of ethyl acetate, butyl acetate, methylisobutyl ketone and mixtures thereof.

7. The process of claim 6, wherein said organic solvent comprises ethyl acetate.

8. The process of claim 7, wherein the extraction utilizing ethyl acetate solvent is performed at a pH of approximately 6 to 8.

9. The process of claim 8, wherein the extraction utilizing ethyl acetate solvent is performed at a pH of about 6.5 to 7.5.

10. The process of claim 1, wherein said basic material is in a relatively dry, solid state.

11. The process of claim 1, wherein said basic material is dry sodium bicarbonate.

12. The process of claim 1, wherein said basic material is dry sodium carbonate.

13. The process of claim 1, wherein said basic material is a dry, hydrated form of sodium carbonate.

14. The process of claim 1, wherein said basic material is dry calcium carbonate.

15. The process of claim 1, wherein said basic material is dry calcium hydroxide.

16. The process of claim 1, wherein said basic material is an aqueous solution of sodium carbonate.

17. The process of claim 1, wherein said basic material is a slurry of sodium bicarbonate.

18. The process of claim 1, wherein said basic material is a slurry of sodium carbonate.

19. The process as claimed in claim 1, wherein said basic material is a slurry of calcium carbonate.

20. The process of claim 1, wherein said basic material is a slurry of calcium hydroxide in a suitable liquid.

21. The process of claim 1, wherein said neutralized pyrolysis condensates and condensed carrier steam are admixed with said organic solvent in a solvent-to-dry-pyrolyzed-feed ratio of between 1 to 5 by weight, including solvent used to wash condensing equipment and/or to transfer the condensates into a neutralization tank.

22. The process of claim 1, wherein said organic solvent is removed from a residual organic fraction by evaporation to provide a substantially solvent free phenolic-containing/neutrals composition.

23. The process of claim 1, wherein said fast-pyrolysis condensates are produced from biomass materials that are lignocellulosic materials.

24. The process of claim 1, wherein said lignocellulosic materials are selected from the group consisting of softwoods, hardwoods, bark of tree species, and grasses.

25. The process of claim 24, wherein said softwoods are selected from pine and redwood.

26. The process of claim 24, wherein said hardwood is aspen.

27. The process of claim 24, wherein said bark of tree species is Douglas fir.

28. The process of claim 24, wherein said grass is bagasse.

29. The process of claim 1, wherein said phenolic-containing/neutrals fraction compositions are capable of substituting for up to 75% of phenol in phenol-formaldehyde resins.

30. The process of claim 22, wherein said phenolic-containing/neutrals compositions include a high phenolic, hydroxyl and aldehyde content.

31. The process of claim 22, wherein said organic solvent is evaporated from a residual organic solvent fraction, and said phenolic-containing/neutral composition is in a substantially solvent free condition to form a basis for resin applications, such as molding compounds and adhesives.

32. The process of claim 1, wherein said process is a series of batch processes.

33. The process of claim 1, wherein said process is a series of continuous processes.

34. The process claim 1, wherein said process is a mixture of batch and continuous processes.

35. The process of claim 34, wherein said neutralization is a batch process and the extraction is a continuous process.

36. An adhesive resin containing the phenolic-containing and neutral fraction produced by the process of claim 1.

37. A process for fractionating organic and aqueous condensates made by fast-pyrolysis of lignocellulosic materials while using a carrier gas to move feed into a reactor to produce a phenolic-containing/neutral composition suitable for manufacturing phenol-formaldehyde type resins, said process comprising:

admixing said organic and aqueous condensates with materials that neutralize acidic components of the condensates and render said acidic components and other polar compounds less soluble in an organic phase;

admixing said neutralized condensates with ethyl acetate to extract phenolic-containing and neutral fractions from the organic and aqueous phases into an ethyl acetate phase;

separating ethyl-acetate-soluble fraction having phenolic-containing and neutral fractions from an aqueous fraction; and removing the ethyl acetate solvent from the organic phase to produce said phenolic-containing and neutrals compositions in a form substantially free from ethyl acetate.

38. The process of claim 37, wherein the carrier gas is steam.

39. The process of claim 37, wherein extraction utilizing ethyl acetate solvent is performed at a pH of approximately 6 to 8.

40. The process of claim 37, wherein extraction utilizing ethyl acetate solvent is performed at a pH of 6.5 to 7.5.

41. The process of claim 37, wherein said neutralizing material is in a relatively dry state and is selected from the group consisting of sodium hydroxide, sodium bicarbonate, sodium carbonate, sodium sesquicarbonate, potassium hydroxide, potassium bicarbonate, potassium carbonate, ammonium hydroxide, ammonium bicarbonate, ammonium carbonate, lithium hydroxide, lithium bicarbonate, lithium carbonate, calcium hydroxide, calcium carbonate, magnesium hydroxide, magnesium carbonate, or hydrates thereof, or mixtures thereof.

42. The process of claim 37, wherein said neutralizing material is in a relatively dry state and is sodium bicarbonate.

43. The process as claimed in claim 37, wherein said neutralizing material is in a relatively dry state and is sodium carbonate or hydrates of sodium carbonate.

44. The process as claimed in claim 37, wherein said neutralizing material is in a relatively dry state and is sodium sesquicarbonate.

45. The process as claimed in claim 37, wherein said neutralizing material is in a relatively dry state and is calcium carbonate.

46. The process as claimed in claim 37, wherein said neutralizing material is in a relatively dry state and is calcium hydroxide.

47. The neutralizing materials as claimed in claim 41, wherein said neutralizing material is in a slurry form in a suitable liquid.

48. The process as claimed in claim 37, wherein said neutralizing material is in an aqueous solution and is selected from the group of sodium hydroxide, sodium carbonate, sodium sesquicarbonate, potassium hydroxide, potassium carbonate, potassium bicarbonate, lithium hydroxide, lithium carbonate, lithium bicarbonate, ammonium hydroxide, ammonium carbonate, or mixtures thereof.

49. The process of claim 37, wherein said neutralized pyrolysis condensates and condensed carrier steam are admixed with ethyl acetate solvent in a solvent-to-dry-lignocellulosic-feed ratio of between 1 to 5 by weight, including solvent used to wash condensing equipment and/or to transfer the condensates into a neutralization tank.

50. The process of claim 37, wherein said ethyl acetate is removed from a residual organic fraction by evaporation to provide a substantially solvent free phenolic-containing/neutrals composition.

51. The process of claim 37, wherein said lignocellulosic materials are selected from the group consisting of: softwoods, hardwoods, bark, and grasses.

52. The process of claim 37, wherein said softwood are pine and redwood.

53. The process of claim 37, wherein said hardwood is aspen.

54. The process of claim 37, wherein said phenolic-containing compositions include phenolic and neutral fractions therefore present.

55. The process of claim 37, wherein said phenolic-containing/neutrals fraction compositions are capable of substituting for up to 75% of phenol in phenol-formaldehyde resins.

56. The process of claim 46, wherein said phenolic-containing/neutrals compositions include a high phenolic hydroxyl and aldehyde content.

57. The process of claim 50, wherein said ethyl acetate solvent is evaporated from a residual organic fraction, and said phenolic-containing/neutral composition is in a substantially solvent free condition to form a basis for resin applications, such as molding compounds and adhesives.

58. The process of claim 37, wherein a portion of said organic solvent/pyrolysis condensate not extracted into an organic solvent-soluble fraction is further processed utilizing zeolite catalysts to form gasoline.

59. The process of claim 37, wherein said process is a series of batch processes.

60. The process of claim 37, wherein said process is a series of continuous processes.

61. The process of claim 37, wherein said process is a mixture of batch and continuous processes.

62. The process of claim 60, wherein said neutralization is a batch process and said extraction is a continuous process.

63. An adhesive resin having the phenolic-containing and neutrals fraction produced by the process of claim 37.

64. A process for fractionating organic and aqueous condensates made by fast-pyrolysis of lignocellulosic materials while using steam as a carrier gas to move feed into and char out of a reactor to produce a phenolic-containing/neutral composition suitable for manufacturing phenol-formaldehyde type resins, said process comprising:

admixing said organic and aqueous condensates with dry sodium carbonate to neutralize acidic components of the acidic components and other polar compounds less soluble in an organic phase;

admixing said neutralized condensates with ethyl acetate in a weight ratio of ethyl acetate solvent to dry lignocellulosic feed of between 1 and 5 to extract phenolic-containing and neutral fractions from organic and aqueous phases into an ethyl acetate phase;

separating an ethyl-acetate-soluble fraction having the phenolic-containing and neutral fractions from the aqueous fraction; and removing the ethyl acetate solvent to produce said phenolic-containing and neutrals compositions in a form substantially free from ethyl acetate.

65. The process of claim 37, wherein said phenolic-containing and neutrals fractions are used as a basis to produce molded articles and adhesives.

66. A process for fractionating organic and aqueous condensates made by fast-pyrolysis of lignocellulosic materials while using steam as a carrier gas to move feed into and char out of a reactor to produce a phenolic-containing/neutral composition suitable for manufacturing phenol-formaldehyde type resins, said process comprising:

admixing said organic and aqueous condensates with dry sodium bicarbonate to neutralize acidic components of the condensates to a pH of between 6.5 and 7.5 to render said acidic components and other polar compounds less soluble in the organic phase;

admixing said neutralized condensates with ethyl acetate at a ratio of between 1 and 5 kg ethyl acetate per kg of dry feed to extract phenolic-containing and neutral fractions from the organic and aqueous phases into a ethyl acetate phase;

separating an ethyl-acetate-soluble fraction having a phenolic-containing and neutral fractions from an aqueous fraction; and removing ethyl acetate solvent to produce said phenolic-containing and neutrals compositions in a form substantially free from ethyl acetate.

67. The process of claim 66, wherein said phenolic-containing and neutrals fractions are used as basis to produce molded articles and adhesives.

68. The process of claim 1, wherein the carrier gas used is noncondensible, but where sufficient water is present in the condensates of fast-pyrolysis to form an aqueous phase and an organic phase, and wherein said aqueous phase is sufficiently large to extract water soluble organic compounds from the organic phase and to serve as an ionizing media for material used to neutralize acidic organic compounds present.

69. The process of claim 37, wherein the carrier gas used is noncondensible, but where sufficient water is present in the condensates of fast-pyrolysis to form an aqueous phase and an organic phase, and wherein said aqueous phase is sufficiently large to extract water soluble organic compounds from the ethyl acetate phase and to serve as ionizing media for material used to neutralize acidic organic compounds present.

70. The process of claim 64, wherein the carrier gas used is noncondensible, but where sufficient water is present in condensates of fast-pyrolysis to form an aqueous phase and an organic phase, and wherein said aqueous phase is sufficiently large to extract water soluble organic compounds from the ethyl acetate phase and to serve as an ionizing media for the sodium carbonate used to neutralize the acidic organic compounds present.

71. The process of claim 66, wherein the carrier gas used is noncondensible, but where sufficient water is present in condensates of fast-pyrolysis to form an aqueous phase and an organic phase, and wherein said with the aqueous phase is sufficiently large to extract the water soluble organic compounds from the ethyl acetate phase and to serve as ionizing media for the sodium bicarbonate used to neutralize acidic organic compounds present.

72. The process of claim 21, wherein said organic solvent is evaporated in a way as to produce a product having sufficient water remaining to provide a lower viscosity for ease of handling.

73. The process of claim 50, wherein said organic solvent is evaporated in a way as to produce a product having sufficient water remaining to provide a lower viscosity for ease of handling.

74. The process of claim 64, wherein said ethyl acetate is removed by evaporation in a way to produce a product having sufficient water remaining to provide a lower a viscosity for ease of handling.

75. The process of claim 66, wherein said ethyl acetate is removed by evaporation in a way to produce a product having sufficient water remaining to provide a lower viscosity for ease of handling.

76. The process of claim 72, wherein said organic solvent is partially or wholly evaporated by direct contact with steam.

77. The process of claim 73, wherein said organic solvent is partially or wholly evaporated by direct contact with steam.

78. The process of claim 74, wherein said ethyl acetate is partially or wholly evaporated by direct contact with steam.

79. The process of claim 75, wherein said ethyl acetate is partially or wholly evaporated by direct contact with steam.

80. The process of claim 1, wherein the organic solvent is recovered from the aqueous phase by evaporation.

81. The process of claim 38, wherein the organic solvent is recovered from the aqueous phase by evaporation.

82. The process of claim 64, wherein the ethyl acetate is recovered from the aqueous phase by evaporation.

83. The process of claim 66, wherein the ethyl acetate is recovered from the aqueous phase by evaporation.

84. The process of claim 80, wherein heat for evaporation is supplied by direct contact with steam.

85. The process of claim 81, wherein heat for evaporation is supplied by direct contact with steam.

86. The process of claim 82, wherein heat for evaporation is supplied by direct contact with steam.

87. The process of claim 83, wherein heat for evaporation is supplied by direct contact with steam.

88. The process of claim 1, wherein pyrolysis vapors are subjected to subsequent controlled thermal treatment after their formation to minimize the formation of precipitates during the neutralization and/or extraction steps.

89. The process of claim 39, wherein pyrolysis vapors are subjected to subsequent thermal treatment after their formation to minimize formation of precipitates during the neutralization and/or extraction steps.

90. The process of claim 64, wherein pyrolysis vapors are subjected to subsequent thermal treatment after their formation to minimize formation of precipitates during the neutralization and/or extraction steps.

91. The process of claim 66, wherein pyrolysis vapors are subjected to subsequent thermal treatment after their formation to minimize formation of precipitates during the neutralization and/or extraction steps.

92. The process of claim 1, wherein the aqueous phase is decanted and neutralized separately from the organic phase and then admixed with the organic phase to neutralize the organic phase.

93. The process as claimed in claim 33, wherein the aqueous phase is decanted and neutralized separately from the organic phase and then admixed with the organic phase to neutralize the organic phase.

94. The process of claim 64, wherein the aqueous phase is decanted and neutralized separately from the organic phase and then admixed with the organic phase to neutralize the organic phase.

95. The process of claim 60, wherein the aqueous phase is decanted and neutralized separately from the organic phase and then admixed with the organic phase to neutralize the organic phase.

96. The process of claim 5, wherein a part or all of the solvent used in the extraction is added prior to the neutralization.

97. The process of claim 37, wherein a part or all of the ethyl acetate solvent is added prior to neutralization.

98. The process of claim 58, wherein a part or all of the ethyl acetate solvent is added prior to the neutralization.

99. The process of claim 60, wherein a part or all of the ethyl acetate solvent is added prior to neutralization.

100. A phenolic compounds-containing/neutral fractions extract obtained by fractionating fast-pyrolysis oils from biomass materials;
   said extract being soluble in an organic solvent having a solubility parameter of approximately 8.4.–9.1 $[cal/cm^3]^{\frac{1}{2}}$ polar components in the 1.8–3.0 range and hydrogen bonding components in the 2–4.8 range, after washing with water and then extracting with dry metal carbonates or bicarbonates or an aqueous metal bicarbonate solution at a pH range of between about 8–9.5 to purify said phenolic compounds-containing/neutral fractions extract.

101. The phenolic compounds-containing/neutral fractions extract of claim 100, wherein the biomass material is pine sawdust.

102. The phenolic compounds-containing/neutral fractions extract of claim 100, wherein the biomass material is Douglas fir bark.

103. The phenolic compounds-containing/neutral fractions extract of claim 100, wherein said organic solvent is selected from the group consisting of acetate and propionate esters, methyl alkyl ketones, ethyl alkyl ketones and mixture 104. The phenolic compounds-containing/neutral fractions extract of claim 103, wherein said organic solvent is selected from the group consisting of ethyl acetate, butyl acetate and methyl isobutyl ketone.

105. The phenolic compounds-containing/neutral fractions extract of claim 104, wherein said organic solvent is ethyl acetate.

106. The phenolic compounds-containing/neutral fractions extract of claim 101, wherein the organic solvent is selected from the group consisting of acetate and propionate esters, methyl alkyl ketones, and ethyl alkyl ketones.

107. The phenolic compounds-containing/neutral fractions extract of claims 106, wherein said organic solvent is selected from the group consisting of ethyl acetate, butyl acetate and methyl isobutyl ketone.

108. The phenolic compounds-containing/neutral fractions extract of claim 107, wherein said organic solvent is ethyl acetate.

109. The phenolic compounds-containing/neutral fractions extract of claim 102, wherein said organic solvent is selected from the group consisting of acetate and propionate esters, methyl alkyl ketones, and ethyl alkyl ketones.

110. The phenolic compounds-containing/neutral fractions extract of claim 109 wherein said organic solvent is selected from the group consisting of ethyl acetate, butyl acetate and methyl isobutyl ketone.

111. The phenolic compounds-containing/neutral fractions extract of claim 104, wherein said organic solvent is ethyl acetate.

112. The phenolic compounds-containing/neutral fractions extract from claim 100, wherein said neutral fractions have molecular weights from 100-800.

113. The phenolic compounds-containing/neutral fractions extract from claim 104, wherein said organic solvent is propyl acetate.

114. The phenolic compounds-containing/neutral fractions extract from claim 109, wherein said organic solvent is propyl acetate.

115. The phenolic compounds-containing/neutral fractions extract from claim 113, in a dried state and containing traces of water.

116. The phenolic compounds-containing/neutral fractions extract from claim 114, in a dried state and containing traces of water.

* * * * *